(12) United States Patent
Bartlett et al.

(10) Patent No.: US 7,749,492 B2
(45) Date of Patent: Jul. 6, 2010

(54) AAV VECTORS AND METHODS

(75) Inventors: Jeffrey S. Bartlett, Worthington, OH (US); Matthew Stachler, Blacklick, OH (US)

(73) Assignee: Nationwide Children's Hospital, Inc., Columbus, OH (US)

( * ) Notice: Subject to any disclaimer, the term of this patent is extended or adjusted under 35 U.S.C. 154(b) by 530 days.

(21) Appl. No.: 11/145,035

(22) Filed: Jun. 3, 2005

(65) Prior Publication Data

US 2005/0287122 A1  Dec. 29, 2005

Related U.S. Application Data

(63) Continuation-in-part of application No. 10/038,972, filed on Jan. 4, 2002, now Pat. No. 6,962,815.

(60) Provisional application No. 60/260,124, filed on Jan. 5, 2001.

(51) Int. Cl.
*C12N 15/864* (2006.01)
*C12N 15/34* (2006.01)
*C12N 15/64* (2006.01)
*C07K 14/025* (2006.01)
*C07K 14/005* (2006.01)
*C07K 1/00* (2006.01)

(52) U.S. Cl. ............... 424/93.2; 424/93.1; 530/350; 530/300; 530/388.2; 530/387.9; 435/455; 435/320.1; 435/325

(58) Field of Classification Search .............. None
See application file for complete search history.

(56) References Cited

U.S. PATENT DOCUMENTS 6,491,907 B1 * 12/2002 Rabinowitz et al. ......... 424/93.2
2006/0286545 A1 * 12/2006 Weber et al. .................. 435/5

FOREIGN PATENT DOCUMENTS

WO  WO00/28004  5/2000

OTHER PUBLICATIONS

Wu et al, Mutational Analysis of the Adeno-Associated Virus Type 2 (AAV2) Capsid Gene and Construction of AAV2 Vectors with Altered Tropism, Journal of Virology, Sep. 2000, p. 8635-8647, vol. 74, No. 18.*
Buning et al, Receptor targeting of adeno-associated virus vectors, Gene Therapy (2003) 10, 1142-1151.*
Shi et al, Insertional Mutagenesis of the Adeno-Associated Virus Type 2 (AAV2) Capsid Gene and Generation of AAV2 Vectors Targeted to Alternative Cell-Surface Receptors, Human Gene Therapy 12:1697-1711 (Sep. 20, 2001).*
Agbandje et al., "Structure Determination Of Feline Panleukopenia Virus Empty Particles," *Proteins*, 16: 155-171 (Jun. 1993).
Agbandje-McKenna et al., "Functional Implications Of The Structure Of The Murine Parvovirus, Minute Virus Of Mice," *Structure*, 6(11): 1369-1381 (Nov. 1998).

Bartlett et al., "Infectious Entry Pathway Of Adeno-Associated Virus And Adeno-Associated Virus Vectors," *Journal of Virology*, 74(6): 2777-2785 (1999).
Chiorini et al., "Cloning Of Adeno-Associated Virus Type 4 (AAV4) And Generation Of Recombinant AAV4 Particles," *Journal of Virology*, 6823-6833 (Sep. 1997).
Chiorini et al., "Cloning And Characterization Of Adeno-Associated Virus Type 5," *Journal of Virology*, 73(2): 1309-1319 (Feb. 1999).
Chipman et al., "Cryo-Electron Microscopy Studies Of Empty Capsids Of Human Parvovirus B19 Complexed With Its Cellular Receptor," *Proc. Natl. Acad. Sci. USA*, 93: 7502-7506 (Jul. 1996).
Genbank Accession No. AF043303, "Adeno-Associated Virus 2" (Feb. 24, 1998).
Girod et al., "Genetic Capsid Modifications Allow Efficient Re-Targeting Of Adeno-Associated Virus Type 2," *Nature Medicine*, 5(9): 1052-1056 (Sep. 1999).
Hermonat et al., "Genetics Of Adeno-Associated Virus: Isolation And Preliminary Characterization Of Adeno-Associated Virus Type 2 Mutants," *Journal of Virology*, 51(2): 329-339 (Aug. 1984).
Kigawa et al., "Adenovirus-Mediated Transfer Of A p. 53 Gene In Ovarian Cancer," *Adv. Exp. Med. Biol.*, 465(14): 207-214 (2000).
Llamas-Saiz et al., "Structure Determination Of Minute Virus Of Mice," *Acta Crystallographica Section D*, D53: 93-102 (1997).
McKenna et al., "Three-Dimensional Structure Of Aleutian Mink Disease Parvovirus: Implications For Disease Pathogenicity," *Journal of Virology*, 73(8): 6882-6891 (Aug. 1999).
Moskalenko et al., "Epitope Mapping of Human Anti-Adeno-Associated Virus Type 2 Neutralizing Antibodies: Implications For Gene Therapy And Virus Structure," *Journal of Virology*, 74(4): 1761-1766 (Feb. 2000).
Muramatsu et al., "Nucleotide Sequencing And Generation Of An Infectious Clone Of Adeno-Assocaited Virus 3," *Virology*, 221: 208-217 (1996).
Muzyczka, "Use Of Adeno-Associated Virus As A General Transduction Vector For Mammalian Cells," *Current Topics In Microbiology And Immunology*, 158: 97-129 (1992).
Rabinowitz et al., "Insertional Mutagenesis of AAV2 Capsid And The Production Of Recombinant Virus," *Virology*, 265: 274-285 (1999).
Ruffing et al., "Mutations In The Carboxy Terminus Of Adeno-Associated Virus 2 Capsid Proteins Affect Viral Infectivity: Lack Of An RGD Integrin-Binding Motif," *Journal of General Virology*, 75: 3385-3392 (1994).
Rutledge et al., "Infectious Clones And Vectors Derived From Adeno-Associated Virus (AAV) Serotypes Other Than AAV Type 2," *Journal of Virology*, 72(1): 309-319 (Jan. 1998).
Santiago et al., "New DNA Enzyme Targeting Egr-1 mRNA Inhibits Vascular Smooth Muscle Proliferation And Regrowth After Injury," *Nature Medicine*, 5(11): 1264-1269 (Nov. 1999).

(Continued)

* cited by examiner

*Primary Examiner*—Maria Marvich
(74) *Attorney, Agent, or Firm*—Marshall, Gerstein & Borun LLP

(57) ABSTRACT

The invention relates to Adeno-associated virus vectors. In particular, it relates to Adeno-associated virus vectors with modified capsid proteins and materials and methods for their preparation and use.

19 Claims, 7 Drawing Sheets

OTHER PUBLICATIONS

Shi et al., "Insertional Mutagenesis Of The Adeno-Associated Virus Type 2 (AAV2) Capsid Gene And Construction Of AAV2 Vectors Targeted To Alternative Cell-Surface Receptors," *Human Gene Therapy*, 12: 1697-1711 (Sep. 2001).

Song et al., "In Vivo Studies Of Adenovirus-Mediated P53 Gene Therapy For Cis-Platinum-Resistent Human Ovarian Tumor Xenografts," *Oncol. Res.*, 11(3): 153-159m (1999).

Srivastava et al., "Nucleotide Sequence and Organization of the Adeno-Associated Virus 2 Geneome," *Journal of Virology*, 45(2): 555-564 (Feb. 1983).

Tsao et al., "The Three-Dimensional Structure Of Canine Parvovirus And Its Functional Implications," *Science* 251: 1456-1464 (Mar. 1991).

Wu et al., "The Canine Parvovirus Empty Capsid Structure," *J. Mol. Biol.*, 233(2): 231-244 (1993).

Wu et al., "Mutational Analysis Of The Adeno-Associated Virus Type 2 (AAV2) Capsid Gene And Construction Of AAV2 Vectors With Altered Tropism," *Journal of Virology* 74(18): 8635-8647 (Sep. 2000).

Xie et al., "The Atomic Structure Of Adeno-Associated Virus (AAV-2), A Vector For Human Gene Therapy," *Proc. Natl. Acad. Sci, U.S.A.*, 99(16): 10405-10410 (Aug. 6, 2002).

Yamaguchi et al., "Co-Transfection Of Herpes Simplex Virus Thymidine Kinase Gene And Human Interleukin-2 Gene Into Mouse Ovarian Cancer Call Line, OVHM," *Intl. J. Mol. Med.*, 6(2): 185-190 (2000).

Fig. 1A

```
                          10        20        30        40        50
                           |         |         |         |         |
AAV2  SEQ ID NO: 13  MAADGYLPDWLEDTLSEGIRQWWKLKPGPPPPKPAERHKDDSRGLVLPGY
AAV1  SEQ ID NO: 20  MAADGYLPDWLEDNLSEGIREWWDLKPGAPKPKANQQKQDDGRGLVLPGY
AAV3  SEQ ID NO: 22  MAADGYLPDWLEDNLSEGIREWWALKPGVPQPKANQQHQDNRRGLVLPGY
AAV4  SEQ ID NO: 24  -MTDGYLPDWLEDNLSEGVREWWALQPGAPKPKANQQHQDNARGLVLPGY
AAV5  SEQ ID NO: 36  MSFVDHPPDWLEE-VGEGLREFLGLEAGPPKPKPNQQHQDQARGLVLPGY
AAV6  SEQ ID NO: 26  MAADGYLPDWLEDNLSEGIREWWDLKPGAPKPKANQQKQDDGRGLVLPGY
AAV7  SEQ ID NO: 38  MAADGYLPDWLEDNLSEGIREWWDLKPGAPKPKANQQKQDNGRGLVLPGY
AAV8  SEQ ID NO: 40  MAADGYLPDWLEDNLSEGIREWWALKPGAPKPKANQQKQDDGRGLVLPGY
AAV9  SEQ ID NO: 43  MAADGYLPDWLEDTLSEGIRQWWKLKPGPPPPKPAERHQDNSRGLVLPGY
AAV10 SEQ ID NO: 41  MAADGYLPDWLEDNLSEGIREWWDLKPGAPKPKANQQKQDDGRGLVLPGY
AAV11 SEQ ID NO: 42  MAADGYLPDWLEDNLSEGIREWWDLKPGAPKPKANQQKQDDGRGLVLPGY
                     .: *****: :.**:*::  *:.* * **. ::::*: *******
         Prim.cons.  MAADGYLPDWLEDNLSEGIREWWDLKPGAPKPKANQQKQDDGRGLVLPGY 60        70        80        90       100
                           |         |         |         |         |
AAV2  SEQ ID NO: 13  KYLGPFNGLDKGEPVNEADAAALEHDKAYDRQLDSGDNPYLKYNHADAEF
AAV1  SEQ ID NO: 20  KYLGPFNGLDKGEPVNAADAAALEHDKAYDQQLKAGDNPYLRYNHADAEF
AAV3  SEQ ID NO: 22  KYLGPGNGLDKGEPVNEADAAALEHDKAYDQQLKAGDNPYLKYNHADAEF
AAV4  SEQ ID NO: 24  KYLGPGNGLDKGEPVNAADAAALEHDKAYDQQLKAGDNPYLKYNHADAEF
AAV5  SEQ ID NO: 36  NYLGPGNGLDRGEPVNRADEVAREHDISYNEQLEAGDNPYLKYNHADAEF
AAV6  SEQ ID NO: 26  KYLGPFNGLDKGEPVNAADAAALEHDKAYDQQLKAGDNPYLRYNHADAEF
AAV7  SEQ ID NO: 38  KYLGPFNGLDKGEPVNAADAAALEHDKAYDQQLKAGDNPYLRYNHADAEF
AAV8  SEQ ID NO: 40  KYLGPFNGLDKGEPVNAADAAALEHDKAYDQQLQAGDNPYLRYNHADAEF
AAV9  SEQ ID NO: 43  KYLGPSNGLDKGEPVNEADAAALEHDKAYDRQLDSGDNPYLKYNHADAEF
AAV10 SEQ ID NO: 41  KYLGPFNGLDKGEPVNAADAAALEHDKAYDQQLKAGDNPYLRYNHADAEF
AAV11 SEQ ID NO: 42  KYLGPFNGLDKGEPVNAADAAALEHDKAYDQQLKAGDNPYLRYNHADAEF
                     :**** ****:***** **  * *** :*:.**.:******:*******
         Prim.cons.  KYLGPFNGLDKGEPVNAADAAALEHDKAYDQQLKAGDNPYLRYNHADAEF 110       120       130       140       150
                           |         |         |         |         |
AAV2  SEQ ID NO: 13  QERLKEDTSFGGNLGRAVFQAKKRVLEPLGLVEEPVKTAPGKKRPVEHSP
AAV1  SEQ ID NO: 20  QERLQEDTSFGGNLGRAVFQAKKRVLEPLGLVEEGAKTAPGKKRPVEQSP
AAV3  SEQ ID NO: 22  QERLQEDTSFGGNLGRAVFQAKKRILEPLGLVEEAAKTAPGKKRPVDQSP
AAV4  SEQ ID NO: 24  QQRLQGDTSFGGNLGRAVFQAKKRVLEPLGLVEQAGETAPGKKRPLIESP
AAV5  SEQ ID NO: 36  QEKLADDTSFGGNLGKAVFQAKKRVLEPFGLVEEGAKTAPTGKRIDDHFP
AAV6  SEQ ID NO: 26  QERLQEDTSFGGNLGRAVFQAKKRVLEPFGLVEEGAKTAPGKKRPVEQSP
AAV7  SEQ ID NO: 38  QERLQEDTSFGGNLGRAVFQAKKRVLEPLGLVEEGAKTAPAKKRPVEPSP
AAV8  SEQ ID NO: 40  QERLQEDTSFGGNLGRAVFQAKKRVLEPLGLVEEGAKTAPGKKRPVEPSP
AAV9  SEQ ID NO: 43  QERLKEDTSFGGNLGRAVFQAKKRVLEPLGLVEEPVKTAPGKKRPVEHSP
AAV10 SEQ ID NO: 41  QERLQEDTSFGGNLGRAVFQAKKRVLEPLGLVEEAAKTAPGKKRPVEPSP
AAV11 SEQ ID NO: 42  QERLQEDTSFGGNLGRAVFQAKKRVLEPLGLVEEGAKTAPGKKRP-LESP
                     *::* *********:*******:*** :***  :*** ** :*     *
         Prim.cons.  QERLQEDTSFGGNLGRAVFQAKKRVLEPLGLVEEGAKTAPGKKRPVE3SP
```

Fig. 1B

```
                            160       170       180       190       200
                             |         |         |         |         |
AAV2  SEQ ID NO: 13  V-EPDSSSGTGKAGQQPARKRLNFGQTGDADSVPDPQPLGQPPAAPSGLG
AAV1  SEQ ID NO: 20  Q-EPDSSSGIGKTGQQPAKKRLNFGQTGDSESVPDPQPLGEPPATPAAVG
AAV3  SEQ ID NO: 22  Q-EPDSSSGVGKSGKQPARKRLNFGQTGDSESVPDPQPLGEPPAAPTSLG
AAV4  SEQ ID NO: 24  Q-QPDSSTGIGKKGKQPAKKKLVFEDETGAGDGP---PEGSTSGAMS--D
AAV5  SEQ ID NO: 36  K--------RKKARTEEDSKPSTSSDAEAGPSGS-QQLQIPAQPASSLG
AAV6  SEQ ID NO: 26  Q-EPDSSSGIGKTGQQPAKKRLNFGQTGDSESVPDPQPLGEPPATPAAVG
AAV7  SEQ ID NO: 38  QRSPDSSTGIGKKGQQPARKRLNFGQTGDSESVPDPQPLGEPPAAPSSVG
AAV8  SEQ ID NO: 40  QRSPDSSTGIGKKGQQPARKRLNFGQTGDSESVPDPQPLGEPPAAPSGVG
AAV9  SEQ ID NO: 43  V-EPDSSSGTGKAGHQPARKRLNFGQTGDADSVPDPQPLGQPPAAPTSLG
AAV10 SEQ ID NO: 41  QRSPDSSTGIGKKGQQPAKKRLNFGQTGESESVPDPQPIGEPPAGPSGLG
AAV11 SEQ ID NO: 42  Q-EPDSSSGIGKKGKQPARKRLNFEEDTGAGDGP---PEGSDTSAMS--S
                             *  .:         .:    .  :               . :  .
        Prim.cons.   QREPDSSSGIGKKGQQPARKRLNFGQTGDSESVPDPQPLGEPPAAPSSLG 210       220       230       240       250
                             |         |         |         |         |
AAV2  SEQ ID NO: 13  TNTMATGSGAPMADNNEGADGVGNSSGNWHCDSTWMGDRVITTSTRTWAL
AAV1  SEQ ID NO: 20  PTTMASGGGAPMADNNEGADGVGNASGNWHCDSTWLGDRVITTSTRTWAL
AAV3  SEQ ID NO: 22  SNTMASGGGAPMADNNEGADGVGNSSGNWHCDSQWLGDRVITTSTRTWAL
AAV4  SEQ ID NO: 24  DSEMRAAAGGAAVEGGQGADGVGNASGDWHCDSTWSEGHVTTTSTRTWVL
AAV5  SEQ ID NO: 36  ADTMSAGGGGPLGDNNQGADGVGNASGDWHCDSTWMGDRVVTKSTRTWVL
AAV6  SEQ ID NO: 26  PTTMASGGGAPMADNNEGADGVGNASGNWHCDSTWLGDRVITTSTRTWAL
AAV7  SEQ ID NO: 38  SGTVAAGGGAPMADNNEGADGVGNASGNWHCDSTWLGDRVITTSTRTWAL
AAV8  SEQ ID NO: 40  PNTMAAGGGAPMADNNEGADGVGSSSGNWHCDSTWLGDRVITTSTRTWAL
AAV9  SEQ ID NO: 43  STTMATGSGAPMADNNEGADGVGNSSGNWHCDSQWLGDRVITTSTRTWAL
AAV10 SEQ ID NO: 41  SGTMAAGGGAPMADNNEGADGVGNASGNWHCDSTWLGDRVITTSTRTWAL
AAV11 SEQ ID NO: 42  DIEMRAAPGGNAVDAGQGSDGVGNASGDWHCDSTWSEGKVTTTSTRTWVL
                      : :. *.    :  .:*:****.:**:***** *  .:* *.*****.*
        Prim.cons.   S2TMAAGGGAPMADNNEGADGVGNASGNWHCDSTWLGDRVITTSTRTWAL 260       270       280       290       300
                             |         |         |         |         |
AAV2  SEQ ID NO: 13  PTYNNHLYKQISSQSGA--SNDNHYFGYSTPWGYFDFNRFHCHFSPRDWQ
AAV1  SEQ ID NO: 20  PTYNNHLYKQISSASTG-ASNDNHYFGYSTPWGYFDFNRFHCHFSPRDWQ
AAV3  SEQ ID NO: 22  PTYNNHLYKQISSQSGA--SNDNHYFGYSTPWGYFDFNRFHCHFSPRDWQ
AAV4  SEQ ID NO: 24  PTYNNHLYKRLGESLQ-----SNTYNGFSTPWGYFDFNRFHCHFSPRDWQ
AAV5  SEQ ID NO: 36  PSYNNHQYREIKSGSVD-GSNANAYFGYSTPWGYFDFNRFHSHWSPRDWQ
AAV6  SEQ ID NO: 26  PTYNNHLYKQISSASTG---NDNHYFGYSTPWGYFDFNRFHCHFSPRDWQ
AAV7  SEQ ID NO: 38  PTYNNHLYKQISSETAG-STNDNTYFGYSTPWGYFDFNRFHCHFSPRDWQ
AAV8  SEQ ID NO: 40  PTYNNHLYKQISNGTSGGATNDNTYFGYSTPWGYFDFNRFHCHFSPRDWQ
AAV9  SEQ ID NO: 43  PTYNNHLYKQISSQSG----NDNHYFGCSTPWGYFDFNRFHCHFSPRDWQ
AAV10 SEQ ID NO: 41  PTYNNHLYKQISNGTSGGSTNDNTYFGYSTPWGYFDFNRFHCHFSPRDWQ
AAV11 SEQ ID NO: 42  PTYNNHLYLRLGTTSS-----SNTYNGFSTPWGYFDFNRFHCHFSPRDWQ
                    *:**** *  .:           *  * *************.*:******
        Prim.cons.   PTYNNHLYKQISS2S2GG2SNDN2YFGYSTPWGYFDFNRFHCHFSPRDWQ
```

Fig. 1C

```
                           310       320       330       340       350
                            |         |         |         |         |
AAV2  SEQ ID NO: 13    RLINNNWGFRPKRLNFKLFNIQVKEVTQNDGTTTIANNLTSTVQVFTDSE
AAV1  SEQ ID NO: 20    RLINNNWGFRPKRLNFKLFNIQVKEVTTNDGVTTIANNLTSTVQVFSDSE
AAV3  SEQ ID NO: 22    RLINNNWGFRPKKLSFKLFNIQVKEVTQNDGTTTIANNLTSTVQVFTDSE
AAV4  SEQ ID NO: 24    RLINNWGMRPKAMRVKIFNIQVKEVTTSNGETTVANNLTSTVQIFADSS
AAV5  SEQ ID NO: 36    RLINNYWGFRPRSLRVKIFNIQVKEVTVQDSTTTIANNLTSTVQVFTDDD
AAV6  SEQ ID NO: 26    RLINNNWGFRPKRLNFKLFNIQVKEVTTNDGVTTIANNLTSTVQVFSDSE
AAV7  SEQ ID NO: 38    RLINNNWGFRPKKLRFKLFNIQVKEVTTNDGVTTIANNLTSTIQVFSDSE
AAV8  SEQ ID NO: 40    RLINNNWGFRPKRLSFKLFNIQVKEVTQNEGTKTIANNLTSTIQVFTDSE
AAV9  SEQ ID NO: 43    RLINNNWGFRPKRLNFKLFNIQVKEVTQNDGTTTIANNLTSTVQVFTDSE
AAV10 SEQ ID NO: 41    RLINNNWGFRPKRLSFKLFNIQVKEVTQNEGTKTIANNLTSTIQVFTDSE
AAV11 SEQ ID NO: 42    RLINNNWGLRPKAMRVKIFNIQVKEVTTSNGETTVANNLTSTVQIFADSS
                       ***** **:**: : .*:********* .:. .*:*******:*:*:*..

Prim.cons.    RLINNNWGFRPKRL2FKLFNIQVKEVT2NDGTTTIANNLTSTVQVFTDSE 360       370       380       390       400
                            |         |         |         |         |
AAV2  SEQ ID NO: 13    YQLPYVLGSAHQGCLPPFPADVFMVPQYGYLTLNNG---SQAVGRSSFYC
AAV1  SEQ ID NO: 20    YQLPYVLGSAHQGCLPPFPADVFMIPQYGYLTLNNG---SQAVGRSSFYC
AAV3  SEQ ID NO: 22    YQLPYVLGSAHQGCLPPFPADVFMVPQYGYLTLNNG---SQAVGRSSFYC
AAV4  SEQ ID NO: 24    YELPYVMDAGQEGSLPPFPNDVFMVPQYGYCGLVTGNTSQQQTDRNAFYC
AAV5  SEQ ID NO: 36    YQLPYVVGNGTEGCLPAFPPQVFTLPQYGYATLNRD-NTENPTERSSFFC
AAV6  SEQ ID NO: 26    YQLPYVLGSAHQGCLPPFPADVFMIPQYGYLTLNNG---SQAVGRSSFYC
AAV7  SEQ ID NO: 38    YQLPYVLGSAHQGCLPPFPADVFMIPQYGYLTLNNG---SQSVGRSSFYC
AAV8  SEQ ID NO: 40    YQLPYVLGSAHQGCLPPFPADVFMIPQYGYLTLNNG---SQAVGRSSFYC
AAV9  SEQ ID NO: 43    YPLPYVLGSAHQGCLPPFPADVFMVPQYGYLTLNNG---SQAVGRSSFYC
AAV10 SEQ ID NO: 41    YQLPYVLGSAHQGCLPPFPADVFMIPQYGYLTLNNG---SQAVGRSSFYC
AAV11 SEQ ID NO: 42    YELPYVMDAGQEGSLPPFPNDVFMVPQYGYCGIVTG-ENQNQTDRNAFYC
                       * ****:. . :*.**.** :** :*****   :   .: . *.:*:*

Prim.cons.    YQLPYVLGSAHQGCLPPFPADVFM2PQYGYLTLNNGN33SQAVGRSSFYC 410       420       430       440       450
                            |         |         |         |         |
AAV2  SEQ ID NO: 13    LEYFPSQMLRTGNNFTFSYTFEDVPFHSSYAHSQSLDRLMNPLIDQYLYY
AAV1  SEQ ID NO: 20    LEYFPSQMLRTGNNFTFSYTFEEVPFHSSYAHSQSLDRLMNPLIDQYLYY
AAV3  SEQ ID NO: 22    LEYFPSQMLRTGNNFQFSYTFEDVPFHSSYAHSQSLDRLMNPLIDQYLYY
AAV4  SEQ ID NO: 24    LEYFPSQMLRTGNNFEITYSFEKVPFHSMYAHSQSLDRLMNPLIDQYLWG
AAV5  SEQ ID NO: 36    LEYFPSKMLRTGNNFEFTYNFEEVPFHSSFAPSQNLFKLANPLVDQYLYR
AAV6  SEQ ID NO: 26    LEYFPSQMLRTGNNFTFSYTFEDVPFHSSYAHSQSLDRLMNPLIDQYLYY
AAV7  SEQ ID NO: 38    LEYFPSQMLRTGNNFEFSYSFEDVPFHSSYAHSQSLDRLMNPLIDQYLYY
AAV8  SEQ ID NO: 40    LEYFPSQMLRTGNNFQFTYTFEDVPFHSSYAHSQSLDRLMNPLIDQYLYY
AAV9  SEQ ID NO: 43    LEYFPSQMLRTGNNFTFSYTFEDVPFHSSYAHSQSLDRLMNPLIDQYLYY
AAV10 SEQ ID NO: 41    LEYFPSQMLRTGNNFEFSYTFEDVPFHSSYAHSQSLDRLMNPLIDQYLYY
AAV11 SEQ ID NO: 42    LEYFPSQMLRTGNNFEMAYNFEKVPFHSMYAHSQSLDRLMNPLLDQYLWH
                       ******:******** ::*.**.***** :* **.* :* ***:****:

Prim.cons.    LEYFPSQMLRTGNNFEFSYTFEDVPFHSSYAHSQSLDRLMNPLIDQYLYY
```

Fig. 1D

```
                            460        470        480        490        500
                             |          |          |          |          |
AAV2   SEQ ID NO: 13    LSRTN-TPSGTTTQSRLQFSQAGASDIRDQSRNWLPGPCYRQQRVSKTSA
AAV1   SEQ ID NO: 20    LNRTQ-NQSGSAQNKDLLFSRGSPAGMSVQPKNWLPGPCYRQQRVSKTKT
AAV3   SEQ ID NO: 22    LNRTQGTTSGTTNQSRLLFSQAGPQSMSLQARNWLPGPCYRQQRLSKTAN
AAV4   SEQ ID NO: 24    LQSTTTGTTLNAGTATTNFTKLRPTNFSNFKKNWLPGPSIKQQGFSKTAN
AAV5   SEQ ID NO: 36    FVSTN-------NTGGVQFNKNLAGRYANTYKNWFPGPMGRTQGWNLGSG
AAV6   SEQ ID NO: 26    LNRTQ-NQSGSAQNKDLLFSRGSPAGMSVQPKNWLPGPCYRQQRVSKTKT
AAV7   SEQ ID NO: 38    LARTQSNPGGTAGNRELQFYQGGPSTMAEQAKNWLPGPCFRQQRVSKTLD
AAV8   SEQ ID NO: 40    LSRTQTT-GGTANTQTLGFSQGGPNTMANQAKNWLPGPCYRQQRVSTTTG
AAV9   SEQ ID NO: 43    LNRTQ-SNSGTLQQSRLLFSQAGPTSMSLQAKNWLPGPCYRQQRLSKQAN
AAV10  SEQ ID NO: 41    LSRTQST-GGTQGTQQLLFSQAGPANMSAQAKNWLPGPCYRQQRVSTTLS
AAV11  SEQ ID NO: 42    LQSTTSGETLNQGNAATTFGKIRSGDFAFYRKNWLPGPCVKQQRFSKTAS
                         : *          *   :    .    :**:***  : *    .
            Prim.cons.  LNRTQST3SGTAG2SRLLFSQ2GPA5MSNQAKNWLPGPCYRQQRVSKTAN 510        520        530        540        550
                             |          |          |          |          |
AAV2   SEQ ID NO: 13    DN-----NNSEYSWTGATKYHLNGRDSLVNPGPAMASHKDDEEKFFPQSG
AAV1   SEQ ID NO: 20    DN-----NNSNFTWTGASKYNLNGRESIINPGTAMASHKDDEDKFFPMSG
AAV3   SEQ ID NO: 22    DN-----NNSNFPWTAASKYHLNGRDSLVNPGPAMASHKDDEEKFFPMHG
AAV4   SEQ ID NO: 24    QNYKIPATGSDSLIKYETHSTLDGRWSALTPGPPMATAGPADSKFS-NSQ
AAV5   SEQ ID NO: 36    VN-----RASVSAFATTNRMELEGASYQVPPQPNGMTNNLQGSNTYALEN
AAV6   SEQ ID NO: 26    DN-----NNSNFTWTGASKYNLNGRESIINPGTAMASHKDDKDKFFPMSG
AAV7   SEQ ID NO: 38    QN-----NNSNFAWTGATKYHLNGRNSLVNPGVAMATHKDDEDRFFPSSG
AAV8   SEQ ID NO: 40    QN-----NNSNFAWTAGTKYHLNGRNSLANPGIAMATHKDDEERFFPSNG
AAV9   SEQ ID NO: 43    DN-----NNSNFPWTAATKYHLNGRDSLVNPGPAMASHKDDEEKFFPMHG
AAV10  SEQ ID NO: 41    QN-----NNSNFAWTGATKYHLNGRDSLVNPGVAMATHKDDEERFFPSSG
AAV11  SEQ ID NO: 42    QNYKIPASGGNALLKYDTHYTLNNRWSNIAPGPPMATAGPSDGDFS-NAQ
                         *    .      .: *:.    *      :
            Prim.cons.  2NYKIPANNSNFAWTGATKYHLNGRDSLVNPGPAMATHKDDEEKFFPMSG 560        570        580        590        600
                             |          |          |          |          |
AAV2   SEQ ID NO: 13    VLIFGKQGSEKT---NVDIEKVMITDEEEIRTTNPVATEQYGSVSTNLQR
AAV1   SEQ ID NO: 20    VMIFGKESAGAS---NTALDNVMITDEEEIKATNPVATERFGTVAVNFQS
AAV3   SEQ ID NO: 22    NLIFGKEGTTAS---NAELDNVMITDEEEIRTTNPVATEQYGTVANNLQS
AAV4   SEQ ID NO: 24    LIFAGPKQNGNT---ATVPGTLIFTSEEELAATNATDTDMWGNLPGGDQS
AAV5   SEQ ID NO: 36    TMIFNSQPANPGTTATYLEGNMLITSESETQPVNRVAYNVGGQMATNNQS
AAV6   SEQ ID NO: 26    VMIFGKESAGAS---NTALDNVMITDEEEIKATNPVATERFGTVAVNLQS
AAV7   SEQ ID NO: 38    VLIFGKTGATN----KTTLENVLMTNEEEIRPTNPVATEEYGIVSSNLQA
AAV8   SEQ ID NO: 40    ILIFGKQNAARD---NADYSDVMLTSEEEIKTTNPVATEEYGIVADNLQQ
AAV9   SEQ ID NO: 43    TLIFGKQGTNAN---DADLEHVMITDEEEIRTTNPVATEQYGNVSNNLQN
AAV10  SEQ ID NO: 41    VLMFGKQGAGRD---NVDYSSVMLTSEEEIKTTNPVATEQYGVVADNLQQ
AAV11  SEQ ID NO: 42    LIFPGPSVTGNT---TTSANNLLFTSEEEIAATNPRDTDMFGQIADNNQN
                        ::  .            :::*.*.*  ..*    : * :. . *
            Prim.cons.  VLIFGKQGAGA2TTANTDL2NVMIT2EEEI2TTNPVATEQYGTVADNLQS
```

Fig. 1E

```
                                    610        620        630        640        650
                                     |          |          |          |          |
AAV2   SEQ ID NO: 13    GNRQAATADVNTQGVLPGMVWQDRDVYLQGPIWAKIPHTDGHFHPSPLMG
AAV1   SEQ ID NO: 20    SSTDPATGDVHAMGALPGMVWQDRDVYLQGPIWAKIPHTDGHFHPSPLMG
AAV3   SEQ ID NO: 22    SNTAPTTRTVNDQGALPGMVWQDRDVYLQGPIWAKIPHTDGHFHPSPLMG
AAV4   SEQ ID NO: 24    NSNLPTVDRLTALGAVPGMVWQNRDIYYQGPIWAKIPHTDGHFHPSPLIG
AAV5   SEQ ID NO: 36    STTAPATGTYNLQEIVPGSVWMERDVYLQGPIWAKIPETGAHFHPSPAMG
AAV6   SEQ ID NO: 26    SSTDPATGDVHVMGALPGMVWQDRDVYLQGPIWAKIPHTDGHFHPSPLMG
AAV7   SEQ ID NO: 38    ANTAAQTQVVNNQGALPGMVWQNRDVYLQGPIWAKIPHTDGNFHPSPLMG
AAV8   SEQ ID NO: 40    QNTAPQIGTVNSQGALPGMVWQNRDVYLQGPIWAKIPHTDGNFHPSPLMG
AAV9   SEQ ID NO: 43    SNTGPTTENVNHQGALPGMVWQDRDVYLQGPIWAKIPHTDGHFHPSPLMG
AAV10  SEQ ID NO: 41    ANTGPIVGNVNSQGALPGMVWQNRDVYLQGPIWAKIPHTDGNFHPSPLMG
AAV11  SEQ ID NO: 42    ATTAPITGNVTAMGVLPGMVWQNRDIYYQGPIWAKIPHADGHFHPSPLIG
                        . .             :** ** :**:* *********.:...:***** :*
            Prim.cons.  SNTAPATG3VNAQGALPGMVWQ2RDVYLQGPIWAKIPHTDGHFHPSPLMG 660        670        680        690        700
                                     |          |          |          |          |
AAV2   SEQ ID NO: 13    GFGLKHPPPQILIKNTPVPANPSTTFSAAKFASFITQYSTGQVSVEIEWE
AAV1   SEQ ID NO: 20    GFGLKNPPPQILIKNTPVPANPPAEFSATKFASFITQYSTGQVSVEIEWE
AAV3   SEQ ID NO: 22    GFGLKHPPPQIMIKNTPVPANPPTTFSPAKFASFITQYSTGQVSVEIEWE
AAV4   SEQ ID NO: 24    GFGLKHPPPQIFIKNTPVPANPATTFSSTPVNSFITQYSTGQVSVQIDWE
AAV5   SEQ ID NO: 36    GFGLKHPPPMMLIKNTPVPGN-ITSFSDVPVSSFITQYSTGQVTVEMEWE
AAV6   SEQ ID NO: 26    GFGLKHPPPQILIKNTPVPANPPAEFSATKFASFITQYSTGQVSVEIEWE
AAV7   SEQ ID NO: 38    GFGLKHPPPQILIKNTPVPANPPEVFTPAKFASFITQYSTGQVSVEIEWE
AAV8   SEQ ID NO: 40    GFGLKHPPPQILIKNTPVPADPPTTFNQSKLNSFITQYSTGQVSVEIEWE
AAV9   SEQ ID NO: 43    GFGLKHPPPQIMIKNTPVPANPPTNFSSAKFASFITQYSTGQVSVEIEWE
AAV10  SEQ ID NO: 41    GFGLKHPPPQILIKNTPVPADPPTTFSQAKLASFITQYSTGQVSVEIEWE
AAV11  SEQ ID NO: 42    GFGLKHPPPQIFIKNTPVPANPATTFTAARVDSFITQYSTGQVAVQIEWE
                        *****:*** ::*******.:    *.   . ***********:*:::**
            Prim.cons.  GFGLKHPPPQILIKNTPVPANPPTTFSAAKFASFITQYSTGQVSVEIEWE 710        720        730        740        750
                                     |          |          |          |          |
AAV2   SEQ ID NO: 13    LQKENSKRWNPEIQYTSNYNKSVNVDFTVDTNGVYSEPRPIGTRYLTRNL
AAV1   SEQ ID NO: 20    LQKENSKRWNPEVQYTSNYAKSANVDFTVDNNGLYTEPRPIGTRYLTRPL
AAV3   SEQ ID NO: 22    LQKENSKRWNPEIQYTSNYNKSVNVDFTVDTNGVYSEPRPIGTRYLTRNL
AAV4   SEQ ID NO: 24    IQKERSKRWNPEVQFTSNYGQQNSLLWAPDAAGKYTEPRAIGTRYLTHHL
AAV5   SEQ ID NO: 36    LKKENSKRWNPEIQYTNNYNDPQFVDFAPDSTGEYRTTRPIGTRYLTRPL
AAV6   SEQ ID NO: 26    LQKENSKRWNPEVQYTSNYAKSANVDFTVDNNGLYTEPRPIGTRYLWL--
AAV7   SEQ ID NO: 38    LQKENSKRWNPEIQYTSNFEKQTGVDFAVDSQGVYSEPRPIGTRYLTRNL
AAV8   SEQ ID NO: 40    LQKENSKRWNPEIQYTSNYYKSTSVDFAVNTEGVYSEPRPIGTRYLTRNL
AAV9   SEQ ID NO: 43    LQKENSKRWNPEIQYTSNYNKSVNVDFTVDTNGVYSEPCPIGTRYLTRNL
AAV10  SEQ ID NO: 41    LQKENSKRWNPEIQYTSNYYKSTNVDFAVNTEGTYSEPRPIGTRYLTRNL
AAV11  SEQ ID NO: 42    IEKERSKRWNPEVQFTSNYGNQSSMLWAPDTTGKYTEPRVIGSRYLTNHL
                        ::**.*******:*:*.*:    : ::  :   *  *   **:***
            Prim.cons.  LQKENSKRWNPEIQYTSNYNKS2NVDFAVDTNGVYSEPRPIGTRYLTRNL
```

Figure 2

AAV amino acid alignment

| | | | | | | | | | | | |
|---|---|---|---|---|---|---|---|---|---|---|---|
| AAV2 capsid sequence | 584 | Q | R | ▼ | N | R | Q | A | A | T | A | D | V | SEQ ID NO: 46 |
| AAV1 capsid sequence | 585 | Q | S | ▽ | S | T | D | P | A | T | G | D | V | SEQ ID NO: 47 |
| AAV3 capsid sequence | 585 | Q | S | ▽ | S | N | T | A | P | A | T | R | V | SEQ ID NO: 48 |
| AAV4 capsid sequence | 583 | Q | N | ▽ | N | ▼ | L | P | T | V | D | R | L | SEQ ID NO: 49 |
| AAV5 capsid sequence | 574 | Q | S | ▽ | S | T | A | P | A | T | G | T | Y | SEQ ID NO: 50 |

▼ Successful insertions within the AAV2 capsid protein (from previous work)

▽ Sites chosen for insertion within the other AAV capsid proteins

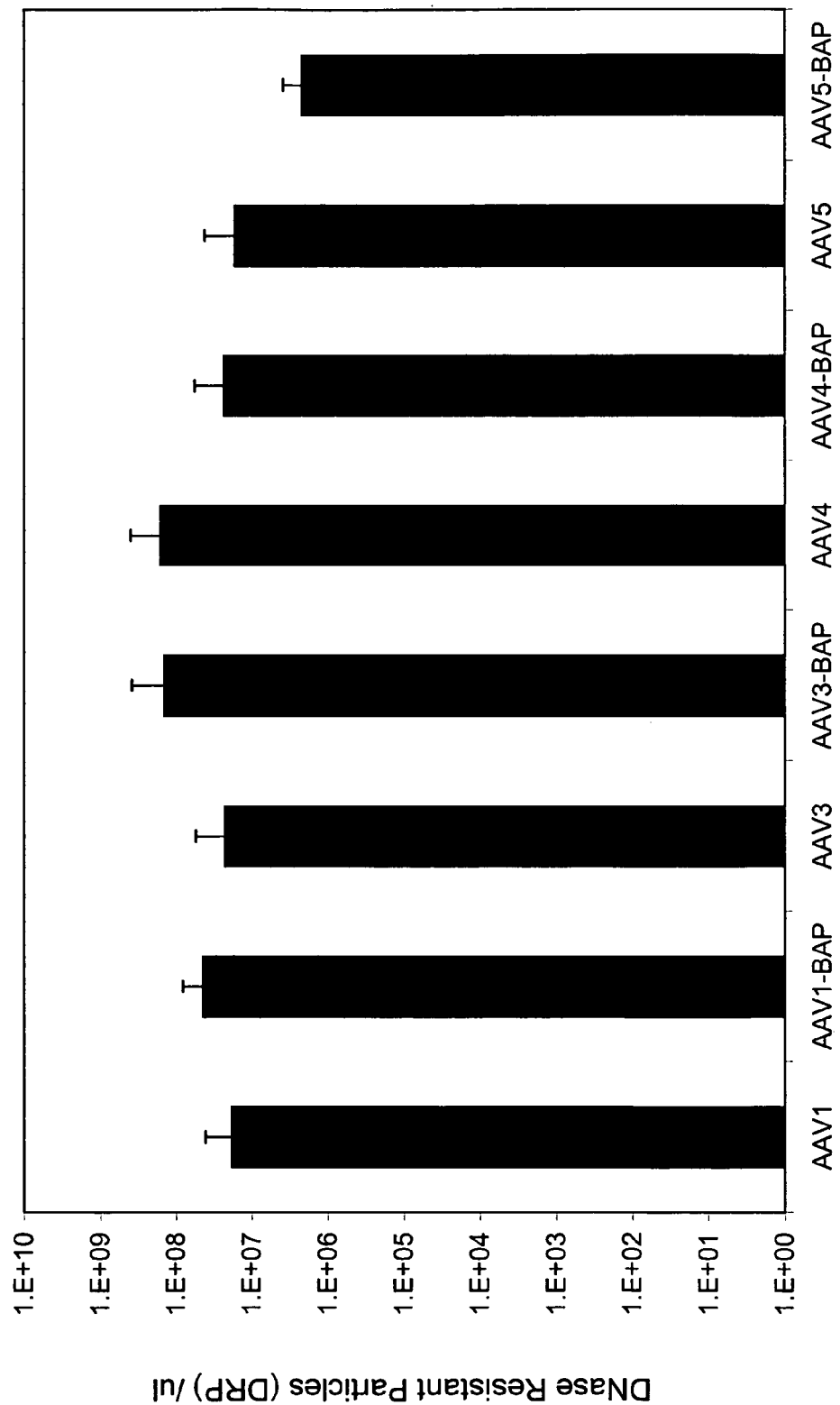
Figure 3 - DRP Titers of AAV1 - AAV5 BAP Mutants

US 7,749,492 B2

AAV VECTORS AND METHODS

RELATED APPLICATIONS

The present application is a continuation-in-part of U.S. patent application Ser. No. 10/038,972, filed Jan. 4, 2002, now U.S. Pat. No. 6,962,815, which claims priority benefit of U.S. Provisional Application No. 60/260,124 filed Jan. 5, 2001. These applications are incorporated herein by reference in their entirety.

FIELD OF THE INVENTION

The invention relates to Adeno-associated virus vectors. In particular, it relates to Adeno-associated virus vectors with modified capsid proteins and materials and methods for their preparation and use.

BACKGROUND

Adeno-associated virus (AAV) is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., *J. Virol.*, 45: 555-564 (1983) as corrected by Ruffing et al., *J. Gen. Virol.*, 75: 3385-3392 (1994). Cis-acting sequences directing viral DNA replication (rep), encapsidation/packaging and host cell chromosome integration are contained within the ITRs. Three AAV promoters, p5, p19, and p40 (named for their relative map locations), drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties which are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

When AAV infects a human cell, the viral genome can integrate into chromosome 19 resulting in latent infection of the cell. Production of infectious virus does not occur unless the cell is infected with a helper virus (for example, adenovirus or herpesvirus). In the case of adenovirus, genes E1A, E1B, E2A, E4 and VA provide helper functions. Upon infection with a helper virus, the AAV provirus is rescued and amplified, and both AAV and adenovirus are produced.

AAV possesses unique features that make it attractive as a vaccine vector for expressing immunogenic peptides/polypeptides and as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Replication of the viral DNA is not required for integration, and thus helper virus is not required for this process. The AAV proviral genome is infectious as cloned DNA in plasmids which makes construction of recombinant genomes feasible. Furthermore, because the signals, directing AAV replication, genome encapsidation, and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56□ to 65□C for several hours), making cold preservation of rAAV-vectors less critical. AAV may even be lyophilized. Finally, AAV-infected cells are not resistant to superinfection.

Recent research on AAV has therefore involved attempts to modify the viral genome. As the range of cells that AAV will infect is so broad, some researches have focused on modifying the virus so that it targets specific types of cells for infection. The cellular range or tropism of the virus is determined by the binding of AAV capsid protein(s) to receptor and/or coreceptor proteins expressed on the surface of target cells. Heparin-sulfate proteoglycan (HSPG) is the primary cellular attachment receptor for AAV2. In attempts to enable AAV to bind other cellular receptors, mutagenesis of the AAV capsid-encoding DNA to encode heterologous targeting peptides as part of a capsid protein has produced varying results. For example, Girod et al. (*Nature Medicine*, 5: 1052-1056, 1999) describes AAV2 insertional mutants generated to target L14-specific integrin receptors. These mutant AAV2 vectors expressed capsid proteins which had a fourteen amino acid peptide comprising the RGD domain of the laminin fragment P1 inserted at six different sites. Rabinowitz et al. (*Virology*, 265: 274-285, 1999) attempted to identify capsid domains and positions which were capable of tolerating insertions without loss of function. Related PCT application WO 00/28004 describes the modified capsid proteins containing insertions such as melanocyte stimulating hormone, polyhistidine tracts, poly-lysine tracts, an RGD domain and bradykinin. Only a few of the modified capsid proteins could be incorporated into functional viral particles and titers of the viruses were drastically lower than wild-type virus.

SUMMARY OF THE INVENTION

The present inventors recognized a need in the art for identification of sites in the AAV capsid protein(s) from which peptides/polypeptides of interest may be presented in a desired conformation to allow the development of AAV vectors that deliver DNA to specific target cells and the development of AAV vectors that present/display on their surface immunogenic peptides/polypeptides. Their invention is based on the elucidation of sites/regions in the AAV2 capsid protein that are amenable to insertion of heterologous peptides, the development of scaffolding sequences required for proper conformation of peptides, and the construction of AAV2 vectors with altered tropism.

The full length nucleotide sequence of the wild type AAV2 vector is set out as SEQ ID NO: 12. The amino acid sequence of VP1 capsid protein (SEQ ID NO: 13) is encoded by the nucleotides 2203-4410 of SEQ ID NO: 12, the amino acid sequence of VP2 capsid protein (SEQ ID NO: 14) is encoded by nucleotides 2614-4410 of SEQ ID NO: 12 and the amino acid sequence of VP3 capsid protein (SEQ ID NO: 15) is encoded by nucleotides 2809-4410 of SEQ ID NO: 12.

The full length nucleotide sequence of the wild type AAV1 vector is set out as SEQ ID NO: 19. The amino acid sequence of VP1 capsid protein (SEQ ID NO: 20) is encoded by nucleotides 2222-4433 of SEQ ID NO: 19.

The full length nucleotide sequence of the wild type AAV3 vector is set out as SEQ ID NO: 21. The amino acid sequence of VP1 capsid protein (SEQ ID NO: 22) is encoded by nucleotides 2208-4418 of SEQ ID NO: 21.

The full length nucleotide sequence of the wild type AAV4 vector is set out as SEQ ID NO: 23. The amino acid sequence of VP1 capsid protein (SEQ ID NO: 24) is encoded by nucleotides 2260-4464 of SEQ ID NO: 23.

The full length nucleotide sequence of the wild type AAV5 vector is set out as SEQ ID NO: 35. The amino acid sequence of VP1 capsid protein (SEQ ID NO: 36) is encoded by nucleotides 2207-4381 of SEQ ID NO: 35.

The full length nucleotide sequence of the wild type AAV6 vector is set out as SEQ ID NO: 25. The amino acid sequence of VP1 capsid protein (SEQ ID NO: 26) is encoded by nucleotides 2208-4418 of SEQ ID NO: 25.

The full length nucleotide sequence of the wild type AAV7 vector is set out as SEQ ID NO: 37. The amino acid sequence of VP1 capsid protein (SEQ ID NO: 38) is encoded by, nucleotides 2222-4435 of SEQ ID NO: 37.

The full length nucleotide sequence of the wild type AAV8 vector is set out as SEQ ID NO: 39. The amino acid sequence of VP1 capsid protein (SEQ ID NO: 40) is encoded by nucleotides of SEQ ID NO: 39.

In addition, the amino acid sequence of AAV9 VP1 capsid protein is set out as SEQ ID NO: 43. The amino acid sequence of AAV10 VP1 capsid protein is set out as SEQ ID NO: 41. The amino acid sequence of AAV11 VP1 capsid protein is set out as SEQ ID NO: 42.

The present invention provides AAV vectors (viral particles) encoding capsid proteins that comprise insertions of amino acids of interest (i.e., peptides or polypeptides). Preferably, the AAV vectors are AAV2 or AAV1 vectors. Also preferably, DNA encoding the insertions follows the cap gene DNA encoding amino acid position 139 and/or position 161 in the VP1/VP2 capsid region, and/or amino acid position 459, 584, 588 and/or 657 in the VP3 region.

While the capsid sites/regions amenable to insertions have been described herein with respect to AAV2, those skilled in the art will understand that corresponding sites in other parvoviruses, both autonomously-replicating parvoviruses, such as AAV1, AAV2, AAV3, AAV4, AAV5, AAV6, AAV7, AAV8, AAV9, AAV9, AAV10 and AAV11, and other AAV dependent viruses, are also sites/regions amenable to insertions in those viruses. These corresponding sites will tolerate insertions such that insertions at these sites do not affect infectability or viral particle formation of the parvovirus.

The corresponding sites may be determined by alignment of the primary amino acid sequence of the capsid proteins of various parvoviruses, such as the alignment of the capsid protein of various AAV serotypes set out in FIG. 1. An alignment of the primary amino acid sequence of the capsid proteins of parvoviruses allows for the determination of corresponding insertion sites because the three-dimensional secondary protein structure of parvoviruses and in particular AAV serotypes are very similar. Corresponding sites are those amino acid residues that align in an alignment. For example, a preferred insertion site in the VP3 region of the AAV2 capsid protein is position 585 of AAV2. Corresponding sites to position 585 of AAV2 are position 586 of AAV1 VP3, position 586 of AAV3 VP3, position 586 of AAV4 VP3 and position 586 of AAV5 VP3. Another preferred insertion site in the VP1 region of AAV2 is position 588, and the corresponding site in AAV1 VP1 is position 590.

The amino acids of interest may impart a different binding/targeting ability to the vector or may themselves be immunogenic. As a result, the vectors of the invention exhibit altered characteristics in comparison to wild type AAV, including but not limited to, altered cellular tropism and/or antigenic properties. The invention also contemplates cells, plasmids and viruses which comprise polynucleotides encoding the capsid proteins of the invention.

It is contemplated that in addition to amino acids of interest, amino acids serving as linker/scaffolding sequences as described herein may be included in the AAV vector capsid insert to maintain the functional conformation of the capsid. The linker/scaffolding sequences are short sequences which flank the insertion of interest in the mutated capsid protein. For example, the insertion may have the amino acids TG at its amino terminus and the tripeptide ALS, GLS or LLA at its carboxy terminus.

Techniques to produce AAV vectors, in which a AAV genome to be packaged, rep and cap genes, and helper virus functions are provided to a cell are standard in the art. Production of AAV vectors requires that the following components are present within a single cell (denoted herein as a packaging cell): a rAAV construct consisting of a DNA of interest flanked by AAV inverted terminal repeats, an AAV helper construct containing the capsid gene (which may or may not be comprise an insert) and the rep gene, and an adenovirus helper plasmid or infected with an adenovirus. The rAAV construct may be delivered to a packaging cell by transfection in a plasmid, infection by a viral genome or may be integrated into the packaging cell genome. The AAV helper construct may be delivered to a packaging cell by transfection of a plasmid or integrated into the packaging cell genome. The adenovirus helper plasmid or adenovirus may be delivered to the packaging cell by transfection/infection. The term "helper virus functions" refers to the functions carried out by the addition of an adenovirus helper plasmid or infection of adenovirus to support production of AAV viral particles.

One method generating a packaging cell with all the necessary components for AAV production is the triple transfection method. In this method a cell such as a 293 cell is transfected with the rAAV construct, the AAV helper construct and a adenovirus helper plasmid or infected with adenovirus. The advantages of the triple transfection method are that it is easily adaptable and straightforward. Generally, this method is used for small scale vector preparations.

Another method of generating a packaging cell is to create a cell line which stably expresses all the necessary components for AAV vector production. For example, a plasmid expressing the rAAV construct, a helper construct expressing the rep and cap proteins (modified or wild type) and a selectable marker, such as Neo, are integrated into the genome of a cell. The packaging cell line is then infected with a helper virus such as adenovirus. The advantages of this method are that the cells are selectable and are suitable for large-scale production of the vector.

In another aspect the invention provides AAV helper constructs encoding a AAV cap gene comprising DNA encoding an insertion of one or more amino acids in the encoded capsid protein(s). The insertion is at a position of the encoded capsid protein(s) that is exposed on the surface of an AAV vector comprising the capsid protein(s) and that does not disrupt conformation of the capsid protein(s) in a manner that prevents assembly of the vector or infectivity of the vector. Limited by these criteria, the size of the insert may vary from as short as two amino acids to as long as amino acids encoding an entire protein. Also provided are cells that stably or transiently produce AAV vectors of the invention. Methods of producing AAV vectors using such cells are contemplated by the invention.

In one embodiment, the AAV vectors of the invention comprising capsid proteins with binding/targeting amino acids inserted are useful for the therapeutic delivery and/or transfer of nucleic acids to animal (including human) cells both in vitro and in vivo. Nucleic acids of interest include nucleic acids encoding peptides and polypeptides, such as therapeutic (e.g., for medical or veterinary uses) peptides or polypeptides. A therapeutic peptide or polypeptide is one that may prevent or reduce symptoms that result from an absence or defect in a protein in a cell or person. Alternatively, a therapeutic peptide or polypeptide is one that otherwise confers a benefit to a subject, e.g., anti-cancer effects. As a further alternative, the nucleic acid may encode a reporter peptide or protein (e.g., an enzyme). In yet still another alternative, the nucleic acid of interest may be an antisense nucleic acid or a ribozyme.

In another embodiment, the AAV vectors are useful as vaccines. The use of parvoviruses as vaccines is known in the art. Immunogenic amino acids (peptides or polypeptides) may be presented as inserts in the AAV vector capsid. Alternatively, immunogenic amino acids may be expressed from a heterologous nucleic acid introduced into a recombinant AAV genome and carried by the AAV vector. If the immunogenic amino acids are expressed from a recombinant AAV genome, the AAV vector of the invention preferably exhibits an altered cellular tropism and comprises a capsid protein with an insertion of targeting amino acids that are different from those of wild type AAV. Immunogenic amino acids may be from any source (e.g., bacterial, viral or tumor antigens).

AAV vectors of the invention that exhibit an altered cellular tropism may differ from wild type in that the natural tropism of AAV may be reduced or abolished by insertion or substitution of amino acids of interest in a capsid protein of the vector. Alternatively, the insertion or substitution of the amino acids may target the vector to a particular cell type(s) perhaps not targeted by wild type AAV. Cell types of interest contemplated by the invention include, for example, glial cells, airway epithelial cells, hematopoietic progenitors cells and other stem cells, tumor cells and endothelial cells. In preferred embodiments, capsid amino acids are modified to remove wild type tropism and to introduce a new tropism. The inserted or substituted amino acid may comprise targeting peptides and polypeptides that are ligands and other peptides that bind to cell surface receptors and glycoproteins as well as fragments thereof that retain the ability to target vectors to cells. The targeting peptide or polypeptide may be any type of antibody or antigen-binding fragment thereof that recognizes, e.g., a cell-surface epitope. The binding domain from a toxin can be used to target the AAV vector to particular target cells of interest. It is also contemplated that AAV vectors of the invention may be targeted to a cell using a "nonclassical" import/export signal peptide (e.g., fibroblast growth factor-1 and -2, interleukin 1, HIV-1 Tat protein, herpes virus VP22 protein, and the like).

Also contemplated as targeting peptides are peptides that direct uptake of the AAV vector by specific cells. For example, a FVFLP peptide (SEQ ID NO: 18) triggers uptake by liver cells. Another peptide contemplated to direct uptake by cancer cells is the RGD peptide, e.g., 4C-RGD. The RGD domain is known to mediate interactions between extracellular matrix proteins and integrin receptors located on the surface of cancer cells. It is contemplated that the insertion of an RGD peptide into the capsid of the AAV vector will act as a cell entry mechanism specific to cancer cells. The receptor-binding peptide from luteinizing hormone is also contemplated as a peptide which when inserted into the capsid of an AAV vector will direct entry into ovarian cells since ovarian cells express luteinizing hormone receptors.

The invention also contemplates targeting peptides specific for cells within the vasculature, such as peptides that bind to proteins expressed on vascular endothelial cells or vascular smooth muscle cells. Many diseases such as cancer and forms of cardiovascular disease, share a common process of vascular proliferation. It is thought that the ability to deliver and express genes in the vasculature will be valuable for the development of gene therapies aimed at these diseases. While AAV vectors can transduce a wide variety of cell types, certain cells (including cells of the vascular system) remain refractive to AAV transduction. Peptides targeted towards receptors or other proteins expressed on the vasculature incorporated into the capsids of AAV vectors, as described herein, are potential mechanisms for delivering genes to the vasculature. These peptides include peptides that target vascular endothelial growth factor receptor 2 (VEGFR2), peptides that target the Tie2 receptor, peptides homologous to the N-terminal fragment of human high mobility group protein 2 (HMGN2), and peptides that targeted integrin receptors. Insertion of these targeting peptides into the capsids of AAV vectors can increase the viruses ability to transduce endothelial cells in vitro and in vivo. AAV vectors which target the endothelial cells are potential therapeutic vectors for ischemia, vascular proliferation, and angiogenesis.

Other targeting peptide contemplated influence cellular trafficking of viral particles. Phage display techniques, as well as other techniques known in the art, may be used to identify peptides that recognize, preferably specifically, a cell type of interest. Alternatively, the targeting sequence comprises amino acids that may be used for chemical coupling (e.g., through amino acid side groups of arginine or lysine residues) of the capsid to another molecule that directs entry of the AAV vector into a cell.

The present invention also encompasses modified AAV vectors, the capsid protein(s) of which are biotinylated in vivo. For example, the invention contemplates AAV capsids engineered to include the biotin acceptor peptide (BAP). Expression of the E. coli enzyme biotin protein ligase during AAV vector biosynthesis in the presence of biotin results in biotinylation of the AAV capsid proteins as they are made and assembled into viral particles.

In order to biotinylate the AAV viral particles, a system for expressing the biotin ligase enzyme in packaging cell lines is contemplated by the present invention. The invention provides for plasmids, such as the pCMV plasmid, which direct expression of the biotin ligase gene within the packaging cell line. For production of the biotinylated AAV vector the following components need to be transfected into a packaging cell: a rAAV vector comprising DNA of interest flanked by AAV inverted terminal repeats, an AAV helper construct containing a capsid gene with a BAP insert and the rep gene, adenovirus helper plasmid or infected with adenovirus, and the biotin ligase gene (BirA). In this system, the biotin ligase gene may be expressed by a plasmid including the BirA gene (such as pCMV-BirA) infection with an adenovirus which expresses the BirA gene or by using a packaging cell line that is stably transfected with the BirA gene.

It is contemplated that the biotinylated AAV viral particles will serve as substrates for conjugation of targeting motifs (e.g., monoclonal antibodies, growth factors, cytokines) to the surface of vector particles through utilizing avidin/strepavidin-biotin chemistry. In addition, the biotinylated AAV viral particles are contemplated to be useful for visualizing the biodistribution of the viral particles both in vivo and in vitro. The biotinylated viral particles can be visualized with fluorescence or enzymatically with labeled strepavidin compounds. Biotinylation is also useful for conjugating epitope shielding moieties, such as polyethylene glycol, to the AAV vector. The conjugation of shielding moieties allows the vector to evade immune recognition. Biotinylation of the AAV vector is also contemplated to enhance intracellular trafficking of viral particles through conjugation of proteins or peptides such as nuclear transport proteins. Biotinylation may also be used to conjugate proteins or peptides which affect the processing of AAV vector genomes such as increasing the efficiency of integration. In addition, biotinylation may also be used to conjugate proteins or peptides that affect the target cells, e.g., proteins that make a target cell more susceptible to infection or proteins that activate a target cell thereby making it a better target for the expression of a therapeutic or antigenic peptide. In addition, the incorporation of biotin acceptor peptide (BAP) into the AAV capsid proteins may also be used to purify modified vectors of the invention.

The present invention also provides compositions comprising an AAV vector of the invention in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Methods of eliciting an immune response to amino acids of interest are contemplated by the invention. The methods comprise a step of administering an immunogenic dose of a composition comprising a AAV vector of the invention to a animal (including a human person) in need thereof. In the methods, the immunogenic amino acids may be inserted in the AAV vector capsid protein(s) or may be encoded by a recombinant genome encapsidated as the AAV vector. An immunogenic dose of a composition of the invention is one that generates, after administration, a detectable humoral and/or cellular immune response in comparison to the immune response detectable before administration or in comparison to a standard immune response before administration. The invention contemplates that the immune response resulting from the methods may be protective and/or therapeutic.

Therapeutic methods of delivering and/or transferring nucleic acids of interest to a host cell are also contemplated by the invention. The methods comprise the step of administering a therapeutically effective dose of a composition comprising a AAV vector of the invention to an animal (including a human person) in need thereof. A therapeutically effective dose is a dose sufficient to alleviate (eliminate or reduce) at least one symptom associated with the disease state being treated. Administration of the therapeutically effective dose of the compositions may be by routes standard in the art, for example, parenteral, intravenous, oral, buccal, nasal, pulmonary, rectal, or vaginal.

Titers of AAV vector to be administered in methods of the invention will vary depending, for example, on the particular virus vector, the mode of administration, the treatment goal, the individual, and the cell type(s) being targeted, and may be determined by methods standard in the art.

BRIEF DESCRIPTION OF DRAWING

FIGS. 1A-1E depict an alignment of the amino acid sequence of capsid proteins from various AAV serotypes.

FIG. 2 is an alignment of the primary amino acid sequence of a portion of AAV serotypes: AAV1, AAV2, AAV3, AAV4 and AAV5. ▼ mark the location of insertion in AAV2 capsid proteins, and ∇ mark the location of insertions described in Example 15. This figure provides examples of corresponding insertion sites in various AAV serotypes.

FIG. 3 depicts the that insertion of BAP did not significantly decrease viral particle production in any of the AAV vector serotypes tested when compared to the corresponding wild type vector serotypes.

DETAILED DESCRIPTION

The present invention is illustrated by the following examples that are not intended to limit the invention. Example 1 describes construction of AAV packaging plasmids encoding altered capsid proteins and analysis of the ability of the altered capsid proteins to be assembled into infectious AAV vectors. Example 2 presents assays for the surface expression of epitopes inserted in the altered capsid proteins. Example 3 describes experiments testing whether the AAV vectors retained HSPG-binding ability. Example 4 describes construction and characterization of a mutant AAV vector containing a double insertion within the capsid protein. Example 5 includes analysis of the effect of linker and scaffold sequences on the altered capsid proteins. Example 6 presents the results of experiments in which AAV vectors encoding capsid proteins with an insertion of an luteinizing hormone receptor binding peptide were able to transduce OVCAR-3 cells. Example 6 also discusses various indications amenable to use of AAV vectors of the invention. Example 7 and 8 describe fourteen additional modified AAV vectors, wherein the RGD-4C peptide motif was inserted into the capsid proteins. The experiments described in Example 9 demonstrate that the AAV-RGD vectors attach to and enter cells via integrin receptors. Example 10 demonstrates that the AAV-RGD vectors were capable of mediating gene delivery via integrin receptors. Example 11 demonstrates that the AAV-RGD vectors transferred genes to ovarian adenocarcinoma cell lines. Example 12 describes AAV mediated eGFP gene delivery to human ovarian tumor xenografts established in SCID mice. Example 13 describes construction of mutant AAV vectors which are biotinylated in vivo through an insertion of the biotin acceptor peptide in the capsid protein. Example 14 describes a packaging system for biotinylated AAV vectors. Example 15 describes experiments to determine corresponding insertion sites in the capsid proteins that do not affect infectablility or viral particle formation in various AAV serotypes. Finally, Example 16 describes construction of AAV1 and AAV2 vectors containing capsid proteins modified with vasculature targeting peptides.

Example 1

In order to identify sites within the AAV2 capsid that could tolerate insertion of targeting epitopes, an extensive site-specific mutagenesis strategy was designed. Regions of the AAV2 capsid DNA to be modified were chosen by analyzing data from a number of sources to predict which ones encoded capsid amino acids that were exposed on the surface of the virion and which encoded amino acids that could be replaced with other amino acids without significantly altering the conformation of the rest of the capsid protein(s). One source of data was a comparison of structural information from five related autonomous parvoviruses. The five parvoviruses had solved virion structures and included canine parvovirus (CPV) (Tsao et al., *Science,* 251: 1456-1464 and Wu et al., *J. Mol. Biol.,* 233: 231-244), feline panleukopenia virus (FPV) (Agbandje et al., *Proteins,* 16: 155-171), minute, virus of mice (MVM) (Agbandje-McKenna et al., *Structure,* 6: 1369-1381 and Llamas-Saiz et al., *Acta Crystallogr. Sect. D. BioL Crystallogr.,* 53: 93-102), parvovirus B19 (B19) (Chipman et al., *Proc. Natl. Acad. Sci. USA,* 93: 7502-7506) and Aleutian mink disease parvovirus (ADV) (McKenna et al., *J. Virol.,* 73: 6882-6891). This information was compared to a computer-predicted secondary structure of the AAV2 capsid based on its known primary amino acid sequence. Other sources of data were previous reports of immunogenic regions of the AAV2 capsid and previous reports of effects of random capsid mutations. Finally, the AAV2 capsid primary amino acid sequence was compared with that of other AAV and other parvoviridae for regions of defined secondary structure to create a model of the AAV2 capsid. From the model sites for insertion of small peptides two to fifteen amino acids in length were chosen. A series of thirty-eight virus mutants containing peptide insertions at twenty-five unique sites within the AAV2 capsid protein was generated. Most of the insertions were within the VP1 capsid protein (19/25), four were within the VP1 unique region and two were within the VP1/VP2 unique region. Epitopes inserted within the VP3 protein are expected to be displayed on every capsid monomer within the AAV virion (60/virion). Insertions within the VP1 or VP1/VP2 unique regions would be expected to be displayed three and six times, respectively, per virion.

Site-directed mutagenesis was performed on plasmid pUC-Cap (a subclone of the AAV2 Rep and Cap open reading frames (ORF)). Mutagenesis was confirmed by restriction endonuclease digestion. The altered Cap genes were then substituted for the wild-type AAV2 sequences in plasmid pACG2 to generate the series of mutant helper plasmids described in Table 1 below, wherein epitope AgeI is the amino acids encoded by an AgeI restriction site, epitope NgoMI is the amino acids encoded by an NgoMI restriction site, epitope 4C-RGD is a cyclic RGD-based peptide (CDCRGDCFC; SEQ ID NO: 10) that has been shown to bind a number of integrins, including $\alpha_v\beta_3$, $\alpha_v\beta_5$, $\alpha_5\beta_1$, $\alpha_5\beta_1$, $\alpha_3\beta_1$, $\alpha_2\beta_1$ and $\alpha_6\beta_1$, present on the surface of mammalian cells that is useful for targeting to tumor endothelium and other cell types, epitope BPV is a peptide from bovine papilloma virus (TPPYLK; SEQ ID NO: 16), and epitope LH is a receptor-binding peptide from luteinizing hormone (HCSTCYYHKS; SEQ ID NO: 17). Plasmid nomenclature in the Table 1 can be understood by reference to plasmid pACG-A139 wherein pACG refers to the starting plasmid in which mutant cap sequences were inserted and A139 refers to insertion of an AgeI restriction site after position 139 of the capsid, and by reference to plasmid pACG-A139BPV/GLS wherein BPV indicates the peptide of interest that is inserted and /GLS indicates inclusion of linker amino acids at the carboxy terminus of the inserted epitope.

TABLE 1

Mutant AAV Packaging Plasmids

| Mutant Plasmid Designation | Location | Insertion (epitope) |
|---|---|---|
| pACG-A26 | VP1 | TG (Age I) |
| pACG-A46 | VP1 | TG (Age I) |
| pACG-A115-4C-RGD/GLS | VP1 | TGCDCRGDCFCGLS (SEQ ID NO: 1) (4C-RGD) |
| pACG-A120 | VP1 | TG (Age I) |
| pACG-A139 | VP2 | TG (Age I) |
| pACG-A139BPV/GLS | VP2 | TGTPFYLKGLS (SEQ ID NO: 2) (BPV) |
| pACG-A139LH/GLS | VP2 | TGHCSTCYYHKSGLS (SEQ ID NO: 3) (LH) |
| pACG-A161BPV/ALS | VP2 | TGTPFYLKALS (SEQ ID NO: 4) (BPV) |
| pACG-A161BPV/LLA | VP2 | TGTPFYLKLLA (SEQ ID NO: 5) (BPV) |
| pACG-A161BPV/GLS | VP2 | TGTPFYLKGLS (SEQ ID NO: 2) (BPV) |
| pACG-A161LH/GLS | VP2 | TGHCSTCYYHKSGLS (SEQ ID NO: 3) (LH) |
| pACG-A312 | VP3 | TG (Age I) |
| pACG-N319 | VP3 | AG (NgoMI) |
| pACG-A323-4C-RGD/GLS | VP3 | TGCDCRGDCFCGLS (SEQ ID NO: 1) (4C-RGD) |
| pACG-A339BPV | VP3 | TGTPFYLK (SEQ ID NO: 6) (BPV |
| pACG-A375BPV | VP3 | TGTPFYLK (SEQ ID NO: 6) (BPV) |
| pACG-A441 | VP3 | TG (Age I) |
| pACG-A459 | VP3 | TG (Age I) |
| pACG-A459BPV/GLS | VP3 | TGTPFYLKGLS (SEQ ID NO: 2) (BPV) |
| pACG-A459LH/GLS | VP3 | TGHCSTCYYHKSGLS (SEQ ID NO: 3) (LH) |
| pACG-A466 | VP3 | TG (Age I) |
| pACG-A480-4C-RGD/GLS | VP3 | TGCDCRGDCFCGLS (SEQ ID NO: 1) (4C-RGD) |
| pACG-N496 | VP3 | AG (NgoMI) |
| pACG-A520LH/GLS | VP3 | TGHCSTCYYHKSGLS (SEQ ID NO: 3) (LH) |
| pACG-A520BPV/LLA | VP3 | TGTPFYLKLLA (SEQ ID NO: 5) (BPV) |
| pACG-A540 | VP3 | TG (Age I) |
| pACG-N549 | VP3 | AG (NgoMI) |
| pACG-N584 | VP3 | AG (NgoMI) |
| pACG-A584BPV/ALS | VP3 | TGTPFYLKALS (SEQ ID NO: 4) (BPV) |
| pACG-A584BPV/LLA | VP3 | TGTPFYLKLLA (SEQ ID NO: 5) (BPV) |

TABLE 1-continued

Mutant AAV Packaging Plasmids

| Mutant Plasmid Designation | Location | Insertion (epitope) |
|---|---|---|
| pACG-A584BPV/GLS | VP3 | TGTPFYLKGLS (SEQ ID NO: 2) (BPV) |
| pACG-N472 | VP3 | AG (NgoMI) |
| pACG-A587BPV/ALS | VP3 | TGTPFYLKALS (SEQ ID NO: 4) (BPV) |
| pACG-A587BPV/LLA | VP3 | TGTPFYLKLLA (SEQ ID NO: 5) (BPV) |
| pACG-A587BPV/GLS | VP3 | TGTPFYLKGLS (SEQ ID NO: 2) (BPV) |
| pACG-A595-4C-RGD/GLS | VP3 | TGCDCRGDCFCGLS (SEQ ID NO: 1) (4C-RGD) |
| pACG-A597-4C-RGD/GLS | VP3 | TGCDCRGDCFCGLS (SEQ ID NO: 1) (4C-RGD) |
| pACG-A657 | VP3 | TG (Age I) |

The mutant AAV packaging plasmids were tested for their ability to generate AAV vectors with altered capsids by triple transfection with plasmid pAAV-LacZ (a plasmid containing LacZ flanked by AAV ITRs) and pXX6-80 (a plasmid containing Adenovirus helper DNA) according to established procedures. AAV vector preparations were assessed for particle formation and vector infectivity. Particles were identified by ELISA using A20 monoclonal antibody, whereas DNA-containing particles were identified by dot-blot and/or PCR. Vector particles were tested for infectivity by cellular transduction assay on Adenovirus-infected C12 cells. Capsid mutants were grouped into three types. Capsid mutants that did not give rise to any viral particles were classified as Type I (7/38). Mutants that produced non-infectious particles were classified as Type II (11/38) and mutants that produced fully infectious viral particles were classified as Type III (20/38). See Table 2 below wherein the actual titers are listed as values for comparison with the wild type titer unless the titer (−) is four orders of magnitude or more less than wild type vector and a titer (+) is below the sensitivity of DNA dot blot but detectable by PCR.

TABLE 2

Mutant AAV Vector Characterization Particle titer

| Mutant Vector Designation | Dot-blot | A20 ELISA | Infections titer | Mutant Type |
|---|---|---|---|---|
| AAV-A26 | (+) | $7.5 \times 10^7$ | — | II |
| AAV-A46 | $9.2 \times 10^7$ | $8.0 \times 10^7$ | $1.2 \times 10^3$ | III |
| AAV-A115-4C-RGD/GLS | $5.6 \times 10^7$ | $7.5 \times 10^7$ | $1.2 \times 10^2$ | III |
| AAV-A120 | $3.4 \times 10^7$ | $8.0 \times 10^7$ | $1.0 \times 10^3$ | III |
| AAV-A139 | $2.0 \times 10^7$ | $9.0 \times 10^7$ | $5.0 \times 10^5$ | III |
| AAV-A139BPV/GLS | $1.4 \times 10^8$ | $9.0 \times 10^7$ | $6.8 \times 10^5$ | III |
| AAV-A139LH/GLS | $1.2 \times 10^8$ | $8.0 \times 10^7$ | $3.3 \times 10^5$ | III |
| AAV-A161BPV/ALS | $4.0 \times 10^7$ | $8.0 \times 10^7$ | $1.2 \times 10^5$ | III |
| AAV-A161BPV/LLA | $1.4 \times 10^6$ | $7.5 \times 10^5$ | $5.9 \times 10^2$ | III |
| AAV-A161BPV/GLS | $1.2 \times 10^7$ | $7.5 \times 10^6$ | $8.7 \times 10^4$ | III |
| AAV-A161LH/GLS | $4.0 \times 10^6$ | $8.0 \times 10^7$ | $3.4 \times 10^4$ | III |
| AAV-A312 | $1.8 \times 10^6$ | — | $5.3 \times 10^2$ | III |
| AAV-N319 | $2.4 \times 10^7$ | $4.5 \times 10^5$ | $0.6 \times 10^3$ | III |

TABLE 2-continued

Mutant AAV Vector Characterization Particle titer

| Mutant Vector Designation | Dot-blot | A20 ELISA | Infections titer | Mutant Type |
|---|---|---|---|---|
| AAV-A323-4C-RGD/GLS | (+) | — | — | I |
| AAV-A339BPV | (+) | — | — | II |
| AAV-A375BPV | — | — | — | I |
| AAV-A441 | — | — | — | I |
| AAV-A459 | $7.2 \times 10^6$ | $8.0 \times 10^7$ | $6.5 \times 10^4$ | III |
| AAV-A459BPV/GLS | $5.6 \times 10^7$ | $4.5 \times 10^6$ | $2.2 \times 10^5$ | III |
| AAV-A459LH/GLS | $3.2 \times 10^6$ | $4.5 \times 10^5$ | — | II |
| AAV-A466 | (+) | $7.5 \times 10^7$ | — | II |
| AAV-N472 | — | — | — | I |
| AAV-A480-4C-RGD/GLS | — | — | — | I |
| AAV-N496 | $2.2 \times 10^6$ | — | $1.1 \times 10^2$ | III |
| AAV-A520LH/GLS | (+) | $7.5 \times 10^7$ | — | II |
| AAV-A520BPV/LLA | (+) | $7.5 \times 10^7$ | — | II |
| AAV-N540 | (+) | $8.0 \times 10^7$ | — | II |
| AAV-N549 | (+) | $4.5 \times 10^6$ | — | II |
| AAV-N584 | $1.1 \times 10^8$ | $8.0 \times 10^7$ | $4.0 \times 10^5$ | III |
| AAV-A584BPV/ALS | $3.0 \times 10^7$ | $8.0 \times 10^7$ | $6.5 \times 10^2$ | III |
| AAV-A584BPV/LLA | $1.3 \times 10^7$ | $9.0 \times 10^6$ | — | II |
| AAV-A584BPV/GLS | (+) | $7.5 \times 10^5$ | — | II |
| AAV-A587BPV/ALS | $1.8 \times 10^7$ | $8.0 \times 10^6$ | $5.0 \times 10^1$ | III |
| AAV-A587BPV/LLA | $7.2 \times 10^5$ | $9.0 \times 10^5$ | — | II |
| AAV-A587BPV/GLS | $3.5 \times 10^7$ | $9.0 \times 10^7$ | $2.7 \times 10^2$ | III |
| AAV-A595-4C-RGD/GLS | — | $2.5 \times 10^4$ | — | I |
| AAV-A597-4C-RGD/GLS | — | $2.5 \times 10^4$ | — | I |
| AAV-A657 | $1.8 \times 10^7$ | $7.5 \times 10^7$ | $5.2 \times 10^4$ | III |
| AAV (wild-type) | $4.8 \times 10^7$ | $9.0 \times 10^7$ | $6.2 \times 10^5$ | N/A |

Of the sites chosen for linker insertion, 20 (80%) tolerated this manipulation as assessed by particle formation. Infectious virus could be produced containing linker insertions at twelve of the sites that were tolerated for viral assembly (12/20; 60%). This represents 48% of the sites originally selected for mutagenesis.

Although twelve sites within the AAV2 capsid protein(s) could be altered, and the mutant capsid monomers still assemble, package viral genomes, and infect cells, the infectious titers of these viruses varied greatly. These ranged from essentially wild-type levels to greater than four orders of magnitude less infectious than wild-type. Significantly, several sites could tolerate a wide range of genetic insertions without effects on virus titer. Both of the sites within the VP1/VP2 unique region of the capsid ORF proved able to tolerate genetic insertions without a loss in viral titer. See results for mutant vectors with insertions after amino acid positions A139 and A161. However, insertion after position A161 showed some dependence on surrounding sequence elements. See Example 5 below. Within the VP3 region of the capsid ORF, results were more variable. Although many insertions were tolerated with essentially no loss in vector titer (for example, after positions R459 and Q584), there was a greater dependence on linker sequences (compare AAV-N584BPV/ALS to AAV-N584BPV/LLA; also see Example 5, below) and the primary sequence of the epitope being inserted (compare AAV-A459BPV/GLS to AAV-A459LH/GLS).

Example 2

The surface accessibility of inserted BPV epitopes in the mutant AAV vectors described in Example 1 was examined by immunoprecipitation.

Iodixanol grandient-purified vectors were precipitated with anti-BPV monoclonal antibody using protein-G Sepharose, subjected to SDS-PAGE, blotted to nylon membranes and probed with anti-AAV B1 monoclonal antibody. A summary of epitope display for each BPV insertion mutant is shown in Table 3 below.

TABLE 3

Surface Display of Inserted BPV Epitopes

| Mutant Vector Designation | Epitope Display |
|---|---|
| AAV-A139BPV/GLS | + |
| AAV-A161BPV/ALS | + |
| AAV-A161BPV/LLA | + |
| AAV-A161BPV/GLS | + |
| AAV-A339BPV | − |
| AAV-A459BPV/GLS | + |
| AAV-A520BPV/LLA | + |
| AAV-A584BPV/ALS | + |
| AAV-A584BPV/LLA | + |
| AAV-A584BPV/GLS | − |
| AAV-A587BPV/ALS | + |
| AAV-A587BPV/LLA | − |
| AAV-A587BPV/GLS | + |

Inserted peptide epitopes could be displayed efficiently on the surface of viral particles at each site tested which were all sites that insertion gave rise to infectious vectors. However, display was often dependent on inclusion of appropriate linker/scaffolding sequences.

Example 3

The mutant AAV vectors of Example 1 were also tested for retention of the ability to bind HSPG.

The ability of the AAV vectors to bind HSPG was assessed by purifying the AAV preparations on an iodixanol gradient. The 40% iodixanol layer was collected and diluted in PBS-MK containing heparin sulfate affinity resin. The mixtures were incubated for two hours with gentle shaking at 4° C. followed by centrifugation. The viral bound resin was washed three times with PBS-MK for ten minutes at room temperature and resuspended in loading buffer. The samples were then boiled and analyzed by Western blotting with monoclonal antibody B1 directed against the AAV2 VP3 capsid protein. A summary of the HS-binding characteristic for all of the mutant is presented in Table 4 below.

TABLE 4

HSPG Binding

| Mutant Vector Designation | HSPG Binding |
|---|---|
| AAV-A26 | − |
| AAV-A46 | + |
| AAV-A115-4C-RGD/GLS | + |
| AAV-A139 | + |
| AAV-A139BPV/GLS | + |
| AAV-A139LH/GLS | + |
| AAV-A161BPV/ALS | + |
| AAV-A161LH/GLS | + |
| AAV-A312 | − |
| AAV-A323-4C-RGD/GLS | − |
| AAV-A375BPV | + |

TABLE 4-continued

HSPG Binding

| Mutant Vector Designation | HSPG Binding |
|---|---|
| AAV-A459 | + |
| AAV-A459LH/GLS | + |
| AAV-A466 | + |
| AAV-N472 | + |
| AAV-A480-4C-RGD/GLS | + |
| AAV-A520LH/GLS | − |
| AAV-A520BPV/LLA | − |
| AAV-A540 | + |
| AAV-N549 | − |
| AAV-A584BPV/ALS | + |
| AAV-A584BPV/LLA | + |
| AAV-A584BPV/GLS | − |
| AAV-A587BPV/ALS | + |
| AAV-A587BPV/LLA | + |
| AAV-A587BPV/GLS | + |
| AAV-A595-4C-RGD/GLS | + |
| AAV-A597-4C-RGD/GLS | + |
| AAV (wild-type) | + |

Some of the Type II mutants may have been non-infectious because they no longer bound HSPG (see the A26 or A520 mutants). These mutants are valuable because the endogenous tropism of the virus has been ablated and any binding capability added to the virus would be exclusive. In situations in which loss of receptor-binding ability as a result of introducing mutations at a specific capsid site is not desirable, the foregoing data demonstrates that binding can often be rescued by inclusion of appropriate flexible linker sequences.

Example 4

A mutant AAV2 vectors containing a peptide insertion at two different sites within the capsid protein was generated using the methods described herein. The 4C-RGD peptide (SEQ ID NO: 10) was inserted using site directed mutagenesis as described in Example 1 after amino acid position 520 and position 588 within the VP3 capsid protein. The double mutant AAV2 vector (denoted herein as A520RGD4C588RGD4C) was assessed for particle formation and vector infectivity. Particles were identified by ELISA using A20 monoclonal antibody, whereas DNA-containing particles were identified by dot-blot. Vector particles were tested for infectivity by cellular tranduction assay on Adenovirus-infected C12 cells. The double mutant was able to infect cells and produce viral particles at a similar rate as other mutant and wild-type vectors. In Table 5, infectivity is presented as the percentage of target cells expressing the vector-encoded transgene and particle titer is presented as particles/μl.

TABLE 5

| | | | Particle Titer | |
|---|---|---|---|---|
| Capsid | Infectivity | HS Binding | A20 ELISA | DNA Dot Blot |
| A520RGD4C | — | — | $7.5 \times 10^4$ | — |
| A588RGD4C | 52.1% | + | $7 \times 10^5$ | $8 \times 10^4$ |
| A520RGD4C588RGD4C | 45.8% | − | $2 \times 10^5$ | $5 \times 10^4$ |
| ACG | 49.9% | + | $1 \times 10^6$ | $2 \times 10^5$ |

The ability of the double mutant AAV capsids to bind HSPG was assessed as describe in Example 3. The double mutant was unable to bind to HSPG like the A520RGD4C vector, but retained the ability to infect the target cells similar to A5884RGD4C. See Table 9 above. Thus, the double mutant, A520RGD4C588RGD4C, is a receptor-targeted mutant that was produced at a reasonable titer and is defective in binding the AAV2 endogenous receptor HSPG.

Example 5

It was envisioned that insertion of larger peptide epitopes might disrupt the AAV capsid by conformationally straining neighboring sequences. To circumvent this problem, two different approaches, were employed in generating various mutant AAV packaging plasmids described in Example 1. First, in some altered capsids the structure of neighboring capsid regions was maintained by, the introduction of a disulfide bond, and second, in other altered capsids flexible linker sequences were included to minimize conformational stress. See Table 6 below, wherein linker sequence TG-ALS indicates that linker amino acids TG were included at the amino terminus of the inserted epitope and amino acids ALS were included at the carboxy terminus of the inserted epitope.

as alanine or serine) is extremely important for rescuing virus structure, infectivity, and for efficient epitope display.

Example 6

The ability of vector AAV-A139LH (containing the LH receptor binding peptide) to target the human ovarian cancer cell line OVCAR-3 was tested. Expression of the LH receptor is upregulated on these cells. Because OVCAR-3 cells also express HSPG control experiments were performed to demonstrate that the AAV vector indeed exhibited an altered tropism.

Briefly, equal numbers of AAV-A139LH vector particles or vector particles with BPV inserts instead of LH inserts were applied to the surface of OVCAR-3 cells for 2 hours at 4° C. HeLa cells which express HSPG but not the LH receptor were used as a control cell line. Experiments were performed either in the presence or absence of 500 μg/ml soluble heparin sulfate (HS) which competes with binding between AAV and HSPG and in the presence or absence of progesterone which

TABLE 6

Dependence on Appropriate Linker/Scaffolding Sequences

| Mutant Vector Designation | Linker Sequence | Particle Titer | Infectious Titer | HSPG Binding | Epitope Display | Type |
|---|---|---|---|---|---|---|
| AAV-A161BPV/ALS | TG-ALS (SEQ ID NO: 7) | ++++ | ++++ | + | + | III |
| AAV-A161BPV/LLA | TG-LLA (SEQ ID NO: 8) | ++ | ++ | + | + | III |
| AAV-A161BPV/GLS | TG-GLS (SEQ ID NO: 9) | +++ | ++++ | + | + | III |
| AAV-N584BPV/ALS | TG-ALS (SEQ ID NO: 7) | ++++ | ++++ | + | + | III |
| AAV-N584BPV/LLA | TG-LLA (SEQ ID NO: 8) | +++ | − | + | + | II |
| AAV-N584BPV/GLS | TG-GLS (SEQ ID NO: 9) | + | − | − | − | II |
| AAV-A587BPV/ALS | TG-ALS (SEQ ID NO: 7) | +++ | +++ | + | + | III |
| AAV-A587BPV/LLA | TG-LLA (SEQ ID NO: 8) | ++ | − | + | − | II |
| AAV-A587BPV/GLS | TG-GLS (SEQ ID NO: 9) | ++++ | ++ | + | + | III |

Through the choice of appropriate linkers, infectious virus was rescued from previously dead mutants. In other instances, titers were influenced over several orders of magnitude. From this analysis it is clear that incorporation of flexible linkers containing small uncharged amino acids (such increases expression of the LH receptor. The cells were then washed of unbound vector, shifted to 37° C. and maintained for 48 hours at which time gene transfer was assessed.

In the experiments, AAV-A139LH transduced both HeLa and OVCAR-3 cells in the absence of HS. In the presence of HS, transduction of OVCAR-3 cells was reduced more than 10-fold and transduction of Hela cells was reduced more than 100-fold. Addition of progesterone restored transduction of ovarian cells that was lost in the presence of HS. The addition of progesterone increased transduction of OVCAR-3 cells by AAV-A139LH but not by AAV-A139BPV.

These results demonstrate that AAV-A139LH has acquired tropism for cells expressing the LH receptor.

As demonstrated by the foregoing data, AAV vectors of the invention may therefore be used for targeted DNA delivery. Some indications include: cancer gene therapy (e.g., for toxin or "suicide" gene delivery) and therapeutic gene transfer to cell and/or tissue types that have been refractive to gene transfer with conventional AAV vectors (e.g., airway epithelium for the treatment of cystic fibrosis, glia for the treatment of primary brain cancers, and hematopoietic progenitors cells for the treatment of any number of other disorders). For therapeutic gene delivery, AAV vectors of the invention may be targeted to non-antigen presenting cells in order to avoid an immune response to a gene or protein of interest and/or may incorporate epitope shielding moieties and/or mutations of immunodominant epitopes.

Alternatively, AAV vectors may be used as vaccines. Viral particles containing foreign epitopes may be used directly as immunogns. AAV vectors displaying such epitopes may also contain DNA that would lead to the expression of the same or related sequences within target cells. Such a dual immunization approach is contemplated to generate a more robust and wider range response. For vaccine use, targeted AAV vectors may specifically transduce APC (while avoiding other cells).

Finally, AAV vectors of the invention may be used as non-therapeutic reagents such as imaging reagents for the determination of vector pharmokinetics and biodistribution, for example, through the attachment of radio tracer elements and real-time scintography.

Example 7

Fourteen additional AAV capsid mutants were generated in the non-infectious AAV plasmid, pACG, by PCR-based site-directed mutagenesis as described in Example 1. In all thirteen, the 4C-RGD peptide (CDCRGDCFC; SEQ ID NO: 10) was inserted into the AAV capsid monomer.

4C-RGD encoding oligonucleotide were inserted into seven different sites within the AAV capsid gene. One site was within the VP1 unique region of the AAV2 capsid protein gene, three were within the VP1/VP2 unique region, and the three remaining sites were located within the VP3 region of the capsid ORF. DNA encoding the 4C-RGD peptide epitope was either inserted alone or flanked by one of two different five amino acid connecting peptide linkers, as described in Example 5. See Table 7 below. Producer cell lines based on 293 cells were used to generate modified AAV vectors comprising the altered capsids. These modified vectors are denoted as "AAV-RGD" collectively herein.

TABLE 7

| Vector Designation | Upstream Linker | Inserted Peptide (SEQ ID NO: 10) | Downstream Linker | Particle Titer (ELISA) |
|---|---|---|---|---|
| A46-RGD4C | TG | CDCRGDCFC | — | $8.5 \times 10^7$ |
| A46-RGD4CGLS | TG | CDCRGDCFC | GLS | $4.5 \times 10^6$ |
| A115-RGD4C | TG | CDCRGDCFC | — | $4.5 \times 10^6$ |
| A115-RGD4CGLS | TG | CDCRGDCFC | GLS | $6.0 \times 10^7$ |
| A139-RGD4C | TG | CDCRGDCFC | — | $8.5 \times 10^7$ |
| A139-RGD4CGLS | TG | CDCRGDCFC | GLS | $9.0 \times 10^7$ |
| A161-RGD4C | TG | CDCRGDCFC | — | $4.5 \times 10^6$ |
| A161-RGD4CALS | TG | CDCRGDCFC | ALS | $5.0 \times 10^6$ |
| A459-RGD4C | TG | CDCRGDCFC | — | $4.5 \times 10^6$ |
| A459-RGD4CGLS | TG | CDCRGDCFC | GLS | $4.5 \times 10^6$ |
| A584-RGD4C | TG | CDCRGDCFC | — | $8.5 \times 10^7$ |
| A584-RGD4CALS | TG | CDCRGDCFC | ALS | $9.0 \times 10^7$ |
| A588-RGD4C | TG | CDCRGDCFC | — | $9.0 \times 10^7$ |
| A588-RGD4CGLS | TG | CDCRGDCFC | GLS | $9.0 \times 10^7$ |
| Wild-type | — | — | — | $7.5 \times 10^7$ |

All the mutant capsid proteins were efficiently assembled and packaged. Furthermore, all of the modified AAV vectors generated were infectious, although there were significant differences in their efficiency of mediating gene transduction. See Table 8 below.

TABLE 8

| | Percent eGFP Positive Cells | |
| --- | --- | --- |
| Capsid | rAVVeGFP (alone) | rAVVeGFP (+500 µg/ml Heparin Sulfate) |
| A46-RGD4C | 2.5% | 1% |
| A46-RGD4CGLS | 3.% | 0.5% |
| A115-RGD4C | 5% | 1% |
| A115-RGD4CGLS | 7.5% | 1% |
| A139-RGD4C | 35% | 2.5% |
| A139-RGD4CGLS | 40% | 2% |
| A161-RGD4C | 4% | 0.5% |
| A161-RGD4CALS | 5% | 1% |
| A459-RGD4C | 3.5% | 1% |
| A459-RGD4CGLS | 3% | 0.25% |
| A584-RGD4C | 49% | 30% |
| A584-RGD4CALS | 51% | 37% |
| A588-RGD4C | 40% | 32% |
| A588-RGD4CGLS | 46% | 38% |
| Wild-type | 47.5% | 1% |

The differences in gene transduction among the AAV-RGD vectors were related to both the site of peptide insertion and the presence, or absence, of linker sequences flanking the inserted 4C-RGD peptide. Insertion of the RGD epitope following AAV VP1 amino acids at positions 46, 115, 161 or 459 severely diminished infectious titer. However, insertions following the AAV amino acids at positions 139, 584 and 588 were well tolerated and did not affect titer appreciably.

For all the AAV-RGD vectors, inclusion of linker/scaffolding sequences resulted in slightly more efficient infection and maintenance of titer. To determine if the inserted 4C-RGD peptide had imparted to the modified vectors HSPG-independence, gene transduction assays were performed in the presence of heparin sulfate as described in Example 5. Although, AAV vectors containing unmodified capsids were unable to transduce cells in the presence of heparin sulfate, AAV-RGD vectors containing the 4C-RGD epitope following amino acids 584 and 588 transduced all types of cells tested in the presence of heparin sulfate. These results strongly suggest that AAV-RGD vectors set out in Table 6 are infecting cells via a HSPG-independent mechanism.

Example 8

To assess if the AAV-RGD viral particles bind integrin receptors, a solid-phase ELISA assay using purified $\alpha_v\beta_3$ integrin was carried out as follows.

Neutravidin-coated plates (Pierce, Rockford, Ill.) were incubated with 1 µg/well of biotinylated heparin in PBST (0.05% Tween 20, 0.2% BSA) overnight at 4° C. The wells were then washed five times with wash buffer (PBS containing 0.05% Tween-20 and 0.1% BSA) and AAV particles were bound at room temperature for two hours with gentle shaking. Subsequently, the plate was washed five times with wash buffer and purified integrin $\alpha_v\beta_3$ (Chemicon, Temecula, Calif.) in binding buffer (20 mM Tris-HCl, 150 mM NaCl, 2 mM $CaCl_2$. 1 mM $MgCl_2$, 1 mM MnCL2 and 0.1% BSA, pH 7.5) was added to each well at a concentration of 1 µg/ml. The plates were incubated overnight at 4° C., washed three times with wash buffer and incubated with VNR139 monoclonal antibody (anti-$\alpha_v$ subunit, GIBCO-BRL; Gaithersburg, Md.) in binding buffer for 2 hours at room temperature. The plates are then washed five times and incubated with secondary antibody (HRP-conjugated anti-mouse IgG) for 1 hour at room temperature. Following a final wash the ELISA plate was developed with ABTS substrate solution and the VECTASTAIN kit (Vector Laboratories, Burlingame, Calif.) as recommended by the manufacturer. Color development was stopped by the addition of 1N $H_2SO_4$, and plates were read in a plate reader set at 405 nM.

This analysis clearly indicated that the AAV-RGD viral particles bound $\alpha_v\beta_3$ integrin. The unmodified viral particles bound only at background level at all concentrations tested.

Example 9

The insertion of the RGD peptide in the capsid protein of AAV-RGD vectors modified the cellular tropism of these vectors. The cell entry pathway of the AAV RGD vectors was investigated by measuring gene transfer to cell lines expressing various levels of HSPG as well as intergrins $\alpha_v\beta_3$ and $\alpha_v\beta_5$. The following cell lines were tested: Hela cells, K562 human chronic myelogenous leukemia cells and Raji human lymphoblast-like cells.

First, flow cytometry was used to analyze the integrin and HSPG expression profile of these cell lines. Briefly, the cells were resuspended in SM buffer (HEPES-buffered saline containing 1% bovine serum albumin) at $2\times10^6$ cell/ml. The cells were incubated briefly at 37° C. to allow regeneration of surface integrins, then incubated with FITC-labeled LM609 antibody or FITC-labeled PIF6 antibody (1:200 dilution, Chemicon, Temeula, Calif.) for two hours at 4° C. HSPG expression in these cells was analyzed with anti-HSPG monoclonal antibody, HepSS-1 (1:200 dilution) for two hours at 4° C. Subsequently the cells were washed five times with SM buffer and incubated with FITC labeled goat anti-mouse IgM serum (1:800 dilution) for one hour at 4° C., the cells were washed with SM buffer and analyzed by flow cytometry. This analysis demonstrated that Hela cells expressed high levels of HSPG and $\alpha_v\beta_5$ integrin and low levels of $\alpha_v\beta_3$ integrin. K562 cells expressed low levels of HSPG, but $\alpha_v\beta_5$ integrin was expressed at high levels. Raji cells were negative for HSPG expression and expressed high levels of $\beta_v\beta_3$ and $\alpha_v\beta_5$ integrins. Subsequently, the ability of the wild-type AAV-eGFP and the modified vectors (A584-RGD4C-eGFP, A584-RGD4CALS-eGFP, A588-RGD4C-eGFP, A588-RGD4CGLS) to transfer the eGFP gene to Hela, Raji and K562 cells was analyzed. The cells were seeded in a 24-well plates the day prior to infection in order to reach 75% confluence or about $5\times10^5$ cell/ml on the following day. Serial dilutions of the vectors were added to the cells in the presence of Ad5 at the MOI of 3 iu/cell. The cells and viruses were incubated at 37° C. for 48 hours, after which the media was removed and the cells washed two time with PBS. The cells were then fixed and analyzed for GFP transduction by FACS analysis using an anti-GFP antibody.

Due to the low expression of HSPG, K562 and Raji cells were poorly transduced by AAVeGFP vectors containing unmodified AAV capsid protein, but these cells were efficiently transduced by the same vector packaged into A5884C-RGD capsids. The efficiency of eGFP gene transduction by the A5884C-RGD vector was similar to that observed by the unmodified AAV vector in Hela cells. Furthermore, gene transfer mediated by the RGD-containing particles was 4-fold higher in the K562 cells and 13-fold higher in the Raji cells as compared to transduction by vectors comprising unmodified capsids. These experiments clearly demonstrate that incorporation of the 4C-RGD epitope into the VP3 monomer of AAV2 vectors resulted in dramatic changes in the initial steps of virus-cell interaction, presumably by creating an alternative cell attachment and entry pathway.

Experiments were also carried out to compare the binding profiles of the wild type AAV2 vector and that containing the 4C-RGD capsid protein using soluble heparin sulfate to compete for binding, and anti-AAV monoclonal antibody A20 and FACS analysis to detect-binding. In these experiments, wild type AAV2 vector did not bind to Hela cells in the presence of heparin sulfate. However, vectors containing A5884C-RGD capsid protein bound to Hela cells in the presence of soluble heparin sulfate. Binding of modified AAV viral particles to Hela cells was blocked by treatment with synthetic RGD peptide. Since the RGD peptides could efficiently block binding, these data further suggest that AAV-RGD capsids use cellular integrins as receptors during the cell attachment process.

Example 10

Experiments were carried out to determine if the AAV-RGD vectors were capable of mediating gene delivery via integrin receptors.

Competitive inhibition assays using soluble heparin sulfate to inhibit AAV-mediated gene delivery were carried out as follows. AAV-RGD vectors or control vector AAVeGFP and modified vectors A584-RGD4C-eGFP, A584-RGD4CALS-eGFP, A588-RGD4C-eGFP, A588-RGD4CGLS-were first incubated with 1500 μg/ml soluble heparin sulfate for two hours at 37° C. and then incubated with the Hela cells at 4° C. in the presence of 500 μg/ml heparin sulfate for an additional four hours. The cells were subsequently washed three times with fresh medium to remove unbound vector and incubated for 48 hours at 37° C., after which the cells were washed two times with PBS, fixed and analyzed for GFP gene transduction by FACS analysis in Hela cells.

When infected with the control virus, AAVeGFP comprising the unmodified capsid, GFP gene expression in Hela cells was efficiently-blocked by soluble heparin sulfate. The same concentrations of heparin sulfate only blocked about 20% of A5884C-RGD capsid-mediated GFP expression in Hela cells. These experiments further demonstrated that the A5884-RGD capsids were capable of using an alternative HSPG-independent cell entry pathway.

To assess the specificity of the alternate cell entry pathway through integrin receptor, synthetic RGD peptide (200 μg/ml) or anti-integrin antibody VNR139 was used to determine if AAV-RGD mediated gene-transduction was inhibited in the presence of soluble heparin sulfate. The addition of the RGD specific, inhibitor in combination with heparin sulfate completely inhibited A5884C-RGD-mediated gene expression. This experiment demonstrated that the HSPG-independent interaction was due to interaction with RGD-binding integrins expressed on the Hela cells.

Example 11

The ability of unmodified AAV vector (wild type) to mediate GFP gene transduction was tested in various ovarian adenocarcinoma cell lines. Transduction of the eGFP gene was measured by FACS. Unmodified AAV vector mediated gene transfer and expression in the human ovarian adenocarcinoma cell lines PA-1, OVCAR-3, OVCAR-3N and OV4. Unmodified AAV vector did not transduce the ovarian adenocarcinoma cell lines Hey, SKOV-3 and OV3. The unmodified AAV vector transfers the eGFP gene via the HSPG receptor. HSPG expression in ovarian cancer cells was determined by FACS analysis using an anti-HSGP antibody (Seikagaku America, Falmouth, Mass.). The unmodified AAV vector was unable to transduce the Hey and OV3 cell line since these cell lines were negative for HSPG expression. See Table 8.

Since some human ovarian adenocarcinoma cell lines do not express HSPG, it was of interest to determine if ovarian tumor antigens (e.g., integrin) would facilitate AAV-mediated gene transfer in ovarian cancer cells. Integrin expression was analyzed by FACS analysis using an anti-$\alpha_v$ antibody and the data is displayed in Table 9. All ovarian cancer cells tested expressed a member of the $\alpha_v$ integrin family.

TABLE 9

Integrin and HSPG Expression on Human Ovarian Adenocarcinoma

| Ovarian Adenocarcinoma | HSPG Expression | $\alpha_v$ Integrin Expression |
|---|---|---|
| PA-1 | + | + |
| Hey | − | + |
| OVCAR-3 | + | + |
| OVCAR-3N | + | + |
| OV4 | + | + |
| SKOV-3ip | − | + |
| OV3 | − | + |

The AAV-RGD vectors A588-RGD4C-eGFP and A588-RGD4CGLS were tested for their ability to target gene transfer to the ovarian cell lines as described in Example 9. These AAV-RGD vectors were able to transduce all ovarian cancer cell lines tested. The AAV-RGD vectors were able to more efficiently direct gene transfer in the ovarian cell lines PA-1, Hey, OVCAR-3, OVCAR-3N, OV4, SKOV-3ip and OV3 in comparison compared to wild-type AAV vector containing unmodified capsid.

AAV-RGD mediated gene transfer was demonstrated to be independent of HSPG interaction. Competitive gene transfer experiments in the OVCAR-3 cell line were carried out with soluble heparin sulfate as described in Example 10. A5884C-RGD vector efficiently directed gene transfer in the presence of soluble heparin sulfate in OVCAR-3 cells. However, gene transfer was completely blocked by the addition of RGD peptide or anti-integrin antibody in the presence of soluble heparin sulfate. The A5884C-RGD mediated gene transfer proceeded through integrin receptors.

Example 12

Side-by-side comparison of the effectiveness of the unmodified AAV2 vector and the RGD-AAV vector for gene transfer to ovarian tumors was carried out in vivo. Human SKOV-3 cells were delivered intraperitoneally into SKID mice and developed tumors in the peritoneal cavity five days after implantation. The tumors were allowed to develop for five-seven days. Subsequently, matched doses of AAV-RGD vector or unmodified AAV vectors engineered to express the eGFP gene were administered intraperitoneally to the mice at $5 \times 10^8$ particles/mouse. At 15, 25, and 35 days post vector administration, the mice were sacrificed and the tumors were analyzed for the extent of gene delivery and expression. eGFP expression was detected in paraffin sections of tumor tissue using an anti-GFP antibody. In Table 10, GFP gene expression is indicated as a percent of tumor tissue expressing the gene, AAV-RGD indicates tumor tissue harvested from mice treated with AAV-RGD vector and ACG indicates tumor tissue harvested from mice treated with wild type vector.

TABLE 10

| | GFP Expression | |
|---|---|---|
| Day | AAV-RGD | ACG |
| 15 | 15% | 3% |
| 25 | 60% | 7% |
| 35 | 95% | 7% |

It is generally accepted that for an anti-tumor gene therapy to be effective a genetic vector must be able to deliver and express a gene in as much of the tumor as possible. In studies with other transgenes, (e.g., HSV-TK) it has been established that at least 10-15% of the tumor needs to be transduced in order to be effective. This experiment suggest that the unmodified AAV2-vectors would not be effective anti-tumor agents since the transduction rate in vivo was low. In contrast, the modified RGD-AAV vector had a high rate of gene transduction and therefore may an excellent candidate for anti-tumor therapy. The fact that the eGFP expression comes on slowly (increasing over a 5 week period) is not unexpected and is a characteristic of rAAV.

Example 13

In addition to inserting peptides into the AAV2 vector to modify viral tropism, peptide insertions in the AAV2 vector can also be used as substrates for an enzymatic reaction covalently linking a biotin molecule in a site-specific manner to the AAV capsid. AAV capsids have been engineered to include a unique fifteen amino acid long biotin acceptor (BAP) peptide that is recognized by an E. coli enzyme, biotin protein ligase. In the presence of ATP, the ligase specifically attaches biotin to the lysine residue in this sequence. When the bacterial enzyme was expressed in a packaging cell line where AAV vector biosynthesis was occurring, vector capsid proteins were biotinylated as they were made and assembled into viral particles. The result of such a packaging scheme was in vivo biotinylated AAV particles. The advantages to labeling the AAV vector by biotinylation is that the reaction is enzymatic and therefore the conditions are gentle and the labeling is highly specific.

The AAV-BAP vectors were generated by methods similar to those described for the AAV-BPV, AAV-LH and AAV-RGD vectors in Example 1. Six AAV-mutants were generated and the packaging plasmids encoding these mutants are designated herein as pAB139BAP/ALS, pAB139BAP/GLS, pAB161BAP/ALS, pAB161BAP/GLS, pAB584BAP/GLS, and pAB584BAP/ALS. These mutants contain BAP insertions of the peptide sequence (GLNDIFEAQKIEWHE; SEQ ID NO: 11) flanked by either TG-ALS, or TG-GLS linker sequence (SEQ ID NO: 7 and 9, respectively). BAP insertions within the AAV vector following amino acids at positions 139 and 161 (regardless of the linker sequence) produced infectious mutant AAV vector particles at a level similar to wild-type. Insertion of the BAP peptide following amino acid 584 with the GLS linker causes a slight, but insignificant (less than 10-fold), decease in particle titer. Insertion of the BAP peptide at the same site within the AAV vector with the ALS linker caused a significant (>10,00 fold) decrease particle titer. All of the insertion sites within the AAV vector contemplated by the present invention (positions 139 and 161 in the VP1/VP2 region and positions 459, 584, 588 and 657) are candidate sites for the BAP insertion.

Addition of biotin acceptor peptides to the capsid proteins of AAV allowed for the efficient purification of targeted AAV vectors. AAV1 vector capsid proteins were modified with BAP peptide insertions as described in Example 16. AAV helper plasmids containing either BAP or targeting peptide insertions in the Cap ORF were transfected into 293 cells at different ratios along with AAV vector plasmids, adenovirus helper plasmids, and a plasmid expressing the E. coli BirA, biotin ligase. AAV particles were purified by iodixanol gradient centrifugation and avidin-affinity chromatography. The elution fraction was then used to transfect HUVEC cells. An hour incubation at 4° C. and a MOI of 30,000 was used. It is clear that vectors with chimeric RGD/BAP capsids are still capable of targeted transduction. However, the level of receptor-targeted transduction appears to be dependent on the amount of targeting ligand present in the vector particle.

Example 14

In order to label the AAV particles containing the BAP insert with biotin, a system for expressing the biotin ligase (BirA) enzyme in a packaging cell line was developed to create an in vivo biotinylated AAV vector. The BirA gene was inserted into the pCMV plasmid and is designated herein as pCMV-BirA. This plasmid was used to direct BirA gene expression in 283 cells and used with the AAV-BAP vector to produce in vivo biotinylated AAV vector. Briefly, 293 cells were transfected with the pCMV-BirA plasmid with a selectable maker gene (Neo). The resulting packaging cell was stably transfected with a rAAV comprising a DNA of interest flanked by AAV inverted terminal repeats, an AAV helper construct containing cap gene with a mutant BAP insertion (Example 12), an adenovirus helper plasmid or infected with adenovirus. Alternatively, 293 cells (which are standard AAV vector packaging cells) stably transfected with pCMV-BirA may be used as the packaging cell line. In addition, 293 cells infected with the adenovirus engineered to express the BirA gene may be used as the packaging cell line. AAV particles containing capsids with BAP insertions can also be labeled in vitro (post-purification) using purified BirA enzyme (available commercially).

Alternatively, a recombinant replication-competent adenovirus that expresses BirA was also developed for biotinylated AAV vector synthesis, eliminating the need for a separate BirA expression plasmid. This system allowed for large-scale AAV vector production of the biotinylated AAV utilizing packaging cell lines that have integrated copies of both AAV vector and AAV helper sequences. The Ad-based BirA expression system also was able to drive the expression of much larger amounts of the BirA gene product. The adenovirus expressed a BirA-eGFP fusion protein from a CMV promoter in the Ad E3 region, which allowed for monitoring BirA expression via GFP fluorescence.

A sensitive ELISA assay was used to quantitate the extent and efficiency of in vivo (and/or in vitro) biotinylation. AAV containing the 584BAP/GLS insertion was shown to be efficiently biotinylated in vivo (and in vitro) using either the plasmid based or Ad-based BirA expression systems. The biotinylated AAV vectors when conjugated to biotinylated ligands (e.g., monoclonal antibodies) via strepavidin can be specifically targeted to cell surface receptors of interest.

The advantages of using the biotinylation reaction to label the AAV viral particles is that it is an enzymatic reaction and therefore the conditions are gentle while the labeling is highly specific. In addition, the in vivo biotinylation reaction described herein has a much higher biotinylation efficiency than chemical biotinylation utilizing cross-linking reagents.

The biotinylated AAV viral particles are contemplated to serve as substrates for conjugation of targeting motifs (e.g., monoclonal antibodies, growth factors, cytokines) to the surface of vector particles through utilizing avidin/strepavidin-biotin chemistry. In addition, the biotinylated AAV viral particles are contemplated to be useful for visualizing the biodistribution of the viral particles both in vivo and in vitro. The biotinylated viral particles can be visualized with fluorescence or enzymatically with labeled strepavidin compounds. Biotinylation may also be useful for conjugating epitope shielding moieties, such as polyethylene glycol, to the AAV vector. The conjugation of shielding moieties will allow the vector to evade immune recognition. Biotinylation of the AAV vector is also contemplated to enhance intracellular trafficking of viral particles through conjugation of proteins or peptides such as nuclear transport proteins. Biotinylation may also be use to conjugate proteins or peptides which effect the processing of AAV vector genomes such as increasing the efficiency of integration. In addition, biotinylation may also be used to conjugate proteins or peptides that effect the target cells, e.g., proteins that make a target cell more susceptible to infection or proteins that activate a target cell thereby making it a better target for the expression of a therapeutic or antigenic peptide.

Example 15

An alignment of the AAV capsid amino acid sequences allowed for the determination of insertion sites that correspond to those sites of insertion in AAV2 described in Example 1. As demonstrated in Example 1, the region of amino acids 584-588 of the AAV2 VP3 capsid may be altered without loss of viral titer or infectivity. Epitope insertion experiments were carried out on various AAV serotypes where biotin acceptor peptides (BAP) were inserted at insertion sites corresponding to those described in Example 1 for the AAV2 serotype that can be altered without affecting infectability. The amino acid sequences of serotypes AAV1, AAV2, AAV3, AAV4, and AAV5 were aligned as shown in FIG. 2, which allowed for the identification of insertion sites that corresponded to the insertion sites described in the specification for AAV2. (See FIG. 2) Using the alignments, BAP was inserted at the corresponding regions in the capsid proteins of the AAV vectors as shown in FIG. 2 by the open arrows using the techniques described in Example 13.

The AAV-BAP vectors were generated by site-directed mutagenesis of plasmids containing the corresponding AAV serotype Rep and Cap open reading frames (ORF). Mutagenesis was confirmed by restriction endonuclease digestion. The altered Cap genes were then substituted for the wild-type AAV serotype sequences in plasmid pACG$^2$ to generate the mutant helper plasmids. Subsequently, the mutant AAV packaging plasmids were tested for their ability to generate AAV vectors with altered capsids by triple transfection with plasmid pAAV-LacZ (a plasmid containing LacZ flanked by AAV ITRs) and pXX6-80 (a plasmid containing Adenovirus helper DNA) according to established procedures. AAV vector preparations were assessed for particle formation. Particles were identified by ELISA using the A20 monoclonal antibody and DNA-containing particles were identified by dot-blot and/or PCR. As shown in FIG. 3, the insertion of BAP did not significantly decrease viral particle production in any of the AAV vector serotypes tested when compared to the corresponding vector serotypes. These experiments demonstrate that epitope insertions at sites in various AAV vector serotypes corresponding to those described for AAV2 in the application are as effective as insertions at those sites in AAV2.

Example 16

Cells of the vasculature, such as endothelial cells and smooth muscle cells, are known to be refractive to AAV transduction. Therefore, AAV1 and AAV2 vector capsid proteins were modified with a vasculature targeting peptide insertion. Peptide ligands previously shown to bind to proteins/receptors expressed on proliferating vasculature include RGD4C-which targets $\alpha_v\beta_{3/5}$ integrins, APN (SEQ ID NO: 27) which targets aminopeptidase, HMGN2A (SEQ ID NO: 44) and HMGN2B (SEQ ID NO: 45) which targets human high mobility group antigen receptor, VR2A (SEQ ID NO: 28), VR2B (SEQ ID NO: 29), VR2C (SEQ ID NO: 30), VR2D (SEQ ID NO: 31) and VR2E (SEQ ID NO: 32) which target the VEGF receptor type 2 and Tie2A (SEQ ID NO: 33) and Tie2B (SEQ ID NO: 34) which target the Tie2 receptor.

These vasculature specific targeting peptides were incorporated into all three capsid proteins (VP1, VP2, and VP3) immediately following AAV1 VP1 amino acid 590, or AAV2 VP1 amino acid 588 using techniques described in Example 1. The biotin acceptor peptide (BAP) was also incorporated into AAV1 capsid proteins following AAV1 VP1 amino acid 590 as described in Example 13. Incorporation of the BAP epitope was used for purification of chimeric targeted vectors as described in Example 13

TABLE 11

Vasculature Targeting Peptides

| Plasmid | Insert Position | Insert | Length (AA) | SEQ ID NO: | Targets | Binds Heparan |
|---|---|---|---|---|---|---|
| pXR1 (AAV1) | 590 | RGD4C | 9 | 1 | aVb3/5 Integrins | No |
| | 590 | APN | 5 | 27 | Amino-peptidase N | No |
| | 590 | HMGN2A | 12 | 44 | Human High Mobility Group Antigen Rec. | No |
| | 590 | VR2 A | 7 | 28 | Vegf Rec 2 (KDR) | No |
| | 590 | VR2 B | 7 | 29 | Vegf Rec 2 (KDR) | No |
| | 590 | VR2 C | 7 | 30 | Vegf Rec 2 (KDR) | No |
| | 590 | VR2 D | 12 | 31 | Vegf Rec 2 (KDR) | No |
| | 590 | VR2 E | 12 | 32 | Vegf Rec 2 (KDR) | No |
| | 590 | Tie2R A | 7 | 33 | Tie2 Receptor | No |
| | 590 | Tie2R B | 7 | 34 | Tie2 Receptor | No |
| | 590 | BAP | 15 | 1 | Biotin acceptor peptide (becomes biotinylated) | No |
| pACG (AAV2) | 588 | RGD4C | 9 | 27 | aVb3/5 Integrins | Yes |
| | 588 | VR2 A | 7 | 28 | Vegf Rec 2 (KDR) | Yes |
| | 588 | VR2 B | 7 | 29 | Vegf Rec 2 (KDR) | Yes |
| | 588 | VR2 C | 7 | 30 | Vegf Rec 2 (KDR) | Yes |
| pACG HS- (HS-AAV2) | 588 | RGD4C | 9 | 1 | aVb3/5 Integrins | No |
| | 588 | VR2 A | 7 | 28 | Vegf Rec 2 (KDR) | No |

TABLE 11-continued

Vasculature Targeting Peptides

| Plasmid | Insert Position | Insert | Length (AA) | SEQ ID NO: | Targets | Binds Heparan |
|---|---|---|---|---|---|---|
| | 588 | VR2 B | 7 | 29 | Vegf Rec 2 (KDR) | No |
| | 588 | VR2 C | 7 | 30 | Vegf Rec 2 (KDR) | No |
| | 588 | VR2 D | 12 | 31 | Vegf Rec 2 (KDR) | No |
| | 588 | VR2 E | 12 | 32 | Vegf Rec 2 (KDR) | No |
| pVP2 (VP2 of AAV2) | 138 | Vegf 165 | 165 | | Vegf Receptors | * |
| | 138 | VR2 A | 7 | 28 | Vegf Rec 2 (KDR) | * |
| | 138 | VR2 B | 7 | 29 | Vegf Rec 2 (KDR) | * |
| | 138 | VR2 C | 7 | 30 | Vegf Rec 2 (KDR) | * |
| | 138 | VR2 D | 12 | 31 | Vegf Rec 2 (KDR) | * |
| | 138 | VR2 E | 12 | 32 | Vegf Rec 2 (KDR) | * |
| | 138 | RGD4C | 9 | 1 | aVb3/5 Integrins | * |

*pVp2 complimented with pYP1,3 virus will bind heparan
*pVp2 complimented with pVP1,3 HS- virus will not bind heparan (R588A mutation)

The ability of the above described vasculature targeting peptides to enhance AAV vector transduction of different primary human endothelial cells was investigated. Low passage human umbilical vein endothelial cells (HUVEC), human saphenous vein endothelial cells (HSaVEC), and human coronary artery endothelial cells (HCAEC) were grown in 48-well plates to approximately 80% confluence. The cells were then placed in serum/VEGF free media, and rAAVdsRed2 vectors with the indicated capsids were added at a MOI of 25,000 DRP/cell or 15,000 DRP/cell. Vector was allowed to adsorb to the cells for 16 hours at 37° C. or 1 hour at 4° C., after which the cells were washed three times, and fresh media containing serum and supplements was added. At approximately 3.5 days post-infection, gene transduction was determined by fluorescence microscopy.

Integrin targeted AAV1 (RGD4C), integrin targeted/BAP chimeric AAV1 (RGD/BAP), and Tie2RB vectors displayed significantly higher gene transfer to all endothelial cell types compared to unmodified AAV1 vector. Transduction of HSaVECs was >22 fold (p<0.002) more efficient with the RGD/BAP chimeric AAV1 than with untargeted AAV1. In HCAECs, AAV1-RGD/BAP was 66 fold (p<0.0001) more efficient and AAV1-VEGFR2E/BAP was 4 times (p=0.044) more efficient. In HUVECs, AAV1-RGD/BAP was 57 fold more efficient (p=0.01), AAV1-VR2B was 4.2 fold more efficient (p=0.04), and Tie2RB was 7 fold more efficient (p=0.02).

Competition assay were carried out to confirm that transduction of the human primary endothelial cells proceeded via the targeted receptors. Tropism-modified (RGD) and wild-type AAV1dsRed2 vectors were incubated with either HSaVEC or HCAEC in the presence or absence of competing RGD peptide, or control RGS peptide for 1 hour at 4° C. The cells were washed, fresh media was added, and gene transduction was assessed at 3.5 days. RGD peptide competition significantly reduced cellular transduction mediated by the RGD-targeted vector in both HSaVEC (p=0.015) and HCAEC (p=0.027). While there was no difference with the unmodified AAV1 vector. This experiment indicates the transduction of the human endothelial cells proceeded via the vasculature specific targeted receptors.

AAV1 based vectors have the ability to better transduce the vasculature in vivo compared to the other AAV serotypes. The experiment described herein demonstrate that incorporating peptides that bind to proteins expressed on vascular endothelial cells into the viral capsid, can increase the viruses ability to transduce endothelial cells in vitro. By also incorporating the BAP peptide and producing metabolically biotinylated vectors, the vector particles can be easily purified (see Example 13). While the VEGFR2 and Tie2R targeted virus only increased transduction slightly, it is thought that this may be due to low levels of receptor expression in vitro (Zhang et al., *AJP-Heart* 287: 2739-2745, 2004). Ischemia, vascular proliferation, and angiogenesis have been shown to greatly increase levels of VEGFR2 and Tie2R expression in vivo (Beck et al., *Curr. Gene Ther.* 4: 457-467, 2004). Suggesting that the ability of these modified vectors to enhance transduction to these areas of the vasculature in vivo may be even greater.

While the present invention has been described in terms of preferred embodiments, it understood that variations and improvements will occur to those skilled in the art. Therefore, only such limitations as appear in the claims should be placed on the invention.

What is claimed:

1. An AAV1 vector comprising an AAV1 VP1 capsid protein (SEQ ID NO:20) with an insertion of two to fifteen amino acids in length, immediately following the amino acid at position 590 in the VP1 capsid; wherein the insertion does not prevent assembly of the vector or the infectivity of the vector.

2. An AAV4 vector comprising an AAV4 VP1 capsid protein (SEQ ID NO:24) with an insertion of two to fifteen amino acids in length, immediately following the amino acid at position 584 in the VP1 capsid; and wherein the insertion does not prevent assembly of the vector or the infectivity of the vector.

3. An AAV5 vector comprising an AAV5 VP1 capsid protein (SEQ ID NO:36) with an insertion of two to fifteen amino acids in length, immediately following the amino acid at position 575 in the VP1 capsid; and wherein the insertion does not prevent assembly of the vector or the infectivity of the vector.

4. The AAV vector of any one of claims 1, 2 and 3, wherein the amino acid insertion is a targeting peptide.

5. The AAV vector of claim 4 wherein the targeting peptide comprises the amino acids CDCRGDCFC (SEQ ID NO: 10).

6. The AAV vector of any one of claims 1, 2 and 3 wherein the insertion is flanked by a linker/scaffolding sequence.

7. The AAV vector of claim 6 wherein the linker/scaffolding sequence comprises the amino acids TG amino terminal to the insertion and ALS carboxy terminal to the insertion.

8. The AAV vector of claim 6 wherein the linker/scaffolding sequence comprises the amino acids TG amino terminal to the insertion and LLA carboxy terminal to the insertion.

9. The AAV vector of claim 6 wherein the linker/scaffolding sequence comprises the amino acids TG amino terminal to the insertion and GLS carboxy terminal to the insertion.

10. A pharmaceutical composition comprising the AAV vector of any one of claims 1, 2 and 3 in a pharmaceutically acceptable carrier.

11. A polynucleotide encoding the capsid protein of an AAV1 VP1 capsid protein (SEQ ID NO:20) with an insertion of two to fifteen amino acids in length, immediately following the amino acid at position 590 in the VP1 capsid of AAV1; wherein the insertion does not prevent assembly of the vector or the infectivity of the vector.

12. A polynucleotide encoding the capsid protein of an AAV4 VP1 capsid protein (SEQ ID NO:24) with an insertion of two to fifteen amino acids in length, immediately following the amino acid at position 584 in the VP1 capsid; and wherein the insertion does not prevent assembly of the vector or the infectivity of the vector.

13. A polynucleotide encoding the capsid protein of an AAV5 VP1 capsid protein (SEQ ID NO:36) with an insertion of two to fifteen amino acids in length, immediately following the amino acid at position 575 in the VP1 capsid; and wherein the insertion does not prevent assembly of the vector or the infectivity of the vector.

14. A cell transfected with the polynucleotide of claim 11, 12 or 13.

15. A method of producing AAV vector comprising a capsid protein with an amino acid insertion, comprising growing a packaging cell and providing the packaging cell with helper virus functions, wherein said packaging cell comprises an AAV helper construct and a recombinant AAV construct, wherein the AAV helper construct comprises the polynucleotide of claim 11, 12 or 13 and the AAV rep gene, and wherein the recombinant AAV construct comprises a DNA of interest flanked by AAV inverted terminal repeats.

16. The method of claim 15 wherein said cell expresses biotin ligase.

17. The method of claim 16 further comprising the step of treating said AAV vector produced with biotin ligase.

18. The method of claim 15 wherein the DNA of interest encodes a therapeutic peptide or a reporter peptide.

19. The method of claim 15 wherein the DNA of interest is an antisense nucleic acid or ribozyme.

* * * * *

SEQUENCE LISTING

```
<160> NUMBER OF SEQ ID NOS: 50

<210> SEQ ID NO 1
<211> LENGTH: 14
<212> TYPE: PRT
<213> ORGANISM: Artificial sequence
<220> FEATURE:
<223> OTHER INFORMATION: Synthetic RGD Peptide

<400> SEQUENCE: 1

Thr Gly Cys Asp Cys Arg Gly Asp Cys Phe Cys Gly Leu Ser
1               5                   10

<210> SEQ ID NO 2
```

```
<211> LENGTH: 11
<212> TYPE: PRT
<213> ORGANISM: Artificial sequence
<220> FEATURE:
<223> OTHER INFORMATION: Synthetic Bovine Papilloma Virus Peptide

<400> SEQUENCE: 2

Thr Gly Thr Pro Phe Tyr Leu Lys Gly Leu Ser
1               5                   10

<210> SEQ ID NO 3
<211> LENGTH: 15
<212> TYPE: PRT
<213> ORGANISM: Artificial sequence
<220> FEATURE:
<223> OTHER INFORMATION: Synthetic Luteinizing hormone Peptide

<400> SEQUENCE: 3

Thr Gly His Cys Ser Thr Cys Tyr Tyr His Lys Ser Gly Leu Ser
1               5                   10                  15

<210> SEQ ID NO 4
<211> LENGTH: 11
<212> TYPE: PRT
<213> ORGANISM: Artificial sequence
<220> FEATURE:
<223> OTHER INFORMATION: Synthetic peptide

<400> SEQUENCE: 4

Thr Gly Thr Pro Phe Tyr Leu Lys Ala Leu Ser
1               5                   10

<210> SEQ ID NO 5
<211> LENGTH: 11
<212> TYPE: PRT
<213> ORGANISM: Artificial sequence
<220> FEATURE:
<223> OTHER INFORMATION: Synthetic Bovine Papilloma Virus Peptide

<400> SEQUENCE: 5

Thr Gly Thr Pro Phe Tyr Leu Lys Leu Leu Ala
1               5                   10

<210> SEQ ID NO 6
<211> LENGTH: 8
<212> TYPE: PRT
<213> ORGANISM: Artificial sequence
<220> FEATURE:
<223> OTHER INFORMATION: Synthetic Bovine Papilloma Virus Peptide

<400> SEQUENCE: 6

Thr Gly Thr Pro Phe Tyr Leu Lys
1               5

<210> SEQ ID NO 7
<211> LENGTH: 5
<212> TYPE: PRT
<213> ORGANISM: Artificial sequence
<220> FEATURE:
<223> OTHER INFORMATION: Synthetic Liner Peptide

<400> SEQUENCE: 7

Thr Gly Ala Leu Ser
1               5

<210> SEQ ID NO 8
<211> LENGTH: 5
```

```
<212> TYPE: PRT
<213> ORGANISM: Artificial sequence
<220> FEATURE:
<223> OTHER INFORMATION: Synthetic Peptide

<400> SEQUENCE: 8

Thr Gly Leu Leu Ala
1               5

<210> SEQ ID NO 9
<211> LENGTH: 5
<212> TYPE: PRT
<213> ORGANISM: Artificial sequence
<220> FEATURE:
<223> OTHER INFORMATION: Synthetic Peptide

<400> SEQUENCE: 9

Thr Gly Gly Leu Ser
1               5

<210> SEQ ID NO 10
<211> LENGTH: 9
<212> TYPE: PRT
<213> ORGANISM: Artificial sequence
<220> FEATURE:
<223> OTHER INFORMATION: Synthetic 4C-RGD Peptide

<400> SEQUENCE: 10

Cys Asp Cys Arg Gly Asp Cys Phe Cys
1               5

<210> SEQ ID NO 11
<211> LENGTH: 15
<212> TYPE: PRT
<213> ORGANISM: Artificial sequence
<220> FEATURE:
<223> OTHER INFORMATION: Synthetic Biotin acceptor peptide

<400> SEQUENCE: 11

Gly Leu Asn Asp Ile Phe Glu Ala Gln Lys Ile Glu Trp His Glu
1               5                   10                  15

<210> SEQ ID NO 12
<211> LENGTH: 4679
<212> TYPE: DNA
<213> ORGANISM: adeno-associated virus 2

<400> SEQUENCE: 12
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctggagg ggtggagtcg tgacgtgaat tacgtcatag     180
ggttagggag gtcctgtatt agaggtcacg tgagtgtttt gcgacatttt gcgacaccat     240
gtggtcacgc tgggtattta agcccgagtg agcacgcagg gtctccattt tgaagcggga     300
ggtttgaacg cgcagccgcc atgccggggt tttacgagat tgtgattaag gtccccagcg     360
accttgacga gcatctgccc ggcatttctg acagctttgt gaactgggtg gccgagaagg     420
aatgggagtt gccgccagat tctgacatgg atctgaatct gattgagcag caccccctga     480
ccgtggccga agctgcagc gcgactttc tgacggaatg cgccgtgtg agtaaggccc       540 cggaggccct tttctttgtg caatttgaga agggagagag ctacttccac atgcacgtgc     600
tcgtggaaac caccggggtg aaatccatgg ttttgggacg tttcctgagt cagattcgcg     660
```

```
aaaaactgat tcagagaatt taccgcggga tcgagccgac tttgccaaac tggttcgcgg    720
tcacaaagac cagaaatggc gccggaggcg ggaacaaggt ggtggatgag tgctacatcc    780
ccaattactt gctccccaaa acccagcctg agctccagtg ggcgtggact aatatggaac    840
agtatttaag cgcctgtttg aatctcacgg agcgtaaacg gttggtggcg cagcatctga    900
cgcacgtgtc gcagacgcag gagcagaaca aagagaatca gaatcccaat tctgatgcgc    960
cggtgatcag atcaaaaact tcagccaggt acatggagct ggtcgggtgg ctcgtggaca   1020
aggggattac ctcggagaag cagtggatcc aggaggacca ggcctcatac atctccttca   1080
atgcggcctc caactcgcgg tcccaaatca aggctgcctt ggacaatgcg ggaaagatta   1140
tgagcctgac taaaaccgcc cccgactacc tggtgggcca gcagcccgtg gaggacattt   1200
ccagcaatcg gatttataaa attttggaac taaacgggta cgatcccaa tatgcggctt    1260 ccgtctttct gggatgggcc acgaaaaagt tcggcaagag gaacaccatc tggctgtttg   1320
ggcctgcaac taccgggaag accaacatcg cggaggccat agcccacact gtgcccttct   1380
acgggtgcgt aaactggacc aatgagaact ttccccttcaa cgactgtgtc gacaagatgg   1440
tgatctggtg ggaggagggg aagatgaccg ccaaggtcgt ggagtcggcc aaagccattc   1500
tcggaggaag caaggtgcgc gtggaccaga aatgcaagtc ctcggcccag atagacccga   1560
ctcccgtgat cgtcacctcc aacaccaaca tgtgcgccgt gattgacggg aactcaacga   1620
ccttcgaaca ccagcagccg ttgcaagacc ggatgttcaa atttgaactc acccgccgtc   1680
tggatcatga ctttgggaag gtcaccagc aggaagtcaa agactttttc cggtgggcaa    1740
aggatcacgt ggttgaggtg gagcatgaat ctacgtcaa aaagggtgga gccaagaaaa    1800
gacccgcccc cagtgacgca gatataagtg agcccaaacg ggtgcgcgag tcagttgcgc   1860
agccatcgac gtcagacgcg gaagcttcga tcaactacgc agacaggtac caaaacaaat   1920
gttctcgtca cgtgggcatg aatctgatgc tgtttccctg cagacaatgc gagagaatga   1980
atcagaattc aaatatctgc ttcactcacg gacagaaaga ctgtttagag tgctttcccg   2040
tgtcagaatc tcaacccgtt tctgtcgtca aaaaggcgta tcagaaactg tgctacattc   2100
atcatatcat gggaaaggtg ccagacgctt gcactgcctg cgatctggtc aatgtggatt   2160
tggatgactg catctttgaa caataaatga tttaaatcag gtatggctgc cgatggttat    2220
cttccagatt ggctcgagga cactctctct gaaggaataa gacagtggtg gaagctcaaa    2280
cctggcccac caccaccaaa gcccgcagag cggcataagg acgacagcag gggtcttgtg    2340
cttcctgggt acaagtacct cggacccttc aacggactcg acaagggaga gccggtcaac    2400
gaggcagacg ccgcggccct cgagcacgac aaagcctacg accggcagct cgacagcgga    2460
gacaacccgt acctcaagta caaccacgcc gacgcggagt tcaggagcg ccttaaagaa     2520 gatacgtctt ttgggggcaa cctcggacga gcagtcttcc aggcgaaaaa gagggttctt    2580
gaacctctgg gcctggttga ggaacctgtt aagacggctc cggaaaaaaa gaggccggta    2640
gagcactctc ctgtggagcc agactcctcc tcgggaaccg aaaggcgggg ccagcagcct    2700
gcaagaaaaa gattgaattt tggtcagact ggagacgcag actcagtacc tgaccccag     2760 cctctcggac agccaccagc agccccctct ggtctgggaa ctaatacgat ggctacaggc    2820
agtggcgcac aatgcagaa caataacgag ggcgccgacg gagtgggtaa ttcctcggga    2880
aattggcatt gcgattccac atggatgggc gacagagtca tcaccaccag cacccgaacc    2940 tgggcccctgc ccacctacaa caaccacctc tacaaacaaa tttccagcca atcaggagcc    3000
tcgaacgaca atcactactt tggctacagc acccccttggg ggtattttga cttcaacaga   3060
```

-continued

```
ttccactgcc acttttcacc acgtgactgg caaagactca tcaacaacaa ctggggattc    3120
cgacccaaga gactcaactt caagctcttt aacattcaag tcaaagaggt cacgcagaat    3180
gacggtacga cgacgattgc caataacctt accagcacgg ttcaggtgtt tactgactcg    3240
gagtaccagc tcccgtacgt cctcggctcg gcgcatcaag gatgcctccc gccgttccca    3300
gcagacgtct tcatggtgcc acagtatgga tacctcaccc tgaacaacgg gagtcaggca    3360
gtaggacgct cttcatttta ctgcctggag tactttcctt ctcagatgct gcgtaccgga    3420
aacaacttta ccttcagcta cacttttgag gacgttcctt tccacagcag ctacgctcac    3480
agccagagtc tggaccgtct catgaatcct ctcatcgacc agtacctgta ttacttgagc    3540
agaacaaaca ctccaagtgg aaccaccacg cagtcaaggc ttcagttttc tcaggccgga    3600
gcgagtgaca ttcgggacca gtctaggaac tggcttcctg accctgttta ccgccagcag    3660
cgagtatcaa agacatctgc ggataacaac aacagtgaat actcgtggac tggagctacc    3720
aagtaccacc tcaatggcag agactctctg gtgaatccgg gcccggccat ggcaagccac    3780
aaggacgatg aagaaaagtt ttttcctcag agcggggttc tcatctttgg gaagcaaggc    3840
tcagagaaaa caaatgtgga cattgaaaag gtcatgatta cagacgaaga ggaaatcagg    3900
acaaccaatc ccgtggctac ggagcagtat ggttctgtat ctaccaacct ccagagaggc    3960
aacagacaag cagctaccgc agatgtcaac acacaaggcg ttcttccagg catggtctgg    4020
caggacagag atgtgtacct tcaggggccc atctgggcaa agattccaca cacggacgga    4080
cattttcacc cctctcccct catgggtgga ttcggactta aacaccctcc tccacagatt    4140
ctcatcaaga caccccggt acctgcgaat ccttcgacca ccttcagtgc ggcaaagttt    4200
gcttccttca tcacacagta ctccacggga caggtcagcg tggagatcga gtgggagctg    4260
cagaaggaaa acagcaaacg ctggaatccc gaaattcagt acacttccaa ctacaacaag    4320
tctgttaatg tggactttac tgtggacact aatggcgtgt attcagagcc tcgccccatt    4380
ggcaccagat acctgactcg taatctgtaa ttgcttgtta atcaataaac cgtttaattc    4440
gtttcagttg aactttggtc tctgcgtatt tctttcttat ctagtttcca tggctacgta    4500
gataagtagc atggcgggtt aatcattaac tacaaggaac ccctagtgat ggagttggcc    4560
actccctctc tgcgcgctcg ctcgctcact gaggccgggc gaccaaaggt cgcccgacgc    4620
ccgggctttg cccgggcggc ctcagtgagc gagcgagcgc gcagagaggg agtggccaa     4679
```

<210> SEQ ID NO 13
<211> LENGTH: 735
<212> TYPE: PRT
<213> ORGANISM: adeno-associated virus 2

<400> SEQUENCE: 13

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
```

-continued

```
                85                  90                  95
Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Pro Val Lys Thr Ala Pro Gly Lys Lys Arg
        130                 135                 140

Pro Val Glu His Ser Pro Val Glu Pro Asp Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
            195                 200                 205

Ala Pro Met Ala Asp Asn Asn Glu Gly Ala Asp Gly Val Gly Asn Ser
        210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
        290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510
```

-continued

```
Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
            610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
            690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 14
<211> LENGTH: 598
<212> TYPE: PRT
<213> ORGANISM: adeno-associated virus 2

<400> SEQUENCE: 14

Met Ala Pro Gly Lys Lys Arg Pro Val Glu His Ser Pro Val Glu Pro
1               5                   10                  15

Asp Ser Ser Ser Gly Thr Gly Lys Ala Gly Gln Gln Pro Ala Arg Lys
            20                  25                  30

Arg Leu Asn Phe Gly Gln Thr Gly Asp Ala Asp Ser Val Pro Asp Pro
        35                  40                  45

Gln Pro Leu Gly Gln Pro Pro Ala Ala Pro Ser Gly Leu Gly Thr Asn
    50                  55                  60

Thr Met Ala Thr Gly Ser Gly Ala Pro Met Ala Asp Asn Asn Glu Gly
65                  70                  75                  80

Ala Asp Gly Val Gly Asn Ser Ser Gly Asn Trp His Cys Asp Ser Thr
                85                  90                  95

Trp Met Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Gln Ser Gly
        115                 120                 125

Ala Ser Asn Asp Asn His Tyr Phe Gly Tyr Ser Thr Pro Trp Gly Tyr
    130                 135                 140

Phe Asp Phe Asn Arg Phe His Cys His Phe Ser Pro Arg Asp Trp Gln
```

```
                                   -continued
145                    150                 155                 160
      Arg Leu Ile Asn Asn Trp Gly Phe Arg Pro Lys Arg Leu Asn Phe
                      165                 170                 175

Lys Leu Phe Asn Ile Gln Val Lys Glu Val Thr Gln Asn Asp Gly Thr
                      180                 185                 190

Thr Thr Ile Ala Asn Asn Leu Thr Ser Thr Val Gln Val Phe Thr Asp
                      195                 200                 205

Ser Glu Tyr Gln Leu Pro Tyr Val Leu Gly Ser Ala His Gln Gly Cys
                      210                 215                 220

Leu Pro Pro Phe Pro Ala Asp Val Phe Met Val Pro Gln Tyr Gly Tyr
      225                 230                 235                 240

Leu Thr Leu Asn Asn Gly Ser Gln Ala Val Gly Arg Ser Ser Phe Tyr
                      245                 250                 255

Cys Leu Glu Tyr Phe Pro Ser Gln Met Leu Arg Thr Gly Asn Asn Phe
                      260                 265                 270

Thr Phe Ser Tyr Thr Phe Glu Asp Val Pro Phe His Ser Ser Tyr Ala
                      275                 280                 285

His Ser Gln Ser Leu Asp Arg Leu Met Asn Pro Leu Ile Asp Gln Tyr
                      290                 295                 300

Leu Tyr Tyr Leu Ser Arg Thr Asn Thr Pro Ser Gly Thr Thr Thr Gln
      305                 310                 315                 320

Ser Arg Leu Gln Phe Ser Gln Ala Gly Ala Ser Asp Ile Arg Asp Gln
                      325                 330                 335

Ser Arg Asn Trp Leu Pro Gly Pro Cys Tyr Arg Gln Gln Arg Val Ser
                      340                 345                 350

Lys Thr Ser Ala Asp Asn Asn Asn Ser Glu Tyr Ser Trp Thr Gly Ala
                      355                 360                 365

Thr Lys Tyr His Leu Asn Gly Arg Asp Ser Leu Val Asn Pro Gly Pro
                      370                 375                 380

Ala Met Ala Ser His Lys Asp Asp Glu Glu Lys Phe Phe Pro Gln Ser
      385                 390                 395                 400

Gly Val Leu Ile Phe Gly Lys Gln Gly Ser Glu Lys Thr Asn Val Asp
                      405                 410                 415

Ile Glu Lys Val Met Ile Thr Asp Glu Glu Ile Arg Thr Thr Asn
                      420                 425                 430

Pro Val Ala Thr Glu Gln Tyr Gly Ser Val Ser Thr Asn Leu Gln Arg
                      435                 440                 445

Gly Asn Arg Gln Ala Ala Thr Ala Asp Val Asn Thr Gln Gly Val Leu
                      450                 455                 460

Pro Gly Met Val Trp Gln Asp Arg Asp Val Tyr Leu Gln Gly Pro Ile
      465                 470                 475                 480

Trp Ala Lys Ile Pro His Thr Asp Gly His Phe His Pro Ser Pro Leu
                      485                 490                 495

Met Gly Gly Phe Gly Leu Lys His Pro Pro Gln Ile Leu Ile Lys
                      500                 505                 510

Asn Thr Pro Val Pro Ala Asn Pro Ser Thr Thr Phe Ser Ala Ala Lys
                      515                 520                 525

Phe Ala Ser Phe Ile Thr Gln Tyr Ser Thr Gly Gln Val Ser Val Glu
                      530                 535                 540

Ile Glu Trp Glu Leu Gln Lys Glu Asn Ser Lys Arg Trp Asn Pro Glu
      545                 550                 555                 560

Ile Gln Tyr Thr Ser Asn Tyr Asn Lys Ser Val Asn Val Asp Phe Thr
                      565                 570                 575
```

```
Val Asp Thr Asn Gly Val Tyr Ser Glu Pro Arg Pro Ile Gly Thr Arg
            580                 585                 590

Tyr Leu Thr Arg Asn Leu
        595

<210> SEQ ID NO 15
<211> LENGTH: 533
<212> TYPE: PRT
<213> ORGANISM: adeno-associated virus 2

<400> SEQUENCE: 15

Met Ala Thr Gly Ser Gly Ala Pro Met Ala Asp Asn Asn Glu Gly Ala
1               5                   10                  15

Asp Gly Val Gly Asn Ser Ser Gly Asn Trp His Cys Asp Ser Thr Trp
            20                  25                  30

Met Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Gln Ser Gly Ala
    50                  55                  60

Ser Asn Asp Asn His Tyr Phe Gly Tyr Ser Thr Pro Trp Gly Tyr Phe
65                  70                  75                  80

Asp Phe Asn Arg Phe His Cys His Phe Ser Pro Arg Asp Trp Gln Arg
                85                  90                  95

Leu Ile Asn Asn Asn Trp Gly Phe Arg Pro Lys Arg Leu Asn Phe Lys
            100                 105                 110

Leu Phe Asn Ile Gln Val Lys Glu Val Thr Gln Asn Asp Gly Thr Thr
        115                 120                 125

Thr Ile Ala Asn Asn Leu Thr Ser Thr Val Gln Val Phe Thr Asp Ser
    130                 135                 140

Glu Tyr Gln Leu Pro Tyr Val Leu Gly Ser Ala His Gln Gly Cys Leu
145                 150                 155                 160

Pro Pro Phe Pro Ala Asp Val Phe Met Val Pro Gln Tyr Gly Tyr Leu
                165                 170                 175

Thr Leu Asn Asn Gly Ser Gln Ala Val Gly Arg Ser Ser Phe Tyr Cys
            180                 185                 190

Leu Glu Tyr Phe Pro Ser Gln Met Leu Arg Thr Gly Asn Asn Phe Thr
        195                 200                 205

Phe Ser Tyr Thr Phe Glu Asp Val Pro Phe His Ser Ser Tyr Ala His
    210                 215                 220

Ser Gln Ser Leu Asp Arg Leu Met Asn Pro Leu Ile Asp Gln Tyr Leu
225                 230                 235                 240

Tyr Tyr Leu Ser Arg Thr Asn Thr Pro Ser Gly Thr Thr Thr Gln Ser
                245                 250                 255

Arg Leu Gln Phe Ser Gln Ala Gly Ala Ser Asp Ile Arg Asp Gln Ser
            260                 265                 270

Arg Asn Trp Leu Pro Gly Pro Cys Tyr Arg Gln Gln Arg Val Ser Lys
        275                 280                 285

Thr Ser Ala Asp Asn Asn Ser Glu Tyr Ser Trp Thr Gly Ala Thr
    290                 295                 300

Lys Tyr His Leu Asn Gly Arg Asp Ser Leu Val Asn Pro Gly Pro Ala
305                 310                 315                 320

Met Ala Ser His Lys Asp Asp Glu Glu Lys Phe Phe Pro Gln Ser Gly
                325                 330                 335

Val Leu Ile Phe Gly Lys Gln Gly Ser Glu Lys Thr Asn Val Asp Ile
```

-continued

```
                340                 345                 350
Glu Lys Val Met Ile Thr Asp Glu Glu Ile Arg Thr Thr Asn Pro
        355                 360                 365
Val Ala Thr Glu Gln Tyr Gly Ser Val Ser Thr Asn Leu Gln Arg Gly
        370                 375                 380
Asn Arg Gln Ala Ala Thr Ala Asp Val Asn Thr Gln Gly Val Leu Pro
385                 390                 395                 400
Gly Met Val Trp Gln Asp Arg Asp Val Tyr Leu Gln Gly Pro Ile Trp
                405                 410                 415
Ala Lys Ile Pro His Thr Asp Gly His Phe His Pro Ser Pro Leu Met
        420                 425                 430
Gly Gly Phe Gly Leu Lys His Pro Pro Pro Gln Ile Leu Ile Lys Asn
        435                 440                 445
Thr Pro Val Pro Ala Asn Pro Ser Thr Thr Phe Ser Ala Ala Lys Phe
        450                 455                 460
Ala Ser Phe Ile Thr Gln Tyr Ser Thr Gly Gln Val Ser Val Glu Ile
465                 470                 475                 480
Glu Trp Glu Leu Gln Lys Glu Asn Ser Lys Arg Trp Asn Pro Glu Ile
                485                 490                 495
Gln Tyr Thr Ser Asn Tyr Asn Lys Ser Val Asn Val Asp Phe Thr Val
        500                 505                 510
Asp Thr Asn Gly Val Tyr Ser Glu Pro Arg Pro Ile Gly Thr Arg Tyr
        515                 520                 525
Leu Thr Arg Asn Leu
        530

<210> SEQ ID NO 16
<211> LENGTH: 6
<212> TYPE: PRT
<213> ORGANISM: Artificial sequence
<220> FEATURE:
<223> OTHER INFORMATION: Synthetic Bovine Papilloma Virus peptide

<400> SEQUENCE: 16

Thr Pro Phe Tyr Leu Lys
1               5

<210> SEQ ID NO 17
<211> LENGTH: 10
<212> TYPE: PRT
<213> ORGANISM: Artificial sequence
<220> FEATURE:
<223> OTHER INFORMATION: Synthetic Luteinizing Hormone Peptide

<400> SEQUENCE: 17

His Cys Ser Thr Cys Tyr Tyr His Lys Ser
1               5                   10

<210> SEQ ID NO 18
<211> LENGTH: 5
<212> TYPE: PRT
<213> ORGANISM: Artificial sequence
<220> FEATURE:
<223> OTHER INFORMATION: Synthetic targeting peptide

<400> SEQUENCE: 18

Phe Val Phe Lys Pro
1               5

<210> SEQ ID NO 19
```

<211> LENGTH: 4718
<212> TYPE: DNA
<213> ORGANISM: Adeno-associated virus 1

<400> SEQUENCE: 19

```
ttgcccactc cctctctgcg cgctcgctcg ctcggtgggg cctgcggacc aaaggtccgc      60
agacggcaga gctctgctct gccggcccca ccgagcgagc gagcgcgcag agagggagtg     120
ggcaactcca tcactagggg taatcgcgaa gcgcctccca cgctgccgcg tcagcgctga     180
cgtaaattac gtcataggggg agtggtcctg tattagctgt cacgtgagtg cttttgcgac     240
attttgcgac accacgtggc catttagggt atatatggcc gagtgagcga gcaggatctc     300
cattttgacc gcgaaatttg aacgagcagc agccatgccg ggcttctacg agatcgtgat     360
caaggtgccg agcgacctgg acgagcacct gccgggcatt tctgactcgt ttgtgagctg     420
ggtggccgag aaggaatggg agctgccccc ggattctgac atggatctga atctgattga     480
gcaggcaccc ctgaccgtgg ccgagaagct gcagcgcgag ttcctggtcc aatggcgccg     540
cgtgagtaag gccccggagg ccctcttctt tgttcagttc gagaagggcg agtcctactt     600
ccacctccat attctggtgg agaccacggg ggtcaaatcc atggtgctgg ccgcttcct      660
gagtcagatt agggacaagc tggtgcagac catctaccgc gggatcgagc cgaccctgcc     720
caactggttc gcggtgacca agacgcgtaa tggcgccgga gggggaaca aggtggtgga     780
cgagtgctac atccccaact acctcctgcc caagactcag cccgagctgc agtgggcgtg     840
gactaacatg gaggagtata taagcgcctg tttgaacctg gccgagcgca acggctcgt      900
ggcgcagcac ctgacccacg tcagccagac ccaggagcag aacaaggaga tctgaaccc     960
caattctgac gcgcctgtca tccggtcaaa aacctccgcg cgctacatgg agctggtcgg    1020
gtggctggtg gaccggggca tcacctccga gaagcagtgg atccaggagg accaggcctc    1080
gtacatctcc ttcaacgccg cttccaactc gcggtcccag atcaaggcgc tctggacaa    1140
tgccggcaag atcatggcgc tgaccaaatc cgcgcccgac tacctggtag gccccgctcc    1200
gccccgcgggac attaaaacca accgcatcta ccgcatcctg gagctgaacg gctacgaacc    1260
tgcctacgcc ggctccgtct tctctcggctg ggcccagaaa aggttcggga agcgcaacac    1320
catctggctg tttgggccgg ccaccacggg caagaccaac atcgcggaag ccatcgccca    1380
cgccgtgccc ttctacggct gcgtcaactg gaccaatgag aactttccct tcaatgattg    1440
cgtcgacaag atggtgatct ggtgggagga gggcaagatg acggccaagg tcgtggagtc    1500
cgccaaggcc attctcggcg gcagcaaggt gcgcgtggac caaaagtgca gtcgtccgc    1560
ccagatcgac cccaccccg tgatcgtcac ctccaacacc aacatgtgcg ccgtgattga    1620
cgggaacagc accaccttcg agcaccagca gccgttgcag gaccggatgt tcaaatttga    1680
actcacccgc cgtctggagc atgactttgg caaggtgaca aagcaggaag tcaaagagtt    1740
cttccgctgg gcgcaggatc acgtgaccga ggtggcgcat gagttctacg tcagaaaggg    1800
tggagccaac aaaagacccg ccccgatga cgccgggaaa agcgagccca gcgggcctg    1860
cccctcagtc gcggatccat cgacgtcaga cgcggaagga ctccggtgg acttgccga    1920
caggtaccaa aacaaatgtt ctcgtcacgc gggcatgctt cagatgctgt ttcctgcaa    1980
gacatgcgag agaatgaatc agaatttcaa catttgcttc acgcacggga cgagagactg    2040
ttcagagtgc ttccccggcg tgtcagaatc tcaaccggtc gtcagaaaga ggacgtatcg    2100
gaaactctgt gccattcatc atctgctggg gcgggctccc gagattgctt gctcggcctg    2160
cgatctggtc aacgtggacc tggatgactg tgtttctgag caataaatga cttaaaccag    2220
```

```
gtatggctgc cgatggttat cttccagatt ggctcgagga caacctctct gagggcattc    2280
gcgagtggtg ggacttgaaa cctggagccc cgaagcccaa agccaaccag caaaagcagg    2340
acgacggccg gggtctggtg cttcctggct acaagtacct cggacccttc aacggactcg    2400
acaaggggga gcccgtcaac gcggcggacg cagcggccct cgagcacgac aaggcctacg    2460
accagcagct caaagcgggt gacaatccgt acctgcggta taaccacgcc gacgccgagt    2520
ttcaggagcg tctgcaagaa gatacgtctt ttgggggcaa cctcgggcga gcagtcttcc    2580
aggccaagaa gcgggttctc gaacctctcg gtctggttga ggaaggcgct aagacggctc    2640
ctggaaagaa acgtccggta gagcagtcgc cacaagagcc agactcctcc tcgggcatcg    2700
gcaagacagg ccagcagccc gctaaaaaga gactcaattt tggtcagact ggcgactcag    2760
agtcagtccc cgatccacaa cctctcggag aacctccagc aaccccgct gctgtgggac     2820
ctactacaat ggcttcaggc ggtggcgcac caatggcaga caataacgaa ggcgccgacg    2880
gagtgggtaa tgcctcagga aattggcatt gcgattccac atggctgggc gacagagtca    2940
tcaccaccag cacccgcacc tgggccttgc ccacctacaa taaccacctc tacaagcaaa    3000
tctccagtgc ttcaacgggg gccagcaacg acaaccacta cttcggctac agcaccccct    3060
gggggtattt tgatttcaac agattccact gccacttttc accacgtgac tggcagcgac    3120
tcatcaacaa caattgggga ttccggccca agagactcaa cttcaaactc ttcaacatcc    3180
aagtcaagga ggtcacgacg aatgatggcg tcacaaccat cgctaataac cttaccagca    3240
cggttcaagt cttctcggac tcggagtacc agcttcgta cgtcctcggc tctgcgcacc     3300
agggctgcct ccctccgttc ccggcggacg tgttcatgat ccgcaatac ggctacctga     3360
cgctcaacaa tggcagccaa gccgtgggac gttcatcctt ttactgcctg gaatatttcc    3420
cttctcagat gctgagaacg ggcaacaact ttaccttcag ctacaccttt gaggaagtgc    3480
cttttccacag cagctacgcg cacagccaga gcctggaccg gctgatgaat cctctcatcg    3540
accaatacct gtattacctg aacagaactc aaaatcagtc cggaagtgcc caaaacaagg    3600
acttgctgtt tagccgtggg tctccagctg gcatgtctgt tcagcccaaa aactggctac    3660
ctggaccctg ttatcggcag cagcgcgttt ctaaaacaaa aacagacaac aacaacagca    3720
attttacctg gactggtgct tcaaaatata acctcaatgg gcgtgaatcc atcatcaacc    3780
ctggcactgc tatggcctca cacaaagacg acgaagacaa gttctttccc atgagcggtg    3840
tcatgatttt tggaaaagag agcgccggag cttcaaacac tgcattggac aatgtcatga    3900
ttacagacga agaggaaatt aaagccacta accctgtggc caccgaaaga tttgggaccg    3960
tggcagtcaa tttccagagc agcagcacag accctgcgac cggagatgtg catgctatgg    4020
gagcattacc tggcatggtg tggcaagata gagacgtgta cctgcagggt cccatttggg    4080
ccaaaattcc tcacacagat ggacactttc cccgtctcc tcttatgggc ggctttggac      4140
tcaagaaccc gcctcctcag atcctcatca aaaacacgcc tgttcctgcg aatcctccgg    4200
cggagttttc agctacaaag tttgcttcat tcatcaccca atactccaca ggacaagtga    4260
gtgtggaaat tgaatgggag ctgcagaaag aaaacagcaa gcgctggaat cccgaagtgc    4320
agtacacatc caattatgca aaatctgcca acgttgattt tactgtggac aacaatggac    4380
tttatactga gcctcgcccc attggcaccc gttaccttac ccgtcccctg taattacgtg    4440
ttaatcaata aaccggttga ttcgtttcag ttgaactttg gtctcctgtc cttcttatct    4500
tatcggttac catggttata gcttacacat taactgcttg gttgcgcttc gcgataaaag    4560
```

```
acttacgtca tcgggttacc cctagtgatg gagttgccca ctccctctct gcgcgctcgc    4620
tcgctcggtg gggcctgcgg accaaaggtc cgcagacggc agagctctgc tctgccggcc    4680
ccaccgagcg agcgagcgcg cagagaggga gtgggcaa                            4718
```

```
<210> SEQ ID NO 20
<211> LENGTH: 736
<212> TYPE: PRT
<213> ORGANISM: Adeno-associated virus 1

<400> SEQUENCE: 20
```

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350
```

```
Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
            405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
            485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
            565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
            725                 730                 735

<210> SEQ ID NO 21
<211> LENGTH: 4722
<212> TYPE: DNA
<213> ORGANISM: Adeno associate virus 3
```

<400> SEQUENCE: 21

```
tggccactcc ctctatgcgc actcgctcgc tcggtggggc ctggcgacca aaggtcgcca      60
gacggacgtg cttttgcacgt ccggccccac cgagcgagcg agtgcgcata gagggagtgg    120
ccaactccat cactagaggt atggcagtga cgtaacgcga agcgcgcgaa gcgagaccac    180
gcctaccagc tgcgtcagca gtcaggtgac ccttttgcga cagtttgcga caccacgtgg    240
ccgctgaggg tatatattct cgagtgagcg aaccaggagc tccattttga ccgcgaaatt    300
tgaacgagca gcagccatgc cggggttcta cgagattgtc ctgaaggtcc cgagtgacct    360
ggacgagcac ctgccgggca tttctaactc gtttgttaac tgggtggccg agaaggaatg    420
ggagctgccg ccggattctg acatggatcc gaatctgatt gagcaggcac ccctgaccgt    480
ggccgaaaag cttcagcgcg agttcctggt ggagtggcgc cgcgtgagta aggccccgga    540
ggccctcttt tttgtccagt tcgaaaaggg ggagacctac ttccacctgc acgtgctgat    600
tgagaccatc ggggtcaaat ccatggtggt cggccgctac gtgagccaga ttaaagagaa    660
gctggtgacc cgcatctacc gcggggtcga gccgcagctt ccgaactggt tcgcggtgac    720
caaaacgcga aatggcgccg ggggcgggaa caaggtggtg gacgactgct acatccccaa    780
ctacctgctc cccaagaccc agcccgagct ccagtgggcg tggactaaca tggaccagta    840
tttaagcgcg tgtttgaatc tcgcggacgg taaacggctg gtggcgcagc atctgacgca    900
cgtgtcgcag acgcaggagc agaacaaaga gaatcagaac cccaattctg acgcgccggt    960
catcaggtca aaaaccctcag ccaggtacat ggagctggtc gggtggctgg tggaccgcgg   1020
gatcacgtca gaaaagcaat ggattcagga ggaccaggcc tcgtacatct ccttcaacgc   1080
cgcctccaac tcgcggtccc agatcaaggc cgcgctggac aatgcctcca agatcatgag   1140
cctgacaaag acggctccgg actacctggt gggcagcaac ccgccggagg acattaccaa   1200
aaatcggatc taccaaatcc tggagctgaa cgggtacgat ccgcagtacg cggcctccgt   1260
cttcctgggc tgggcgcaaa agaagttcgg gaagaggaac accatctggc tctttgggcc   1320
ggccacgacg ggtaaaaacca acatcgcgga agccatcgcc cacgccgtgc ccttctacgg   1380
ctgcgtaaac tggaccaatg agaactttcc cttcaacgat tgcgtcgaca agatggtgat   1440
ctggtgggag gagggcaaga tgacggccaa ggtcgtggag agcgccaagg ccattctggg   1500
cggaagcaag gtgcgcgtgg accaaaagtg caagtcatcg gcccagatcg aacccactcc   1560
cgtgatcgtc acctccaaca ccaacatgtg cgccgtgatt gacgggaaca gcaccacctt   1620
cgagcatcag cagccgctgc aggaccggat gttaaatttt gaacttaccc gccgttggga   1680
ccatgacttt gggaaggtca ccaaacagga agtaaaggac ttttccggt gggcttccga   1740
tcacgtgact gacgtggctc atgagttcta cgtcagaaaa ggtggagcta agaaacgccc   1800
cgcctccaat gacgcggatg taagcgagcc aaaacggcag tgcacgtcac ttgcgcagcc   1860
gacaacgtca gacgcggaag caccggcgga ctacgcggac aggtaccaaa acaaatgttc   1920
tcgtcacgtg ggcatgaatc tgatgctttt tccctgtaaa acatgcgaga gatgaatca   1980
aatttccaat gtctgtttta cgcatggtca aagagactgt ggggaatgct tccctggaat   2040
gtcagaatct caacccgttt ctgtcgtcaa aagaagact tatcagaaac tgtgtccaat   2100
tcatcatatc ctgggaaggg cacccgagat tgcctgttcg gcctgcgatt tggccaatgt   2160
ggacttggat gactgtgttt ctgagcaata aatgacttaa accaggtatg gctgctgacg   2220
gttatcttcc agattggctc gaggacaacc tttctgaagg cattcgtgag tggtgggctc   2280
tgaaacctgg agtccctcaa cccaaagcga accaacaaca ccaggacaac cgtcggggtc   2340
```

```
ttgtgcttcc gggttacaaa tacctcggac ccggtaacgg actcgacaaa ggagagccgg   2400
tcaacgaggc ggacgcggca gccctcgaac acgacaaagc ttacgaccag cagctcaagg   2460
ccggtgacaa cccgtacctc aagtacaacc acgccgacgc cgagtttcag gagcgtcttc   2520
aagaagatac gtcttttggg ggcaaccttg gcagagcagt cttccaggcc aaaaagagga   2580
tccttgagcc tcttggtctg gttgaggaag cagctaaaac ggctcctgga agaagaggc    2640 ctgtagatca gtctcctcag gaaccggact catcatctgg tgttggcaaa tcgggcaaac   2700
agcctgccag aaaaagacta aatttcggtc agactggcga ctcagagtca gtcccagacc   2760
ctcaacctct cggagaacca ccagcagccc ccacaagttt gggatctaat acaatggctt   2820
caggcggtgg cgcaccaatg gcagacaata cgagggtgc cgatggagtg ggtaattcct    2880
caggaaattg gcattgcgat tcccaatggc tgggcgacag agtcatcacc accagcacca   2940
gaacctgggc cctgcccact acaacaacc atctctacaa gcaaatctcc agccaatcag    3000
gagcttcaaa cgacaaccac tactttggct acagcacccc ttgggggtat tttgacttta   3060
acagattcca ctgccacttc tcaccacgtg actggcagcg actcattaac aacaactggg   3120
gattccggcc caagaaactc agcttcaagc tcttcaacat ccaagttaaa gaggtcacgc   3180
agaacgatgg cacgacgact attgccaata accttaccag cacggttcaa gtgtttacgg   3240
actcggagta tcagctcccg tacgtgctcg gtcggcgca ccaaggctgt ctcccgccgt    3300
ttccagcgga cgtcttcatg gtccctcagt atggatacct cacccctgaac aacggaagtc   3360 aagcggtggg acgctcatcc ttttactgcc tggagtactt cccttcgcag atgctaagga   3420
ctggaaataa cttccaattc agctatacct tcgaggatgt accttttcac agcagctacg   3480
ctcacagcca gagtttggat cgcttgatga atcctcttat tgatcagtat ctgtactacc   3540
tgaacagaac gcaaggaaca acctctggaa caaccaacca atcacggctg cttttttagcc  3600 aggctgggcc tcagtctatg tctttgcagg ccagaaattg gctacctggg ccctgctacc   3660
ggcaacagag actttcaaag actgctaacg acaacaacaa cagtaacttt ccttggacag   3720
cggccagcaa atatcatctc aatggccgcg actcgctggt gaatccagga ccagctatgg   3780
ccagtcacaa ggacgatgaa gaaaaatttt tccctatgca cggcaatcta atatttggca   3840
aagaagggac aacggcaagt aacgcagaat tagataatgt aatgattacg gatgaagaag   3900
agattcgtac caccaatcct gtggcaacag agcagtatgg aactgtggca ataacttgc    3960 agagctcaaa tacagctccc acgactagaa ctgtcaatga tcaggggcc ttacctggca    4020 tggtgtggca agatcgtgac gtgtaccttc aaggacctat ctgggcaaag attcctcaca   4080 cggatgaca ctttcatcct tctcctctga tgggaggctt tggactgaaa catccgcctc    4140
ctcaaatcat gatcaaaaat actccggtac cggcaaatcc tccgacgact ttcagcccgg   4200
ccaagtttgc ttcatttatc actcagtact ccactggaca ggtcagcgtg gaaattgagt   4260
gggagctaca gaaagaaaac agcaaacgtt ggaatccaga gattcagtac acttccaact   4320
acaacaagtc tgttaatgtg gactttactg tagacactaa tggtgtttat agtgaacctc   4380
gccctattgg aacccggtat ctcacacgaa acttgtaatc ctggttaatc aataaaccgt   4440
ttaattcgtt tcagttgaac tttggctctt gtgcacttct tatcttatct tgtttccatg   4500
gctactgcgt agataagcag cggcctgcgg cgcttgcgct tcgcggttta caactgctgg   4560
ttaatattta actctcgcca tacctctagt gatggagttg gccactccct ctatgcgcac   4620
tcgctcgctc ggtggggccg gacgtgcaaa gcacgtccgt ctggcgacct ttggtcgcca   4680
```
ggccccaccg agcgagcgag tgcgcataga gggagtggcc aa        4722

<210> SEQ ID NO 22
<211> LENGTH: 736
<212> TYPE: PRT
<213> ORGANISM: Adeno-associated virus 3

<400> SEQUENCE: 22

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 23
<211> LENGTH: 4767
<212> TYPE: DNA
<213> ORGANISM: Adeno-associated virus 4

<400> SEQUENCE: 23
ttggccactc cctctatgcg cgctcgctca ctcactcggc cctggagacc aaaggtctcc        60

```
agactgccgg cctctggccg gcagggccga gtgagtgagc gagcgcgcat agagggagtg     120
gccaactcca tcatctaggt ttgcccactg acgtcaatgt gacgtcctag ggttagggag     180
gtccctgtat tagcagtcac gtgagtgtcg tatttcgcgg agcgtagcgg agcgcatacc     240
aagctgccac gtcacagcca cgtggtccgt ttgcgacagt ttgcgacacc atgtggtcag     300
gagggtatat aaccgcgagt gagccagcga ggagctccat tttgcccgcg aattttgaac     360
gagcagcagc catgccgggg ttctacgaga tcgtgctgaa ggtgcccagc gacctggacg     420
agcacctgcc cggcatttct gactcttttg tgagctgggt ggccgagaag gaatgggagc     480
tgccgccgga ttctgacatg gacttgaatc tgattgagca ggcacccctg accgtggccg     540
aaaagctgca acgcgagttc ctggtcgagt ggcgccgcgt gagtaaggcc ccggaggccc     600
tcttctttgt ccagttcgag aagggggaca gctacttcca cctgcacatc ctggtggaga     660
ccgtgggcgt caaatccatg gtggtgggcc gctacgtgag ccagattaaa gagaagctgg     720 tgaccgcat ctaccgcggg gtcgagccgc agcttccgaa ctggttcgcg gtgaccaaga     780
cgcgtaatgg cgccggaggc gggaacaagg tggtggacga ctgctacatc cccaactacc     840
tgctccccaa gacccagccc gagctccagt gggcgtggac taacatggac cagtatataa     900
gcgcctgttt gaatctcgcg gagcgtaaac ggctggtggc gcagcatctg acgcacgtgt     960
cgcagacgca ggagcagaac aaggaaaacc agaaccccaa ttctgacgcg ccggtcatca    1020
ggtcaaaaac ctccgccagg tacatggagc tggtcgggtg gctggtggac cgcgggatca    1080
cgtcagaaaa gcaatggatc caggaggacc aggcgtccta catctccttc aacgccgcct    1140
ccaactcgcg gtcacaaatc aaggccgcgc tggacaatgc ctccaaaatc atgagcctga    1200
caaagacggc tccggactac ctggtgggcc agaacccgcc ggaggacatt tccagcaacc    1260
gcatctaccg aatcctcgag atgaacgggt acgatccgca gtacgcggcc tccgtcttcc    1320
tgggctgggc gcaaaagaag ttcgggaaga ggaacaccat ctggctcttt gggccggcca    1380
cgacgggtaa aaccaacatc gcggaagcca tcgcccacgc cgtgcccttc tacggctgcg    1440
tgaactggac caatgagaac tttccgttca acgattgcgt cgacaagatg gtgatctggt    1500
gggaggaggg caagatgacg gccaaggtcg tagagagcgc caaggccatc ctgggcggaa    1560
gcaaggtgcg cgtggaccaa aagtgcaagt catcggccca gatcgaccca actcccgtga    1620
tcgtcacctc caacaccaac atgtgcgcgg tcatcgacgg aaactcgacc accttcgagc    1680
accaacaacc actccaggac cggatgttca agttcgagct caccaagcgc ctggagcacg    1740
actttggcaa ggtcaccaag caggaagtca agactttttt ccggtgggcg tcagatcacg    1800
tgaccgaggt gactcacgag ttttacgtca gaaagggtgg agctagaaag aggcccgccc    1860
ccaatgacgc agatataagt gagcccaagc gggcctgtcc gtcagttgcg cagccatcga    1920
cgtcagacgc ggaagctccg gtggactacg cggacaggta ccaaaacaaa tgttctcgtc    1980
acgtgggtat gaatctgatg cttttttccct gccggcaatg cgagagaatg aatcagaatg    2040
tggacatttg cttcacgcac ggggtcatgg actgtgccga gtgcttcccc gtgtcagaat    2100
ctcaacccgt gtctgtcgtc agaaagcgga cgtatcagaa actgtgtccg attcatcaca    2160
tcatggggag gcgcccgag gtggcctgct cggcctgcga actggccaat gtggacttgg    2220
atgactgtga catggaacaa taaatgacta aaaccagata tgactgacgg ttaccttcca    2280
gattggctag aggacaacct ctctgaaggc gttcgagagt ggtgggcgct gcaacctgga    2340
gcccctaaac ccaaggcaaa tcaacaacat caggacaacg ctcggggtct tgtgcttccg    2400
ggttacaaat acctcggacc cggcaacgga ctcgacaagg gggaacccgt caacgcagcg    2460
```

```
gacgcggcag ccctcgagca cgacaaggcc tacgaccagc agctcaaggc cggtgacaac    2520
ccctacctca agtacaacca cgccgacgcg gagttccagc agcggcttca gggcgacaca    2580
tcgtttgggg gcaacctcgg cagagcagtc ttccaggcca aaagagggt tcttgaacct    2640 cttggtctgg ttgagcaagc gggtgagacg gctcctggaa agaagagacc gttgattgaa    2700
tccccccagc agcccgactc ctccacgggt atcggcaaaa aaggcaagca gccggctaaa    2760
aagaagctcg ttttcgaaga cgaaactgga gcaggcgacg gaccccctga gggatcaact    2820
tccggagcca tgtctgatga cagtgagatg cgtgcagcag ctggcggagc tgcagtcgag    2880
ggcggacaag gtgccgatgg agtgggtaat gcctcgggtg attggcattg cgattccacc    2940
tggtctgagg gccacgtcac gaccaccagc accagaacct gggtcttgcc cacctacaac    3000
aaccacctct acaagcgact cggagagagc ctgcagtcca cacctacaa cggattctcc    3060 accccctggg gatactttga cttcaaccgc ttccactgcc acttctcacc acgtgactgg    3120
cagcgactca tcaacaacaa ctgggggcatg cgacccaaag ccatgcgggt caaaatcttc    3180
aacatccagg tcaaggaggt cacgacgtcg aacggcgaga caacggtggc taataacctt    3240
accagcacgg ttcagatctt tgcggactcg tcgtacgaac tgccgtacgt gatggatgcg    3300
ggtcaagagg gcagcctgcc tccttttccc aacgacgtct ttatggtgcc ccagtacggc    3360
tactgtggac tggtgaccgg caacacttcg cagcaacaga ctgacagaaa tgccttctac    3420
tgcctggagt actttccttc gcagatgctg cggactggca acaactttga aattacgtac    3480
agttttgaga aggtgccttt ccactcgatg tacgcgcaca gccagagcct ggaccggctg    3540
atgaaccctc tcatcgacca gtacctgtgg ggactgcaat cgaccaccac cggaaccacc    3600
ctgaatgccg ggactgccac caccaacttt accaagctgc ggcctaccaa cttttccaac    3660
tttaaaaaga actggctgcc cgggccttca atcaagcagc agggcttctc aaagactgcc    3720
aatcaaaact acaagatccc tgccaccggg tcagacagtc tcatcaaata cgagacgcac    3780
agcactctgg acggaagatg gagtgccctg acccccggac ctccaatggc cacggctgga    3840
cctgcggaca gcaagttcag caacagccag ctcatctttg cggggcctaa acagaacggc    3900
aacacggcca ccgtacccgg gactctgatc ttcaccctctg aggaggagct ggcagccacc    3960
aacgccaccg atacggacat gtgggggcaac ctacctggcg gtgaccagag caacagcaac    4020
ctgccgaccg tggacagact gacagccttg ggagccgtgc ctggaatggt ctggcaaaac    4080
agagacattt actaccaggg tcccatttgg gccaagattc ctcataccga tggacacttt    4140 caccccctcac cgctgattgg tgggtttggg ctgaaacacc cgcctcctca aattttatc    4200 aagaacaccc cggtacctgc gaatcctgca acgaccttca gctctactcc ggtaaactcc    4260
ttcattactc agtacagcac tggccaggtg tcggtgcaga ttgactggga gatccagaag    4320
gagcggtcca acgctggaa ccccgaggtc cagtttacct ccaactacgg acagcaaaac    4380
tctctgttgt gggctcccga tgcggctggg aaatacactg agcctagggc tatcggtacc    4440
cgctacctca cccaccacct gtaataacct gttaatcaat aaaccggttt attcgtttca    4500
gttgaacttt ggtctccgtg tccttcttat cttatctcgt ttccatggct actgcgtaca    4560
taagcagcgg cctgcggcgc ttgcgcttcg cggtttacaa ctgccggtta atcagtaact    4620
tctggcaaac cagatgatgg agttggccac attagctatg cgcgctcgct cactcactcg    4680 gcccctggaga ccaaaggtct ccagactgcc ggcctctggc cggcagggcc gagtgagtga    4740
gcgagcgcgc atagagggag tggccaa                                       4767
```

<210> SEQ ID NO 24
<211> LENGTH: 734
<212> TYPE: PRT
<213> ORGANISM: Adeno-associated virus 4

<400> SEQUENCE: 24

```
Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
        35                  40                  45

Tyr Lys Tyr Leu Gly Pro Gly Asn Gly Leu Asp Lys Gly Glu Pro Val
    50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
    130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Ala Gly Gly Ala Ala Val Glu Gly
        195                 200                 205

Gly Gln Gly Ala Asp Gly Val Gly Asn Ala Ser Gly Asp Trp His Cys
    210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Gln Thr Asp Arg Asn
    370                 375                 380
```

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
            405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Gly Thr Thr Leu
            435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
            485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
515                 520                 525

Ala Asp Ser Lys Phe Ser Asn Ser Gln Leu Ile Phe Ala Gly Pro Lys
530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
            565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
595                 600                 605

Asp Ile Tyr Tyr Gln Gly Pro Ile Trp Ala Lys Ile Pro His Thr Asp
610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
            645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
            675                 680                 685

Arg Ser Lys Arg Trp Asn Pro Glu Val Gln Phe Thr Ser Asn Tyr Gly
            690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
            725                 730

<210> SEQ ID NO 25
<211> LENGTH: 4683
<212> TYPE: DNA
<213> ORGANISM: Adeno-associate virus 6

<400> SEQUENCE: 25
ttggccactc cctctctgcg cgctcgctcg ctcactgagg ccgggcgacc aaaggtcgcc    60
cgacgcccgg gctttgcccg gcggcctca gtgagcgagc gagcgcgcag agagggagtg   120

-continued

| | |
|---|---|
| gccaactcca tcactagggg ttcctggagg ggtggagtcg tgacgtgaat tacgtcatag | 180 |
| ggttagggag gtcctgtatt agaggtcacg tgagtgtttt gcgacatttt gcgacaccat | 240 |
| gtggtcacgc tgggtattta agcccgagtg agcacgcagg gtctccattt tgaagcggga | 300 |
| ggtttgaacg cgcagcgcca tgccggggtt ttacgagatt gtgattaagg tccccagcga | 360 |
| ccttgacgag catctgcccg gcatttctga cagctttgtg aactgggtgg ccgagaagga | 420 |
| atgggagttg ccgccagatt ctgacatgga tctgaatctg attgagcagg cacccctgac | 480 |
| cgtggccgag aagctgcagc gcgacttcct ggtccagtgg cgccgcgtga gtaaggcccc | 540 |
| ggaggccctc ttctttgttc agttcgagaa gggcgagtcc tacttccacc tccatattct | 600 |
| ggtggagacc acggggtca atccatggt gctgggccgc ttcctgagtc agattaggga | 660 |
| caagctggtg cagaccatct accgcgggat cgagccgacc ctgcccaact ggttcgcggt | 720 |
| gaccaagacg cgtaatggcg ccggaggggg gaacaaggtg gtggacgagt gctacatccc | 780 |
| caactacctc ctgcccaaga ctcagcccga gctgcagtgg gcgtggacta acatggagga | 840 |
| gtatataagc gcgtgtttaa acctggccga gcgcaaacgg ctcgtggcgc acgacctgac | 900 |
| ccacgtcagc cagacccagg agcagaacaa ggagaatctg aaccccaatt ctgacgcgcc | 960 |
| tgtcatccgg tcaaaaacct ccgcacgcta catggagctg gtcgggtggc tggtggaccg | 1020 |
| gggcatcacc tccgagaagc agtggatcca ggaggaccag gcctcgtaca tctccttcaa | 1080 |
| cgccgcctcc aactcgcggt cccagatcaa ggccgctctg acaatgccg gcaagatcat | 1140 |
| ggcgctgacc aaatccgcgc ccgactacct ggtaggcccc gctccgcccg ccgacattaa | 1200 |
| aaccaaccgc atttaccgca tcctggagct gaacggctac gaccctgcct acgccggctc | 1260 |
| cgtcttctc ggctgggccc agaaaaggtt cggaaaacgc aacaccatct ggctgtttgg | 1320 |
| gccggccacc acgggcaaga ccaacatcgc ggaagccatc gcccacgccg tgcccttcta | 1380 |
| cggctgcgtc aactgaccca atgagaactt tcccttcaac gattgcgtcg acaagatggt | 1440 |
| gatctggtgg gaggagggca agatgacggc caaggtcgtg gagtccgcca aggccattct | 1500 |
| cggcggcagc aaggtgcgcg tggaccaaaa gtgcaagtcg tccgcccaga tcgatcccac | 1560 |
| ccccgtgatc gtcacctcca acaccaacat gtgcgccgtg attgacggga acagcaccac | 1620 |
| cttcgagcac cagcagccgt tgcaggaccg gatgttcaaa tttgaactca cccgccgtct | 1680 |
| ggagcatgac tttggcaagg tgacaaagca ggaagtcaaa gagttcttcc gctgggcgca | 1740 |
| ggatcacgtg accgaggtgg cgcatgagtt ctacgtcaga aagggtggag ccaacaagag | 1800 |
| acccgccccc gatgacgcgg ataaaagcga gcccaagcgg gcctgcccct cagtcgcgga | 1860 |
| tccatcgacg tcagcgcgg aaggagctcc ggtggacttt gccgacaggt accaaaacaa | 1920 |
| atgttctcgt cacgcgggca tgcttcagat gctgtttccc tgcaaaacat gcgagagaat | 1980 |
| gaatcagaat ttcaacattt gcttcacgca cgggaccaga gactgttcag aatgtttccc | 2040 |
| cggcgtgtca gaatctcaac cggtcgtcag aaagaggacg tatcggaaac tctgtgccat | 2100 |
| tcatcatctg ctggggcggg ctcccgagat tgcttgctcg cctgcgatc tggtcaacgt | 2160 |
| ggatctggat gactgtgttt ctgagcaata aatgacttaa accaggtatg gctgccgatg | 2220 |
| gttatcttcc agattggctc gaggacaacc tctctgaggg cattcgcgag tggtgggact | 2280 |
| tgaaacctgg agcccgaaa cccaaagcca accagcaaaa gcaggacgac ggccggggtc | 2340 |
| tggtgcttcc tggctacaag tacctcggac ccttcaacgg actcgacaag ggggagcccg | 2400 |
| tcaacgcggc ggatgcagcg gccctcgagc acgacaaggc ctacgaccag cagctcaaag | 2460 |
| cgggtgacaa tccgtacctg cggtataacc acgccgacgc cgagtttcag gagcgtctgc | 2520 |

```
aagaagatac gtcttttggg ggcaacctcg ggcgagcagt cttccaggcc aagaagaggg   2580
ttctcgaacc ttttggtctg gttgaggaag gtgctaagac ggctcctgga agaaacgtc    2640 cggtagagca gtcgccacaa gagccagact cctcctcggg cattggcaag acaggccagc   2700
agcccgctaa aaagagactc aattttggtc agactggcga ctcagagtca gtccccgacc   2760
cacaacctct cggagaacct ccagcaaccc ccgctgctgt gggacctact acaatggctt   2820
caggcggtgg cgcaccaatg cagacaata acgaaggcgc cgacggagtg ggtaatgcct    2880
caggaaattg gcattgcgat tccacatggc tgggcgacag agtcatcacc accagcaccc   2940
gaacatgggc cttgcccacc tataacaacc acctctacaa gcaaatctcc agtgcttcaa   3000
cgggggccag caacgacaac cactacttcg gctacagcac cccctggggg tattttgatt   3060
tcaacagatt ccactgccat ttctcaccac gtgactggca gcgactcatc aacaacaatt   3120
ggggattccg gcccaagaga ctcaacttca agctcttcaa catccaagtc aaggaggtca   3180
cgacgaatga tggcgtcacg accatcgcta ataaccttac cagcacggtt caagtcttct   3240
cggactcgga gtaccagttg ccgtacgtcc tcggctctgc gcaccagggc tgcctccctc   3300
cgttcccggc ggacgtgttc atgattccgc agtacggcta cctaacgctc aacaatggca   3360
gccaggcagt gggacggtca tccttttact gcctggaata tttcccatcg cagatgctga   3420
gaacgggcaa taactttacc ttcagctaca ccttcgagga cgtgccttc cacagcagct     3480 acgcgcacag ccagagcctg gaccggctga tgaatcctct catcgaccag tacctgtatt   3540
acctgaacag aactcagaat cagtccggaa gtgcccaaaa caaggacttg ctgtttagcc   3600
gggggtctcc agctggcatg tctgttcagc ccaaaaactg gctacctgga ccctgttacc   3660
ggcagcagcg cgtttctaaa acaaaaacag acaacaacaa cagcaacttt acctggactg   3720
gtgcttcaaa atataacctt aatgggcgtg aatctataat caaccctggc actgctatgg   3780 cctcacacaca agacgacaaa gacaagttct ttcccatgag cggtgtcatg attttttggaa  3840 aggagagcgc cggagcttca aacactgcat tggacaatgt catgatcaca gacgaagagg   3900
aaatcaaagc cactaaccc gtggccaccg aaagatttgg gactgtggca gtcaatctcc    3960
agagcagcag cacagaccct gcgaccggag atgtgcatgt tatgggagcc ttacctggaa   4020
tggtgtggca agacagagac gtatacctgc agggtcctat ttgggccaaa attcctcaca   4080
cggatggaca ctttcacccg tctcctctca tgggcggctt tggacttaag cacccgcctc    4140
ctcagatcct catcaaaaac acgcctgttc ctgcgaatcc tccggcagag ttttcggcta    4200
caaagtttgc ttcattcatc acccagtatt ccacaggaca agtgagcgtg gagattgaat   4260
gggagctgca gaaagaaaac agcaaacgct ggaatcccga agtgcagtat acatctaact   4320
atgcaaaatc tgccaacgtt gatttcactg tggacaacaa tggactttat actgagcctc   4380
gccccattgg cacccgttac ctcacccgtc cctgtaatt gtgtgttaat caataaaccg    4440
gttaattcgt gtcagttgaa ctttggtctc atgtcgttat tatcttatct ggtcaccata   4500
gcaaccggtt acacattaac tgcttagttg cgcttgcga ataccctag tgatggagtt     4560 gcccactccc tctatgcgcg ctcgctcgct cggtggggcc ggcagagcag agctctgccg    4620
tctgcggacc tttggtccgc aggccccacc gagcgagcga gcgcgcatag agggagtggg   4680
caa                                                                  4683

<210> SEQ ID NO 26
<211> LENGTH: 736
<212> TYPE: PRT
```

<213> ORGANISM: Adeno-associated virus 6

<400> SEQUENCE: 26

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65              70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

-continued

```
Ser Gln Met Leu Arg Thr Gly Asn Asn Phe Thr Ser Tyr Thr Phe
            405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
        450                 455                 460

Arg Gly Ser Pro Ala Gly Met Ser Val Gln Pro Lys Asn Trp Leu Pro
465                 470                 475                 480

Gly Pro Cys Tyr Arg Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
        530                 535                 540

Lys Glu Ser Ala Gly Ala Ser Asn Thr Ala Leu Asp Asn Val Met Ile
545                 550                 555                 560

Thr Asp Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
        690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735
```

<210> SEQ ID NO 27
<211> LENGTH: 5
<212> TYPE: PRT
<213> ORGANISM: Artificial sequence
<220> FEATURE:
<223> OTHER INFORMATION: Synthetic Peptide

<400> SEQUENCE: 27

```
Cys Asn Gly Arg Cys
1               5
```

<210> SEQ ID NO 28
<211> LENGTH: 7

```
<212> TYPE: PRT
<213> ORGANISM: Artificial sequence
<220> FEATURE:
<223> OTHER INFORMATION: Synthetic Peptide

<400> SEQUENCE: 28

Ala Thr Trp Leu Pro Pro Arg
1               5

<210> SEQ ID NO 29
<211> LENGTH: 7
<212> TYPE: PRT
<213> ORGANISM: Artificial sequence
<220> FEATURE:
<223> OTHER INFORMATION: Synthetic Peptide

<400> SEQUENCE: 29

Leu Pro Pro Asn Pro Thr Lys
1               5

<210> SEQ ID NO 30
<211> LENGTH: 7
<212> TYPE: PRT
<213> ORGANISM: Artificial sequence
<220> FEATURE:
<223> OTHER INFORMATION: Synthetic Peptide

<400> SEQUENCE: 30

Tyr Ala Ile Met Pro Leu Val
1               5

<210> SEQ ID NO 31
<211> LENGTH: 12
<212> TYPE: PRT
<213> ORGANISM: Artificial sequence
<220> FEATURE:
<223> OTHER INFORMATION: Synthetic Peptide

<400> SEQUENCE: 31

Met His Ser Asp Met His Ala Pro Val Ser Asp Ile
1               5                   10

<210> SEQ ID NO 32
<211> LENGTH: 12
<212> TYPE: PRT
<213> ORGANISM: Artificial sequence
<220> FEATURE:
<223> OTHER INFORMATION: Synthetic Peptide

<400> SEQUENCE: 32

His Thr Met Tyr Tyr His His Tyr Gln His His Leu
1               5                   10

<210> SEQ ID NO 33
<211> LENGTH: 8
<212> TYPE: PRT
<213> ORGANISM: Artificial sequence
<220> FEATURE:
<223> OTHER INFORMATION: Synthetic Peptide

<400> SEQUENCE: 33

Asn Leu Leu Met Ala Ala Ser Gly
1               5

<210> SEQ ID NO 34
<211> LENGTH: 8
<212> TYPE: PRT
```

<213> ORGANISM: Artificial sequence
<220> FEATURE:
<223> OTHER INFORMATION: Synthetic Peptide

<400> SEQUENCE: 34

His His His Arg His Ser Phe Gly
1               5

<210> SEQ ID NO 35
<211> LENGTH: 4642
<212> TYPE: DNA
<213> ORGANISM: Adeno-associated virus 5

<400> SEQUENCE: 35

```
ctctccccccc tgtcgcgttc gctcgctcgc tggctcgttt ggggggggtgg cagctcaaag    60
agctgccaga cgacggccct ctggccgtcg ccccccccaaa cgagccagcg agcgagcgaa   120
cgcgacaggg gggagagtgc cacactctca agcaaggggg ttttgtaagc agtgatgtca   180
taatgatgta atgcttattg tcacgcgata gttaatgatt aacagtcatg tgatgtgttt   240
tatccaatag gaagaaagcg cgcgtatgag ttctcgcgag acttccgggg tataaaagac   300
cgagtgaacg agcccgccgc cattctttgc tctggactgc tagaggaccc tcgctgccat   360
ggctaccttc tatgaagtca ttgttcgcgt cccatttgac gtggaggaac atctgcctgg   420
aatttctgac agctttgtgg actgggtaac tggtcaaatt tgggagctgc tccagagtc   480
agatttaaat ttgactctgg ttgaacagcc tcagttgacg gtggctgata gaattcgccg   540
cgtgttcctg tacgagtgga acaaattttc caagcaggag tccaaattct tgtgcagtt   600
tgaaaaggga tctgaatatt ttcatctgca cacgcttgtg gagacctccg gcatctcttc   660
catggtcctc ggccgctacg tgagtcagat tcgcgcccag ctggtgaaag tggtcttcca   720
gggaattgaa ccccagatca acgactgggt cgccatcacc aaggtaaaga agggcggagc   780
caataaggtg gtggattctg gtatattcc cgcctacctg ctgccgaagg tccaaccgga   840
gcttcagtgg gcgtggacaa acctggacga gtataaattg gccgccctga atctggagga   900
gcgcaaacgg ctcgtcgcgc agtttctggc agaatcctcg cagcgctcgc aggaggcggc   960
ttcgcagcgt gagttctcgg ctgacccggt catcaaaagc aagacttccc agaaatacat  1020
ggcgctcgtc aactggctcg tggagcacgg catcacttcc gagaagcagt ggatccagga  1080
aaatcaggag agctacctct ccttcaactc caccggcaac tctcggagcc agatcaaggc  1140
cgcgctcgac aacgcgacca aaattatgag tctgacaaaa agcgcggtgg actacctcgt  1200
ggggagctcc gttcccgagg acatttcaaa aaacagaatc tggcaaattt ttgagatgaa  1260
tggctacgac ccggcctacg cgggatccat cctctacggc tggtgtcagc gctccttcaa  1320
caagaggaac accgtctggc tctacggacc cgccacgacc ggcaagacca acatcgcgga  1380
ggccatcgcc cacactgtgc ccttttacgc ctgcgtgaac tggaccaatg aaaactttcc  1440
ctttaatgac tgtgtggaca aaatgctcat ttggtgggag gagggaaaga tgaccaacaa  1500
ggtggttgaa tccgccaagg ccatcctggg gggctcaaag gtgcgggtcg atcagaaatg  1560
taaatcctct gttcaaattg attctacccc tgtcattgta acttccaata caaacatgtg  1620
tgtggtggtg gatgggaatt ccacgacctt tgaacaccag cagccgctgg aggaccgcat  1680
gttcaaattt gaactgacta gcggctcccc gccagatttt ggcaagatta ctaagcagga  1740
agtcaaggac tttttttgctt gggcaaaggt caatcaggtg ccggtgactc acgagtttaa  1800
agttcccagg gaattggcgg gaactaaagg ggcggagaaa tctctaaaac gcccactggg  1860
```

```
tgacgtcacc aatactagct ataaaagtct ggagaagcgg gccaggctct catttgttcc    1920
cgagacgcct cgcagttcag acgtgactgt tgatcccgct cctctgcgac cgctcaattg    1980
gaattcaagg tatgattgca aatgtgacta tcatgctcaa tttgacaaca tttctaacaa    2040
atgtgatgaa tgtgaatatt tgaatcgggg caaaaatgga tgtatctgtc acaatgtaac    2100
tcactgtcaa atttgtcatg ggattccccc ctgggaaaag gaaaacttgt cagattttgg    2160
ggattttgac gatgccaata agaacagta ataaagcga gtagtcatgt cttttgttga    2220
tcaccctcca gattggttgg aagaagttgg tgaaggtctt cgcgagtttt tgggccttga    2280
agcgggccca ccgaaaccaa aacccaatca gcagcatcaa gatcaagccc gtggtcttgt    2340
gctgcctggt tataactatc tcggacccgg aaacggtctc gatcgaggag agcctgtcaa    2400
cagggcagac gaggtcgcgc gagagcacga catctcgtac aacgagcagc ttgaggcggg    2460
agacaacccc tacctcaagt acaaccacgc ggacgccgag tttcaggaga agctcgccga    2520
cgacacatcc ttcgggggaa acctcggaaa ggcagtcttt caggccaaga aaagggttct    2580
cgaacctttt ggcctggttg aagagggtgc taagacggcc cctaccggaa agcggataga    2640
cgaccacttt ccaaaaagaa agaaggctcg gaccgaagag gactccaagc cttccacctc    2700
gtcagacgcc gaagctggac ccagcggatc ccagcagctg caaatcccag cccaaccagc    2760
ctcaagtttg ggagctgata caatgtctgc ggggaggtggc ggcccattgg gcgacaataa    2820
ccaaggtgcc gatggagtgg gcaatgcctc gggagattgg cattgcgatt ccacgtggat    2880
gggggacaga gtcgtcacca agtccacccg aacctgggtg ctgcccagct acaacaacca    2940
ccagtaccga gagatcaaaa gcggctccgt cgacggaagc aacgccaacg cctactttgg    3000
atacagcacc ccctgggggt actttgactt taaccgcttc cacagccact ggagcccccg    3060
agactggcaa agactcatca caaactactg gggcttcaga ccccggtccc tcagagtcaa    3120
aatcttcaac attcaagtca aagaggtcac ggtgcaggac tccaccacca ccatcgccaa    3180
caacctcacc tccaccgtcc aagtgtttac ggacgacgac taccagctgc cctacgtcgt    3240
cggcaacggg accgagggat gcctgccggc cttccctccg caggtctttta cgctgccgca    3300 gtacggttac gcgacgctga accgcgacaa cacagaaaat cccaccgaga ggagcagctt    3360
cttctgccta gagtactttc ccagcaagat gctgagaacg ggcaacaact ttgagtttac    3420
ctacaacttt gaggaggtgc ccttccactc cagcttcgct cccagtcaga acctgttcaa    3480
gctggccaac ccgctggtgg accagtactt gtaccgcttc gtgagcacaa ataacactgg    3540
cggagtccag ttcaacaaga acctggccgg gagatacgcc aacacctaca aaaactggtt    3600
cccgggcccc atgggccgaa cccagggctg gaacctgggc tccggggtca accgcgccag    3660
tgtcagcgcc ttcgccacga ccaataggat ggagctcgag ggcgcgagtt accaggtgcc    3720
cccgcagccg aacggcatga ccaacaacct ccagggcagc aacacctatg ccctggagaa    3780
cactatgatc ttcaacagcc agccggcgaa cccgggcacc accgccacgt acctcgaggg    3840
caacatgctc atcaccagcg agagcgagac gcagccggtg aaccgcgtgg cgtacaacgt    3900
cggcgggcag atggccacca caaccagag ctccaccact gccccgcgca ccggcacgta    3960
caacctccag gaaatcgtgc ccggcagcgt gtggatggag agggacgtgt acctccaagg    4020
acccatctgg gccaagatcc cagagacggg ggcgcacttt caccctctc cggccatggg    4080 cggattcgga ctcaaacacc caccgcccat gatgctcatc aagaacacgc ctgtgcccgg    4140
aaatatcacc agcttctcgg acgtgccgt cagcagcttc atcacccagt acagcaccgg    4200
gcaggtcacc gtggagatgg agtgggagct caagaaggaa aactccaaga ggtggaaccc    4260
```

```
agagatccag tacacaaaca actacaacga cccccagttt gtggactttg ccccggacag    4320
caccggggaa tacagaacca ccagacctat cggaacccga taccttaccc gaccccttta    4380
acccattcat gtcgcatacc ctcaataaac cgtgtattcg tgtcagtaaa atactgcctc    4440
ttgtggtcat tcaatgaata acagcttaca acatctacaa aacctccttg cttgagagtg    4500
tggcactctc cccctgtcg cgttcgctcg ctcgctggct cgtttggggg ggtggcagct    4560
caaagagctg ccagacgacg gccctctggc cgtcgccccc ccaaacgagc cagcgagcga    4620
gcgaacgcga cagggggag ag                                              4642
```

<210> SEQ ID NO 36
<211> LENGTH: 724
<212> TYPE: PRT
<213> ORGANISM: Adeno-associated virus 5

<400> SEQUENCE: 36

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300
```

-continued

```
Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
            325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
            355                 360                 365

Ala Thr Leu Asn Arg Asp Asn Thr Glu Asn Pro Thr Glu Arg Ser Ser
370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
                420                 425                 430

Gln Tyr Leu Tyr Arg Phe Val Ser Thr Asn Asn Thr Gly Gly Val Gln
            435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
                500                 505                 510

Asn Asn Leu Gln Gly Ser Asn Thr Tyr Ala Leu Glu Asn Thr Met Ile
            515                 520                 525

Phe Asn Ser Gln Pro Ala Asn Pro Gly Thr Thr Ala Thr Tyr Leu Glu
530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
            595                 600                 605

Ala Lys Ile Pro Glu Thr Gly Ala His Phe His Pro Ser Pro Ala Met
610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
                660                 665                 670

Trp Glu Leu Lys Lys Glu Asn Ser Lys Arg Trp Asn Pro Glu Ile Gln
            675                 680                 685

Tyr Thr Asn Asn Tyr Asn Asp Pro Gln Phe Val Asp Phe Ala Pro Asp
            690                 695                 700

Ser Thr Gly Glu Tyr Arg Thr Thr Arg Pro Ile Gly Thr Arg Tyr Leu
705                 710                 715                 720
```

-continued

Thr Arg Pro Leu

<210> SEQ ID NO 37
<211> LENGTH: 4721
<212> TYPE: DNA
<213> ORGANISM: Adeno-associated virus 7

<400> SEQUENCE: 37

| | | | | | |
|---|---|---|---|---|---|
| ttggccactc | cctctatgcg | cgctcgctcg | ctcggtgggg | cctgcggacc | aaaggtccgc | 60 |
| agacggcaga | gctctgctct | gccggcccca | ccgagcgagc | gagcgcgcat | agagggagtg | 120 |
| gccaactcca | tcactagggg | taccgcgaag | cgcctcccac | gctgccgcgt | cagcgctgac | 180 |
| gtaaatcacg | tcatagggga | gtggtcctgt | attagctgtc | acgtgagtgc | ttttgcgaca | 240 |
| ttttgcgaca | ccacgtggcc | atttgaggta | tatatggccg | agtgagcgag | caggatctcc | 300 |
| attttgaccg | cgaaatttga | acgagcagca | gccatgccgg | gtttctacga | gatcgtgatc | 360 |
| aaggtgccga | gcgacctgga | cgagcacctg | ccgggcattt | ctgactcgtt | tgtgaactgg | 420 |
| gtggccgaga | aggaatggga | gctgccccg | gattctgaca | tggatctgaa | tctgatcgag | 480 |
| caggcacccc | tgaccgtggc | cgagaagctg | cagcgcgact | tcctggtcca | atggcgccgc | 540 |
| gtgagtaagg | ccccggaggc | cctgttcttt | gttcagttcg | agaagggcga | gagctacttc | 600 |
| cacctttcacg | ttctggtgga | gaccacgggg | gtcaagtcca | tggtgctagg | ccgcttcctg | 660 |
| agtcagattc | gggagaagct | ggtccagacc | atctaccgcg | gggtcgagcc | cacgctgccc | 720 |
| aactggttcg | cggtgaccaa | gacgcgtaat | ggcgccggcg | gggggaacaa | ggtggtggac | 780 |
| gagtgctaca | tccccaacta | cctcctgccc | aagacccagc | ccgagctgca | gtgggcgtgg | 840 |
| actaacatgg | aggagtatat | aagcgcgtgt | ttgaacctgg | ccgaacgcaa | acggctcgtg | 900 |
| gcgcagcacc | tgacccacgt | cagccagacg | caggagcaga | acaaggagaa | tctgaacccc | 960 |
| aattctgacg | cgcccgtgat | caggtcaaaa | acctccgcgc | gctacatgga | gctggtcggg | 1020 |
| tggctggtgg | accggggcat | cacctccgag | aagcagtgga | tccaggagga | ccaggcctcg | 1080 |
| tacatctcct | tcaacgccgc | ctccaactcg | cggtcccaga | tcaaggccgc | gctggacaat | 1140 |
| gccggcaaga | tcatggcgct | gaccaaatcc | gcgcccgact | acctggtggg | gccctcgctg | 1200 |
| cccgcggaca | ttaaaaccaa | ccgcatctac | cgcatcctgg | agctgaacgg | gtacgatcct | 1260 |
| gcctacgccg | gctccgtctt | tctcggctgg | gcccagaaaa | agttcgggaa | gcgcaacacc | 1320 |
| atctggctgt | ttgggcccgc | caccaccggc | aagaccaaca | ttgcggaagc | catcgcccac | 1380 |
| gccgtgccct | tctacggctg | cgtcaactgg | accaatgaga | ctttccctt | caacgattgc | 1440 |
| gtcgacaaga | tggtgatctg | gtgggaggag | gcaagatga | cggccaaggt | cgtggagtcc | 1500 |
| gccaaggcca | ttctcggcgg | cagcaaggtg | cgcgtggacc | aaaagtgcaa | gtcgtccgcc | 1560 |
| cagatcgacc | ccacccccgt | gatcgtcacc | tccaacacca | acatgtgcgc | cgtgattgac | 1620 |
| gggaacagca | ccaccttcga | gcaccagcag | ccgttgcagg | accggatgtt | caaatttgaa | 1680 |
| ctcacccgcc | gtctggagca | cgactttggc | aaggtgacga | agcaggaagt | caaagagttc | 1740 |
| ttccgctggg | ccagtgatca | cgtgaccgag | gtggcgcatg | agttctacgt | cagaaagggc | 1800 |
| ggagccagca | aaagacccgc | cccgatgac | gcggatataa | gcgagcccaa | gcgggcctgc | 1860 |
| ccctcagtcg | cggatccatc | gacgtcagac | gcggaaggag | ctccggtgga | ctttgccgac | 1920 |
| aggtaccaaa | acaaatgttc | tcgtcacgcg | ggcatgattc | agatgctgtt | tccctgcaaa | 1980 |
| acgtgcgaga | gaatgaatca | gaatttcaac | atttgcttca | cacacgggt | cagagactgt | 2040 |
| ttagagtgtt | tccccggcgt | gtcagaatct | caaccggtcg | tcagaaaaaa | gacgtatcgg | 2100 |

```
aaactctgcg cgattcatca tctgctgggg cgggcgcccg agattgcttg ctcggcctgc    2160
gacctggtca acgtggacct ggacgactgc gtttctgagc aataaatgac ttaaaccagg    2220
tatggctgcc gatggttatc ttccagattg gctcgaggac aacctctctg agggcattcg    2280
cgagtggtgg gacctgaaac ctggagcccc gaaacccaaa gccaaccagc aaaagcagga    2340
caacggccgg ggtctggtgc ttcctggcta caagtacctc ggacccttca acggactcga    2400 caaggggag cccgtcaacg cggcggacgc agcggccctc gagcacgaca aggcctacga    2460
ccagcagctc aaagcgggtg acaatccgta cctgcggtat aaccacgccg acgccgagtt    2520
tcaggagcgt ctgcaagaag atacgtcatt tgggggcaac ctcgggcgag cagtcttcca    2580
ggccaagaag cggttctcg aacctctcgg tctggttgag gaaggcgcta agacggctcc    2640
tgcaaagaag agaccggtag agccgtcacc tcagcgttcc cccgactcct ccacgggcat    2700
cggcaagaaa ggccagcagc ccgccagaaa gagactcaat ttcggtcaga ctggcgactc    2760
agagtcagtc cccgacccctc aacctctcgg agaacctcca gcagcgccct ctagtgtggg    2820
atctggtaca gtggctgcag gcggtggcgc accaatggca gacaataacg aaggtgccga    2880
cggagtgggt aatgcctcag gaaattggca ttgcgattcc acatggctgg gcgacagagt    2940
cattaccacc agcacccgaa cctgggccct gcccacctac aacaaccacc tctacaagca    3000
aatctccagt gaaactgcag gtagtaccaa cgacaacacc tacttcggct acagcacccc    3060
ctgggggtat tttgacttta acagattcca ctgccacttc tcaccacgtg actggcagcg    3120
actcatcaac aacaactggg gattccggcc caagaagctg cggttcaagc tcttcaacat    3180
ccaggtcaag gaggtcacga cgaatgacgg cgttacgacc atcgctaata accttaccag    3240
cacgattcag gtattctcgg actcggaata ccagctgccg tacgtcctcg gctctgcgca    3300
ccagggctgc ctgcctccgt tcccggcgga cgtcttcatg attcctcagt acggctacct    3360
gactctcaac aatggcagtc agtctgtggg acgttcctcc ttctactgcc tggagtactt    3420
cccctctcag atgctgagaa cgggcaacaa cttttgagttc agctacagct tcgaggacgt    3480
gcctttccac agcagctacg cacacagcca gagcctggac cggctgatga atccctcat    3540 cgaccagtac ttgtactacc tggccagaac acagagtaac ccaggaggca cagctggcaa    3600
tcgggaactg cagttttacc agggcgggcc ttcaactatg gccgaacaag ccaagaattg    3660
gttacctgga ccttgcttcc ggcaacaaag agtctccaaa acgctggatc aaaacaacaa    3720
cagcaacttt gcttggactg gtgccaccaa atatcacctg aacggcagaa actcgttggt    3780 taatccggc gtcgccatgg caactcacaa ggacgacgag gaccgctttt tcccatccag    3840
cggagtcctg attttggaa aaactggagc aactaacaaa actacattgg aaaatgtgtt    3900
aatgacaaat gaagaagaaa ttcgtcctac taatcctgta gccacggaag aatacgggat    3960
agtcagcagc aacttacaag cggctaatac tgcagcccag acacaagttg tcaacaacca    4020
gggagcctta cctggcatgg tctggcagaa ccgggacgtg tacctgcagg gtcccatctg    4080
ggccaagatt cctcacacgg atggcaactt tcacccgtct cctttgatgg gcggcttttgg    4140 acttaaacat ccgcctcctc agatcctgat caagaacact cccgttcccg ctaatcctcc    4200
ggaggtgttt actcctgcca gtttgcttc gttcatcaca cagtacagca ccggacaagt    4260
cagcgtggaa atcgagtggg agctgcagaa ggaaaacagc aagcgctgga accccggagat    4320 tcagtacacc tccaacttg aaaagcagac tggtgtggac tttgccgttg acagccaggg    4380
tgtttactct gagcctcgcc ctattggcac tcgttacctc acccgtaatc tgtaattgca    4440
```

-continued

```
tgttaatcaa taaaccggtt gattcgtttc agttgaactt tggtctcctg tgcttcttat    4500
cttatcggtt tccatagcaa ctggttacac attaactgct tgggtgcgct tcacgataag    4560
aacactgacg tcaccgcggt accccctagtg atggagttgg ccactccctc tatgcgcgct    4620
cgctcgctcg gtggggcctg cggaccaaag gtccgcagac ggcagagctc tgctctgccg    4680
gccccaccga gcgagcgagc gcgcatagag ggagtggcca a                        4721
```

<210> SEQ ID NO 38
<211> LENGTH: 737
<212> TYPE: PRT
<213> ORGANISM: Adeno-associated virus 7

<400> SEQUENCE: 38

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
```

-continued

```
                    325                 330                 335
Asn Leu Thr Ser Thr Ile Gln Val Phe Ser Asp Ser Glu Tyr Gln Leu
                340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
        370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln
    450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu
```

<210> SEQ ID NO 39
<211> LENGTH: 4393
<212> TYPE: DNA
<213> ORGANISM: Adeno-associated virus 8

<400> SEQUENCE: 39

```
cagagaggga gtggccaact ccatcactag gggtagcgcg aagcgcctcc cacgctgccg      60
cgtcagcgct gacgtaaatt acgtcatagg ggagtggtcc tgtattagct gtcacgtgag    120
tgcttttgcg gcattttgcg acaccacgtg gccatttgag gtatatatgg ccgagtgagc    180
gagcaggatc tccattttga ccgcgaaatt tgaacgagca gcagccatgc cgggcttcta    240
cgagatcgtg atcaaggtgc cgagcgacct ggacgagcac ctgccgggca tttctgactc    300
gtttgtgaac tgggtggccg agaaggaatg ggagctgccc ccggattctg acatggatcg    360
gaatctgatc gagcaggcac ccctgaccgt ggccgagaag ctgcagcgcg acttcctggt    420
ccaatggcgc cgcgtgagta aggccccgga ggccctcttc tttgttcagt cgagaaggg     480
cgagagctac tttcacctgc acgttctggt cgagaccacg ggggtcaagt ccatggtgct    540
aggccgcttc ctgagtcaga ttcgggaaaa gcttggtcca gaccatctac ccgcggggtc    600
gagccccacc ttgcccaact ggttcgcggt gaccaaagac gcggtaatgg cgccggcggg    660
ggggaacaag gtggtggacg agtgctacat ccccaactac ctcctgccca agactcagcc    720
cgagctgcag tgggcgtgga ctaacatgga ggagtatata agcgcgtgct tgaacctggc    780
cgagcgcaaa cggctcgtgg cgcagcacct gacccacgtc agccagacgc aggagcagaa    840
caaggagaat ctgaacccca attctgacgc gcccgtgatc aggtcaaaaa cctccgcgcg    900
ctatatggag ctggtcgggt ggctggtgga ccggggcatc acctccgaga agcagtggat    960
ccaggaggac caggcctcgt acatctcctt caacgccgcc tccaactcgc ggtcccagat   1020
caaggccgcg ctgacaatg ccggcaagat catggcgctg accaaatccg cgcccgacta   1080
cctggtgggg cccctcgctg ccgcggacat acccagaac cgcatctacc gcatcctcgc   1140
tctcaacggc tacgaccctg cctacgccgg ctccgtcttt ctcggctggg ctcagaaaaa   1200
gttcgggaaa cgcaacacca tctggctgtt tggacccgcc accaccggca agaccaacat   1260
tgcggaagcc atcgcccacg ccgtgccctt ctacggctgc gtcaactgga ccaatgagaa   1320
ctttcccttc aatgattgcg tcgacaagat ggtgatctgg tgggaggagg caagatgac   1380
ggccaaggtc gtggagtccg ccaaggccat tctcggcggc agcaaggtgc gcgtggacca   1440
aaagtgcaag tcgtccgccc agatcgaccc caccccgtg atcgtcacct ccaacaccaa   1500
catgtgcgcc gtgattgacg ggaacagcac caccttcgag caccagcagc ctctccagga   1560
ccgggatgttt aagttcgaac tcacccgccg tctggagcac actttggca aggtgacaaa   1620
gcaggaagtc aaagagttct tccgctgggc cagtgatcac gtgaccgagg tggcgcatga   1680
gttttacgtc agaaagggcg gagccagcaa agaccccgcc ccgatgacg cggataaaag   1740
cgagcccaag cgggcctgcc cctcagtcgc ggatccatcg acgtcagacg cggaaggagc   1800
tccggtggac tttgccgaca ggtaccaaaa caaatgttct cgtcacgcgg gcatgcttca   1860
gatgctgttt ccctgcaaaa cgtgcgagag aatgaatcag aatttcaaca tttgcttcac   1920
acacggggtc agagactgct cagagtgttt ccccggcgtg tcagaatctc aaccggtcgt   1980
cagaaagagg acgtatcgga aactctgtgc gattcatcat ctgctggggc gggctcccga   2040
gattgcttgc tcggcctgcg atctggtcaa cgtggacctg gatgactgtg tttctgagca   2100
ataaatgact taaaccaggt atggctgccg atggttatct tccagattgg ctcgaggaca   2160
```

-continued

```
acctctctga gggcattcgc gagtggtggg cgctgaaacc tggagcccg aagcccaaag    2220
ccaaccagca aaagcaggac gacggccggg gtctggtgct tcctggctac aagtacctcg   2280
gacccttcaa cggactcgac aagggggagc ccgtcaacgc ggcggacgca gcggccctcg   2340
agcacgacaa ggcctacgac cagcagctgc aggcgggtga caatccgtac ctgcggtata   2400
accacgccga cgccgagttt caggagcgtc tgcaagaaga tacgtctttt ggggcaacc    2460
tcgggcgagc agtcttccag gccaagaagc gggttctcga acctctcggt ctggttgagg   2520
aaggcgctaa gacggctcct ggaaagaaga gaccggtaga gccatcaccc cagcgttctc   2580
cagactcctc tacgggcatc ggcaagaaag ccaacagcc cgccagaaaa agactcaatt    2640
ttggtcagac tggcgactca gagtcagttc cagaccctca acctctcgga gaacctccag   2700
cagcgccctc tggtgtggga cctaatacaa tggctgcagg cggtggcgca ccaatggcag   2760
acaataacga aggcgccgac ggagtgggta gttcctcggg aaattggcat tgcgattcca   2820
catggctggg cgacagagtc atcaccacca gcacccgaac ctgggccctg cccacctaca   2880
acaaccacct ctacaagcaa atctccaacg ggacatcggg aggagccacc aacgacaaca   2940
cctacttcgg ctacagcacc ccctgggggt attttgactt taacagattc cactgccact   3000
tttcaccacg tgactggcag cgactcatca acaacaactg gggattccgg cccaagagac   3060
tcagcttcaa gctcttcaac atccaggtca aggaggtcac gcagaatgaa ggcaccaaga   3120
ccatcgccaa taacctcacc agcaccatcc aggtgtttac ggactcggag taccagctgc   3180
cgtacgttct cggctctgcc caccagggct gcctgcctcc gttcccggcg gacgtgttca   3240
tgattcccca gtacggctac ctaacactca caacggtag tcaggccgtg ggacgctcct    3300
ccttctactg cctggaatac tttccttcgc agatgctgag aaccggcaac aacttccagt   3360
ttacttacac cttcgaggac gtgcctttcc acagcagcta cgcccacagc cagagcttgg   3420
accggctgat gaatcctctg attgaccagt acctgtacta cttgtctcgg actcaaacaa   3480
caggaggcac ggcaaatacg cagactctgg gcttcagcca aggtgggcct aatacaatgg   3540
ccaatcaggc aaagaactgg ctgccaggac cctgttaccg ccaacaacgc gtctcaacga   3600
caaccgggca aaacaacaat agcaactttg cctggactgc tgggaccaaa taccatctga   3660
atggaagaaa ttcattggct aatcctggca tcgctatggc aacacacaaa gacgacgagg   3720
agcgtttttt tcccagtaac gggatcctga ttttggcaa acaaaatgct gccagagaca   3780
atgcggatta cagcgatgtc atgctcacca gcgaggaaga aatcaaaacc actaaccctg   3840
tggctacaga ggaatacggt atcgtggcag ataacttgca gcagcaaaac acggctcctc   3900
aaattggaac tgtcaacagc caggggggcct tacccggtat ggtctggcag aaccgggacg   3960
tgtacctgca gggtcccatc tgggccaaga ttcctcacac ggacggcaac ttccacccgt   4020
ctccgctgat gggcggcttt ggcctgaaac atcctccgcc tcagatcctg atcaagaaca   4080
cgcctgtacc tgcggatcct ccgaccacct tcaaccagtc aaagctgaac tctttcatca   4140
cgcaatacag caccggacag gtcagcgtgg aaattgaatg ggagctgcag aaggaaaaca   4200
gcaagcgctg gaacccgag atccagtaca cctccaacta ctacaaatct acaagtgtgg    4260
actttgctgt taatacagaa ggcgtgtact ctgaaccccg ccccattggc acccgttacc   4320
tcacccgtaa tctgtaattg cctgttaatc aataaaccgg ttgattcgtt tcagttgaac   4380
tttggtctct gcg                                                     4393
```

<210> SEQ ID NO 40

<211> LENGTH: 738
<212> TYPE: PRT
<213> ORGANISM: Adeno associated virus 8

<400> SEQUENCE: 40

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
            165                 170                 175

Thr Gly Asp Ser Glu Ser Val Pro Asp Pro Gln Pro Leu Gly Glu Pro
        180                 185                 190

Pro Ala Ala Pro Ser Gly Val Gly Pro Asn Thr Met Ala Ala Gly Gly
    195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
            245                 250                 255

Leu Tyr Lys Gln Ile Ser Asn Gly Thr Ser Gly Gly Ala Thr Asn Asp
        260                 265                 270

Asn Thr Tyr Phe Gly Tyr Ser Thr Pro Trp Gly Tyr Phe Asp Phe Asn
    275                 280                 285

Arg Phe His Cys His Phe Ser Pro Arg Asp Trp Gln Arg Leu Ile Asn
290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
            325                 330                 335

Asn Asn Leu Thr Ser Thr Ile Gln Val Phe Thr Asp Ser Glu Tyr Gln
        340                 345                 350

Leu Pro Tyr Val Leu Gly Ser Ala His Gln Gly Cys Leu Pro Pro Phe
    355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
```

```
                385                 390                 395                 400

Phe Pro Ser Gln Met Leu Arg Thr Gly Asn Asn Phe Gln Phe Thr Tyr
                        405                 410                 415

Thr Phe Glu Asp Val Pro Phe His Ser Ser Tyr Ala His Ser Gln Ser
                    420                 425                 430

Leu Asp Arg Leu Met Asn Pro Leu Ile Asp Gln Tyr Leu Tyr Tyr Leu
                    435                 440                 445

Ser Arg Thr Gln Thr Thr Gly Gly Thr Ala Asn Thr Gln Thr Leu Gly
                450                 455                 460

Phe Ser Gln Gly Gly Pro Asn Thr Met Ala Asn Gln Ala Lys Asn Trp
        465                 470                 475                 480

Leu Pro Gly Pro Cys Tyr Arg Gln Gln Arg Val Ser Thr Thr Thr Gly
                        485                 490                 495

Gln Asn Asn Asn Ser Asn Phe Ala Trp Thr Ala Gly Thr Lys Tyr His
                    500                 505                 510

Leu Asn Gly Arg Asn Ser Leu Ala Asn Pro Gly Ile Ala Met Ala Thr
                    515                 520                 525

His Lys Asp Asp Glu Glu Arg Phe Phe Pro Ser Asn Gly Ile Leu Ile
                530                 535                 540

Phe Gly Lys Gln Asn Ala Ala Arg Asp Asn Ala Asp Tyr Ser Asp Val
        545                 550                 555                 560

Met Leu Thr Ser Glu Glu Ile Lys Thr Thr Asn Pro Val Ala Thr
                        565                 570                 575

Glu Glu Tyr Gly Ile Val Ala Asp Asn Leu Gln Gln Asn Thr Ala
                    580                 585                 590

Pro Gln Ile Gly Thr Val Asn Ser Gln Gly Ala Leu Pro Gly Met Val
                    595                 600                 605

Trp Gln Asn Arg Asp Val Tyr Leu Gln Gly Pro Ile Trp Ala Lys Ile
                610                 615                 620

Pro His Thr Asp Gly Asn Phe His Pro Ser Pro Leu Met Gly Gly Phe
        625                 630                 635                 640

Gly Leu Lys His Pro Pro Gln Ile Leu Ile Lys Asn Thr Pro Val
                        645                 650                 655

Pro Ala Asp Pro Pro Thr Thr Phe Asn Gln Ser Lys Leu Asn Ser Phe
                    660                 665                 670

Ile Thr Gln Tyr Ser Thr Gly Gln Val Ser Val Glu Ile Glu Trp Glu
                    675                 680                 685

Leu Gln Lys Glu Asn Ser Lys Arg Trp Asn Pro Glu Ile Gln Tyr Thr
                690                 695                 700

Ser Asn Tyr Tyr Lys Ser Thr Ser Val Asp Phe Ala Val Asn Thr Glu
        705                 710                 715                 720

Gly Val Tyr Ser Glu Pro Arg Pro Ile Gly Thr Arg Tyr Leu Thr Arg
                        725                 730                 735

Asn Leu

<210> SEQ ID NO 41
<211> LENGTH: 738
<212> TYPE: PRT
<213> ORGANISM: Adeno-associated virus 10

<400> SEQUENCE: 41

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
```

-continued

```
                20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Ala Ala Lys Thr Ala Pro Gly Lys Lys Arg
    130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Lys Lys Arg Leu Asn Phe Gly Gln
                165                 170                 175
Thr Gly Glu Ser Glu Ser Val Pro Asp Pro Gln Pro Ile Gly Glu Pro
            180                 185                 190
Pro Ala Gly Pro Ser Gly Leu Gly Ser Gly Thr Met Ala Ala Gly Gly
        195                 200                 205
Gly Ala Pro Met Ala Asp Asn Asn Glu Gly Ala Asp Gly Val Gly Ser
    210                 215                 220
Ser Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Asn Gly Thr Ser Gly Gly Ser Thr Asn Asp
            260                 265                 270
Asn Thr Tyr Phe Gly Tyr Ser Thr Pro Trp Gly Tyr Phe Asp Phe Asn
        275                 280                 285
Arg Phe His Cys His Phe Ser Pro Arg Asp Trp Gln Arg Leu Ile Asn
    290                 295                 300
Asn Asn Trp Gly Phe Arg Pro Lys Arg Leu Ser Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
            340                 345                 350
Leu Pro Tyr Val Leu Gly Ser Ala His Gln Gly Cys Leu Pro Pro Phe
        355                 360                 365
Pro Ala Asp Val Phe Met Ile Pro Gln Tyr Gly Tyr Leu Thr Leu Asn
    370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
Thr Phe Glu Asp Val Pro Phe His Ser Ser Tyr Ala His Ser Gln Ser
            420                 425                 430
Leu Asp Arg Leu Met Asn Pro Leu Ile Asp Gln Tyr Leu Tyr Tyr Leu
        435                 440                 445
```

```
Ser Arg Thr Gln Ser Thr Gly Gly Thr Gln Gly Thr Gln Gln Leu Leu
    450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
                500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
        530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Ala Asn Thr Gly
                580                 585                 590

Pro Ile Val Gly Asn Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 42
<211> LENGTH: 733
<212> TYPE: PRT
<213> ORGANISM: Adeno-associated virus 11

<400> SEQUENCE: 42

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80
```

-continued

```
Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
            115                 120                 125

Leu Gly Leu Val Glu Gly Ala Lys Thr Ala Pro Gly Lys Lys Arg
        130                 135                 140

Pro Leu Glu Ser Pro Gln Glu Pro Asp Ser Ser Gly Ile Gly Lys
145                 150                 155                 160

Lys Gly Lys Gln Pro Ala Arg Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
            195                 200                 205

Gly Gln Gly Ser Asp Gly Val Gly Asn Ala Ser Gly Asp Trp His Cys
        210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Ser Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
            275                 280                 285

Arg Leu Ile Asn Asn Asn Trp Gly Leu Arg Pro Lys Ala Met Arg Val
        290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
            355                 360                 365

Cys Gly Ile Val Thr Gly Glu Asn Gln Asn Gln Thr Asp Arg Asn Ala
        370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
                405                 410                 415

Tyr Ala His Ser Gln Ser Leu Asp Arg Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495
```

```
Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
        515                 520                 525

Asp Gly Asp Phe Ser Asn Ala Gln Leu Ile Phe Pro Gly Pro Ser Val
    530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
        595                 600                 605

Ile Tyr Tyr Gln Gly Pro Ile Trp Ala Lys Ile Pro His Ala Asp Gly
    610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
        675                 680                 685

Ser Lys Arg Trp Asn Pro Glu Val Gln Phe Thr Ser Asn Tyr Gly Asn
    690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 43
<211> LENGTH: 735
<212> TYPE: PRT
<213> ORGANISM: Adeno-associated virus 9

<400> SEQUENCE: 43

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Gln Asp Asn Ser Arg Gly Leu Val Leu Pro
        35                  40                  45

Gly Tyr Lys Tyr Leu Gly Pro Ser Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140
```

-continued

```
Pro Val Glu His Ser Pro Val Glu Pro Asp Ser Ser Gly Thr Gly
145                 150                 155                 160

Lys Ala Gly His Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Thr Ser Leu Gly Ser Thr Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Cys Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Pro Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Ser Asn Ser Gly Thr Leu Gln Gln Ser Arg Leu Leu Phe Ser Gln
    450                 455                 460

Ala Gly Pro Thr Ser Met Ser Leu Gln Ala Lys Asn Trp Leu Pro Gly
465                 470                 475                 480

Pro Cys Tyr Arg Gln Gln Arg Leu Ser Lys Gln Ala Asn Asp Asn Asn
                485                 490                 495

Asn Ser Asn Phe Pro Trp Thr Ala Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Met His Gly Thr Leu Ile Phe Gly Lys
    530                 535                 540

Gln Gly Thr Asn Ala Asn Asp Ala Asp Leu Glu His Val Met Ile Thr
545                 550                 555                 560
```

```
Asp Glu Glu Glu Ile Arg Thr Thr Asn Pro Val Ala Thr Glu Gln Tyr
                565                 570                 575
Gly Asn Val Ser Asn Asn Leu Gln Asn Ser Asn Thr Gly Pro Thr Thr
            580                 585                 590
Glu Asn Val Asn His Gln Gly Ala Leu Pro Gly Met Val Trp Gln Asp
        595                 600                 605
Arg Asp Val Tyr Leu Gln Gly Pro Ile Trp Ala Lys Ile Pro His Thr
610                 615                 620
Asp Gly His Phe His Pro Ser Pro Leu Met Gly Gly Phe Gly Leu Lys
625                 630                 635                 640
His Pro Pro Pro Gln Ile Met Ile Lys Asn Thr Pro Val Pro Ala Asn
                645                 650                 655
Pro Pro Thr Asn Phe Ser Ser Ala Lys Phe Ala Ser Phe Ile Thr Gln
            660                 665                 670
Tyr Ser Thr Gly Gln Val Ser Val Glu Ile Glu Trp Glu Leu Gln Lys
        675                 680                 685
Glu Asn Ser Lys Arg Trp Asn Pro Glu Ile Gln Tyr Thr Ser Asn Tyr
    690                 695                 700
Asn Lys Ser Val Asn Val Asp Phe Thr Val Asp Thr Asn Gly Val Tyr
705                 710                 715                 720
Ser Glu Pro Cys Pro Ile Gly Thr Arg Tyr Leu Thr Arg Asn Leu
                725                 730                 735

<210> SEQ ID NO 44
<211> LENGTH: 10
<212> TYPE: PRT
<213> ORGANISM: Artificial sequence
<220> FEATURE:
<223> OTHER INFORMATION: Synthetic peptide

<400> SEQUENCE: 44

Pro Gln Arg Arg Ser Ala Arg Leu Ser Ala
1               5                   10

<210> SEQ ID NO 45
<211> LENGTH: 31
<212> TYPE: PRT
<213> ORGANISM: Artificial sequence
<220> FEATURE:
<223> OTHER INFORMATION: Synthetic peptide

<400> SEQUENCE: 45

Lys Asp Glu Pro Gln Arg Arg Ser Ala Arg Leu Ser Ala Lys Pro Ala
1               5                   10                  15
Pro Pro Lys Pro Glu Pro Lys Pro Lys Lys Ala Pro Ala Lys Lys
            20                  25                  30

<210> SEQ ID NO 46
<211> LENGTH: 12
<212> TYPE: PRT
<213> ORGANISM: Artificial sequence
<220> FEATURE:
<223> OTHER INFORMATION: Synthetic peptide

<400> SEQUENCE: 46

Gln Arg Gly Asn Arg Gln Ala Ala Thr Ala Asp Val
1               5                   10

<210> SEQ ID NO 47
<211> LENGTH: 12
<212> TYPE: PRT
```

-continued

```
<213> ORGANISM: Artificial sequence
<220> FEATURE:
<223> OTHER INFORMATION: Synthetic peptide

<400> SEQUENCE: 47

Gln Ser Ser Ser Thr Asp Pro Ala Thr Gly Asp Val
1               5                   10

<210> SEQ ID NO 48
<211> LENGTH: 12
<212> TYPE: PRT
<213> ORGANISM: Artificial sequence
<220> FEATURE:
<223> OTHER INFORMATION: Synthetic peptide

<400> SEQUENCE: 48

Gln Ser Ser Asn Thr Ala Pro Thr Thr Arg Thr Val
1               5                   10

<210> SEQ ID NO 49
<211> LENGTH: 12
<212> TYPE: PRT
<213> ORGANISM: Artificial sequence
<220> FEATURE:
<223> OTHER INFORMATION: Synthetic peptide

<400> SEQUENCE: 49

Gln Ser Asn Ser Asn Leu Pro Thr Val Asp Arg Leu
1               5                   10

<210> SEQ ID NO 50
<211> LENGTH: 12
<212> TYPE: PRT
<213> ORGANISM: Artificial sequence
<220> FEATURE:
<223> OTHER INFORMATION: Synthetic peptide

<400> SEQUENCE: 50

Gln Ser Ser Thr Thr Ala Pro Ala Thr Gly Thr Tyr
1               5                   10
```